United States Patent
Johansson et al.

(10) Patent No.: US 10,626,152 B2
(45) Date of Patent: Apr. 21, 2020

(54) CHARGE-REVERSED N-TERMINAL SPIDER SILK PROTEIN DOMAIN AND USES THEREOF

(71) Applicant: SPIBER TECHNOLOGIES AB, Stockholm (SE)

(72) Inventors: Jan Johansson, Stockholm (SE); Anna Rising, Uppsala (SE); Nina Kronqvist, Årsta (SE); Kerstin Nordling, Stockholm (SE)

(73) Assignee: SPIBER TECHNOLOGIES AB, Stockholm (SE)

( * ) Notice: Subject to any disclaimer, the term of this patent is extended or adjusted under 35 U.S.C. 154(b) by 0 days.

(21) Appl. No.: 15/544,945

(22) PCT Filed: Nov. 11, 2016

(86) PCT No.: PCT/EP2016/077415
§ 371 (c)(1),
(2) Date: Jul. 20, 2017

(87) PCT Pub. No.: WO2017/081239
PCT Pub. Date: May 18, 2017

(65) Prior Publication Data
US 2018/0273590 A1 Sep. 27, 2018

(30) Foreign Application Priority Data

Nov. 13, 2015 (EP) ..................... 15194623
Aug. 31, 2016 (EP) ..................... 16186679
Oct. 10, 2016 (EP) ..................... 16193082

(51) Int. Cl.
C07K 14/435 (2006.01)
C07K 1/36 (2006.01)

(52) U.S. Cl.
CPC .......... C07K 14/43518 (2013.01); C07K 1/36 (2013.01); C07K 2319/00 (2013.01); C07K 2319/35 (2013.01)

(58) Field of Classification Search
None
See application file for complete search history.

(56) References Cited

U.S. PATENT DOCUMENTS 9,644,012 B2 * 5/2017 Johansson .............. C12N 15/62

FOREIGN PATENT DOCUMENTS

| EP | 2243792 A1 | 10/2010 |
|----|-----------|---------|
| EP | 2 644 619 A1 | 10/2013 |
| WO | WO 95/31540 A1 | 11/1995 |
| WO | WO 2009/062195 A2 | 5/2009 |
| WO | WO 2010/123450 A1 | 10/2010 |
| WO | WO 2011/115538 A1 | 9/2011 |
| WO | WO 2017/109477 A2 | 6/2017 |

OTHER PUBLICATIONS

International Search Report and Written Opinion of the International Searching Authority (Forms PCT/ISA/220, PCT/ISA/210 and PCT/ISA/237) issued in International Application No. PCT/GB2016/054004 dated Jul. 26, 2017.
International Search Report (PCT/ISA/210) issued in PCT/EP2016/077415, dated Feb. 2, 2017.
Jaudzems et al., "pH-Dependent Dimerization of Spider Silk N-Terminal Domain Requires Relocation of a Wedged Tryptophan Side Chain", Journal of Molecular Biology, vol. 422, 2012, pp. 477-487.
Kronqvist et al., "Sequential pH-driven dimerization and stabilization of the N-terminal domain enables rapid spider silk formation", Nature Communications, vol. 5, No. 3254, 2014, pp. 1-11.
Otikovs et al., "Diversified Structural Basis of a Conserved Molecular Mechanism for pH-Dependent Dimerization in Spider Silk N-Terminal Domains", ChemBioChem, vol. 16, 2015, pp. 1720-1724.
Rising et al., "Toward spinning artificial spider silk", Nature Chemical Biology, vol. 11, May 2015, pp. 309-315.
Watson et al., "Novel expression of a functional trimeric fragment of human SP-A with efficacy in neutralisation of RSV", Immunobiology, 2016, pp. 1-8.
Written Opinion (PCT/ISA/237) issued in PCT/EP2016/077415, dated Feb. 2, 2017.

* cited by examiner

*Primary Examiner* — Anand U Desai
(74) *Attorney, Agent, or Firm* — Birch, Stewart, Kolasch & Birch, LLP

(57) ABSTRACT

A protein comprising a moiety of 100-160 amino acid residues having at least 70% identity with the N-terminal (NT) fragment of a spider silk protein, wherein the amino acid residue corresponding to position 40 in NT is selected from the group consisting of Lys, Arg and His; and wherein the amino acid residue corresponding to position 65 in NT is selected from the group consisting of Asp and Glu, is useful as a moiety in a fusion protein for enhancing the solubility of another moiety in the fusion protein, which is a desired protein or polypeptide.

10 Claims, 16 Drawing Sheets
Specification includes a Sequence Listing.

Ea MaSp1      SHTTPWTNPGLAENFMNSFMQGLSSMPGFTASQLDDMSTIAQSMVQSIQSLAAQGRTSPNKLQALNMAFA
Lg MaSp1      QANTPWSSKANADAFINSFISSAQNTGSFSQDQMDDMSLIGNTLMTAMDNMG--GRITPSKLQALDMAFA
Lh MaSp1      QANTPWSSKANADAFINSFISAASNTGSFSQDQMEDMSLIGNTLMAAMDNMG--GRITPSKLQALDMAFA
Nc MaSp1      -QNTPWSSTELADAFINAFMNEAGRTGAFTADQLDDMSTIGDTIKTAMDKMARSNKSSKGKLQALNMAFA
At MaSp2      QGATPWENSQLAESFISRFLRFIGQSGAFSPNQLDDMSSIGDTLKTAIEKMAQSRKSKSKLQALNMAFA
Lg MaSp2      ---LRWSSKDNADRFINAFLQAASNSGAFSSDQVDDMSVIGNTLMTAMDNMG--GRITPSKLQALDMAFA
Lh MaSp2      QANTPWSSKENADAFIGAFMNAASQSGAFSSDQIDDMSVISNTLMAAMDNMG--GRITQSKLQALDMAFA
Nim MaSp2     QANTPWSDTATADAFIQNFLGAVSGSGAFTPDQLDDMSTVGDTIMSAMDKMARSNKSKSKLQALNMAFA
Nc MaSp2      QARSPWSDTATADAFIQNFLAAVSGSGAFTSDQLDDMSTIGDTIMSAMDKMARSNKSSQHKLQALNMAFA
Ab CySp1      AVPSVFSSPNLASGFLQCLTFGIGNSPAFPTQEQQDLDAIAQVILNAVSSNTGATASAR--AQALSTALA
Ncl CySp1     PVPSVFSSPSLASGFLGCLTTGIGLSPAFPFQEQQDLDDLAKVILSAVTSNTDTSKSAR--AQAISTALA
Lh TuSp1      ASVNIFNSPNAATSFLNCLRSNIESSPAFPFQEQADLDSIAEVILSDVSS-VNTASSAT--SIAISTALA
Nc flag       IANSPFSNPNTAEAFARSFVSNIVSSGEFGAQGAEDFDDIIQSLIQAQ-SMGKGRHDTKAKAKAMQVALA
Nlm flag      IVNSPFSNPNTAEAFARSFVSNVVSSGEFGAQGAEDFDDIIQSLIQAQ-SMGKGRHDTKAKAKAMQVALA Ea MaSp1      SSMAEIAASEEGGGSLSTKTSSIASAMSNAFLQTTGVVNQPFINEITQLVSMFAQAGMNDV
Lg MaSp1      SSVAEIAASEG--GDLGVTTNAIADALTSAFYQTTGVVNRFISEIRSLISMFAQASANDV
Lh MaSp1      SSVAEIAASEG--GDLGVTTNAIADALTSAFYQTTGVVNSRFISEIRSLIGMFAQASANDV
Nc MaSp1      SSMAEIAAVEQGGLSVDAKTNAIADSLNSAFYQTTGAANPQFVNEIRSLINMFAQSSANEV
At MaSp2      SSMAEIAVAEQGLSLEAKTNAIASALSAAFLETTGYVNQQFVNEIKTLIFMIAQASSNEI
Lg MaSp2      SSVAEIAVADG--QNVGGATNAISNALRSAFYQTTGVVNNQFISEISNLINMFAQVSANEV
Lh MaSp2      SSVAEIAVADG--QNVGAATNAISDALRSAFYQTTGVVNNQFITGISSLIGMFAQVSGNEV
Nim MaSp2     SSMAEIAAVEQGGQSMDVKTNAIANALDSAFYMTTGSTNQQFVNEMRSLINMLSAAAVNEV
Nc MaSp2      SSMAEIAAVEQGGMSMAVKTNAIVDGLNSAFYMTTGAANPQFVNEMRSLISMISAASANEV
Ab CySp1      SSLTDLLIAESAESNYSNQLSELTGILSDCFIQTTGSDNPAFVSRIQSLISVLSQNADTNI
Ncl CySp1     SSLADLLISESSGSSYQTQISALTNILSDCFVTTGSNNPAFVSRVQTLIGVLSQSSSNAI
Lh TuSp1      SSLAELLVTESAEEDIDNQVVALSTILSQCFVETTGSPNPAFVASVKSLLGVLSQSASNYE
Nc flag       SSIAELVIAESSGGDVQRKTNVISNALRNALMSTTGSPNEEFVHEVQDLIQMLSEQINEV
Nlm flag      SSIAELVIAESSGGDVQRKTNVISNALRNALMSTTGSPNEEFVHEVQDLIQMLSEQINEV

Fig 8
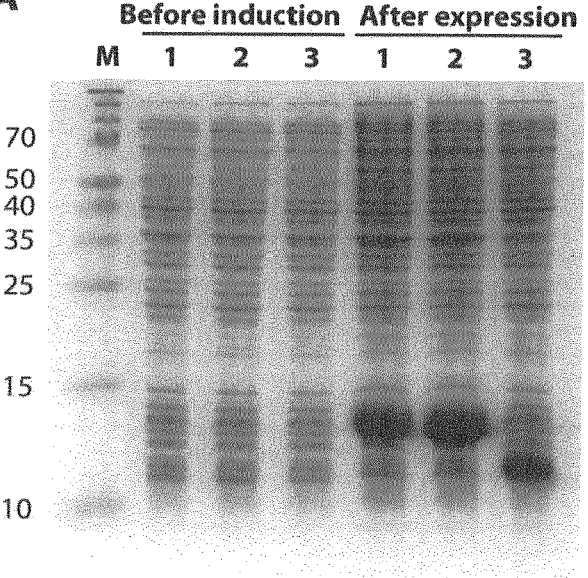
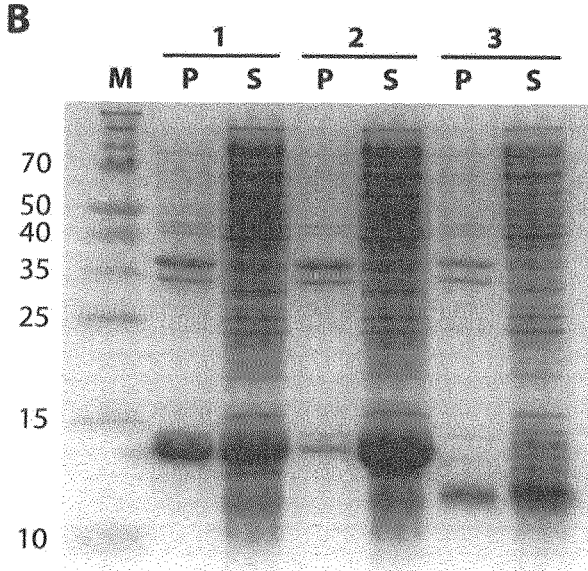
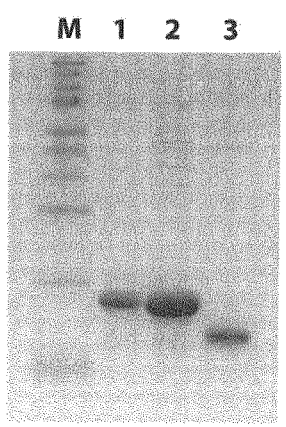
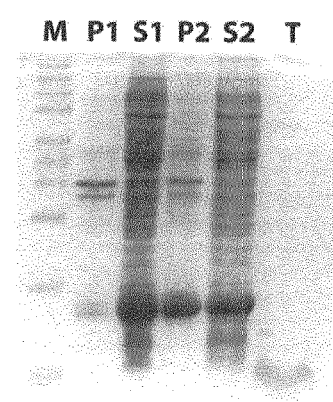

A
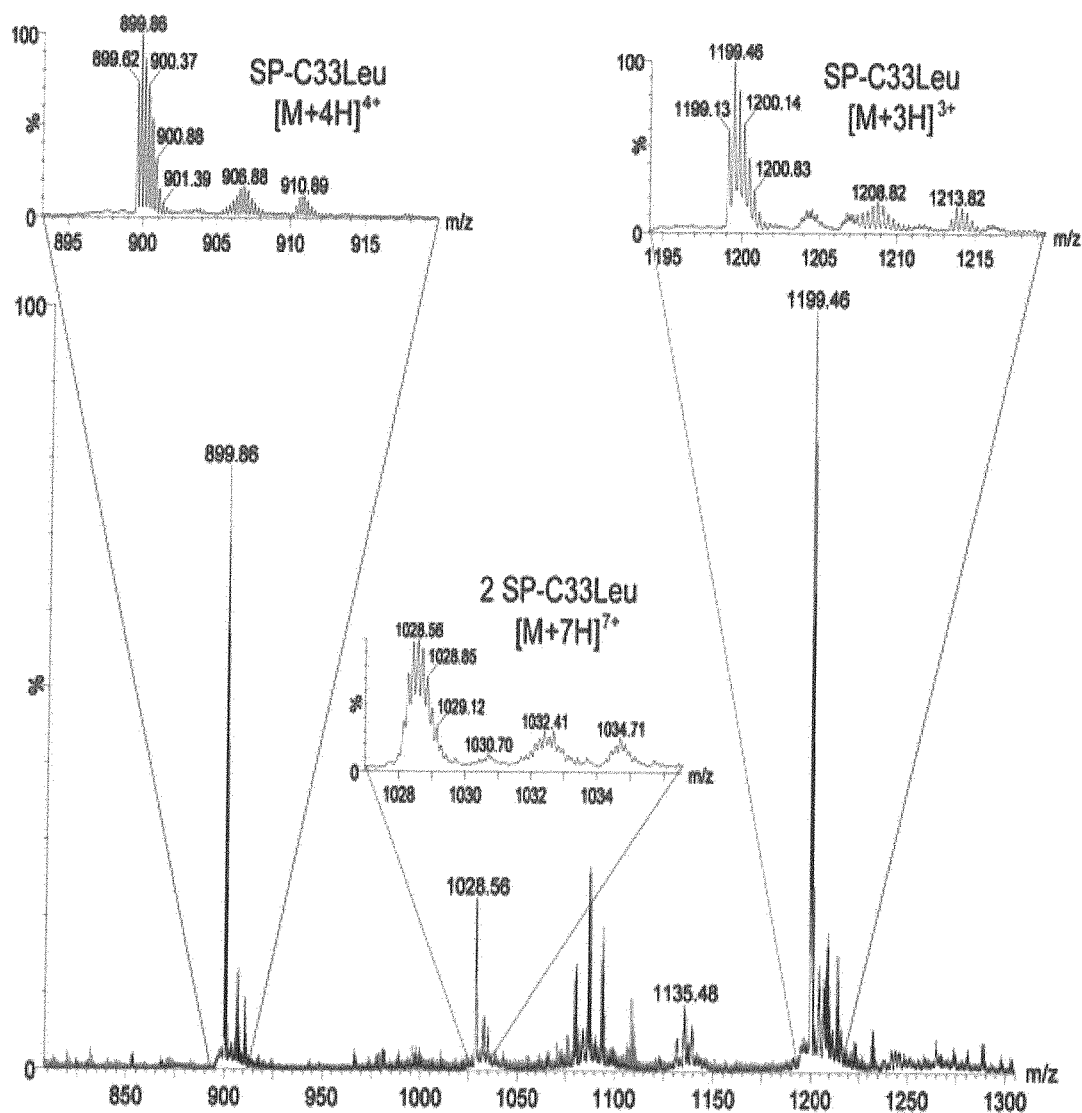
B
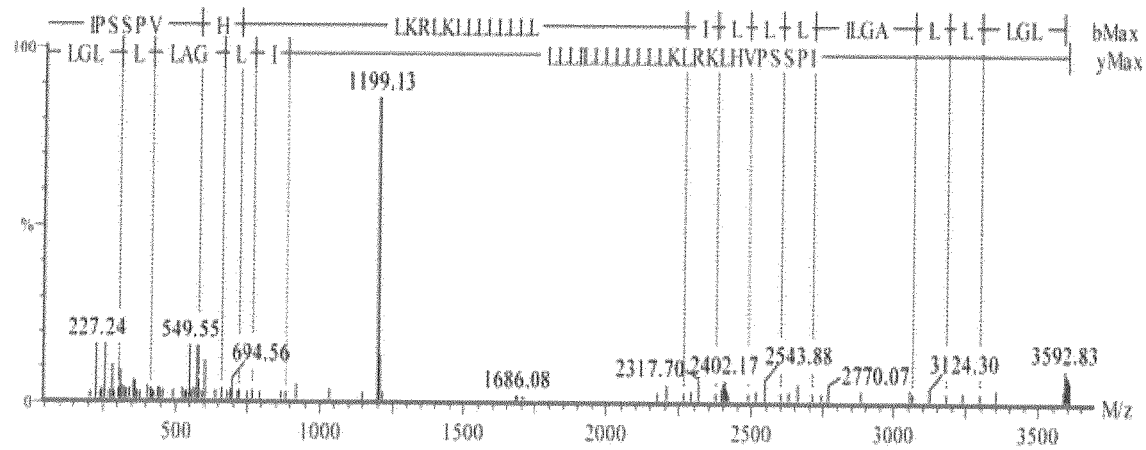
Fig 9

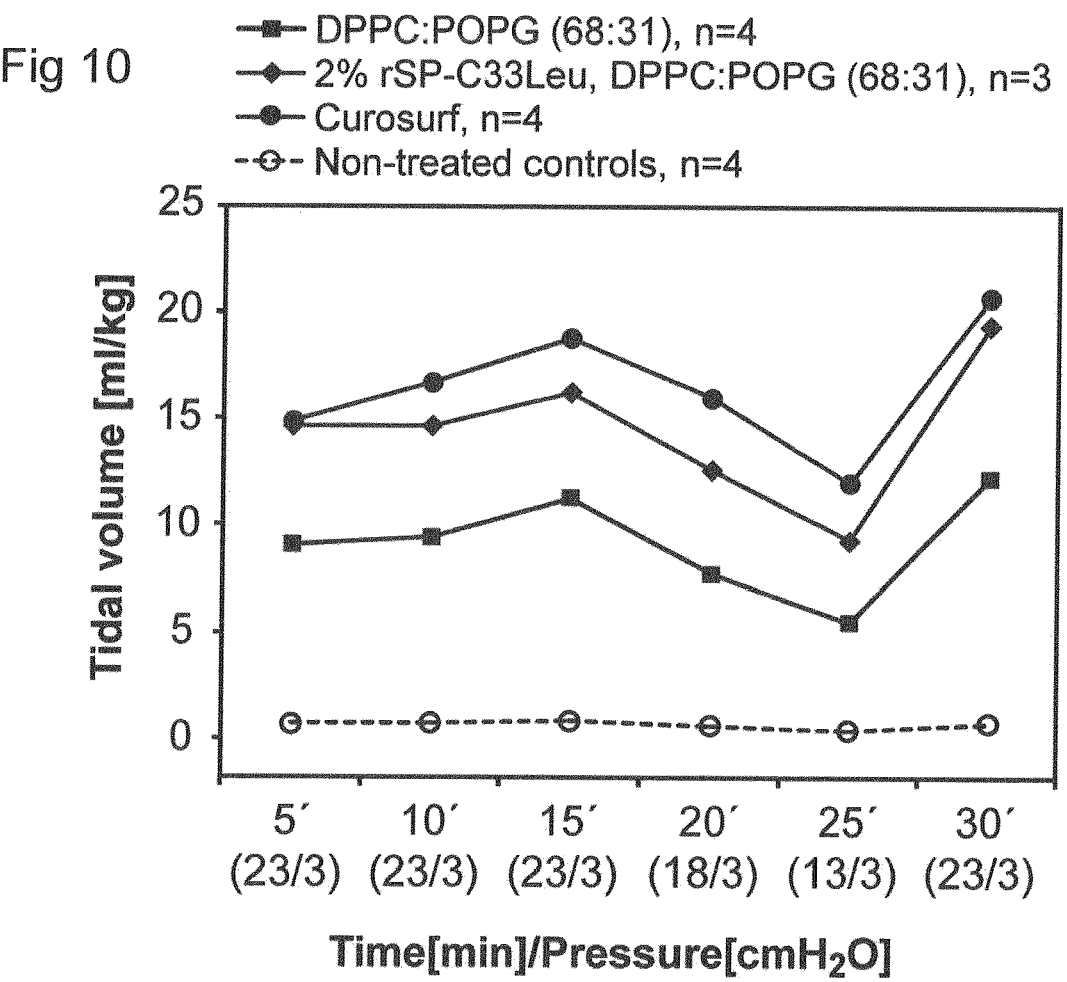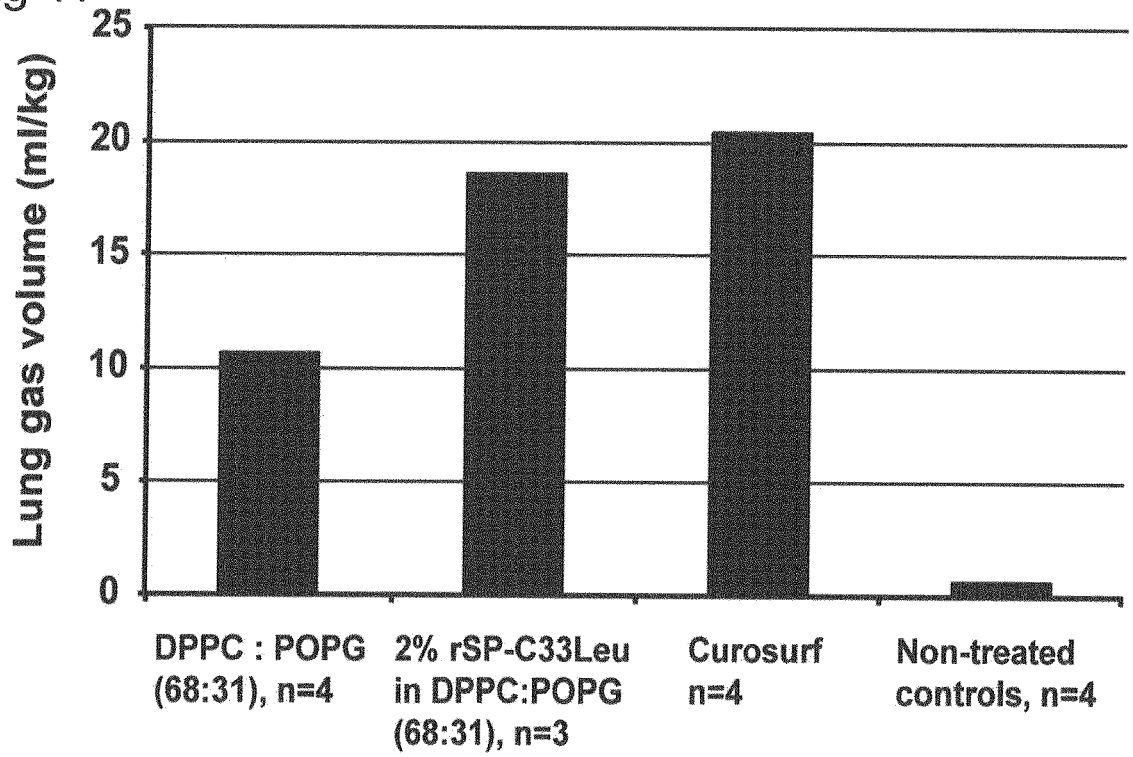

Fig 12
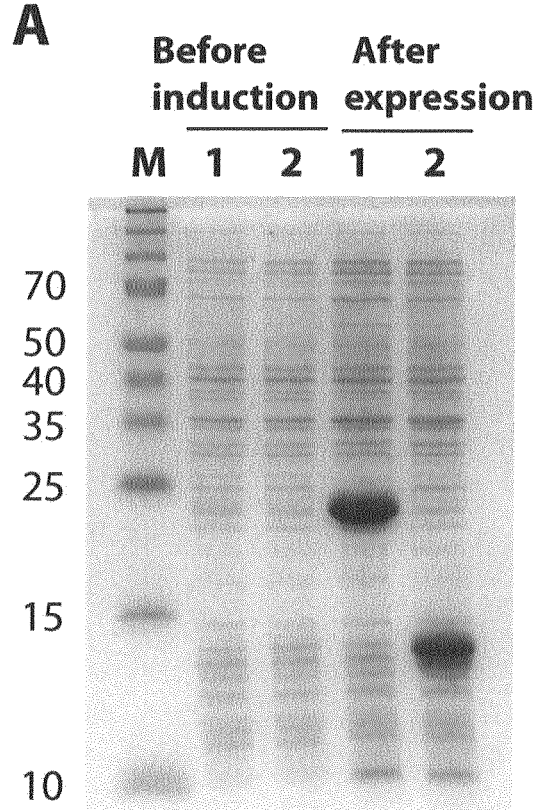
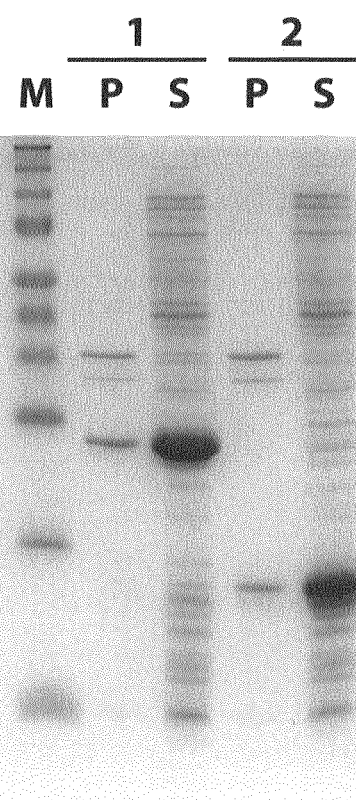
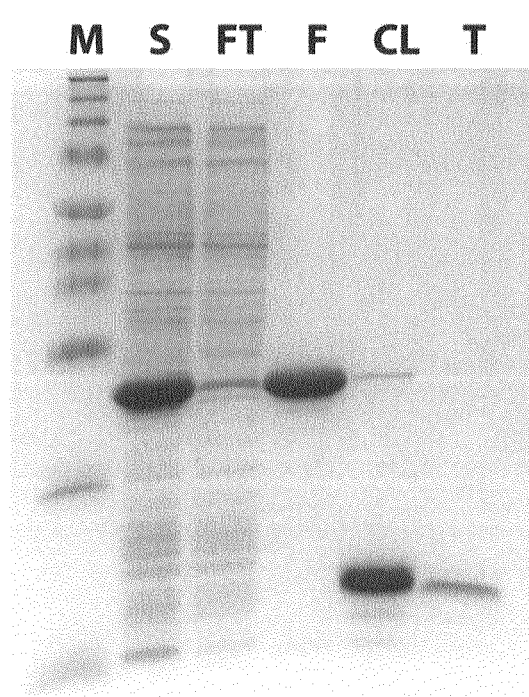

Fig 13
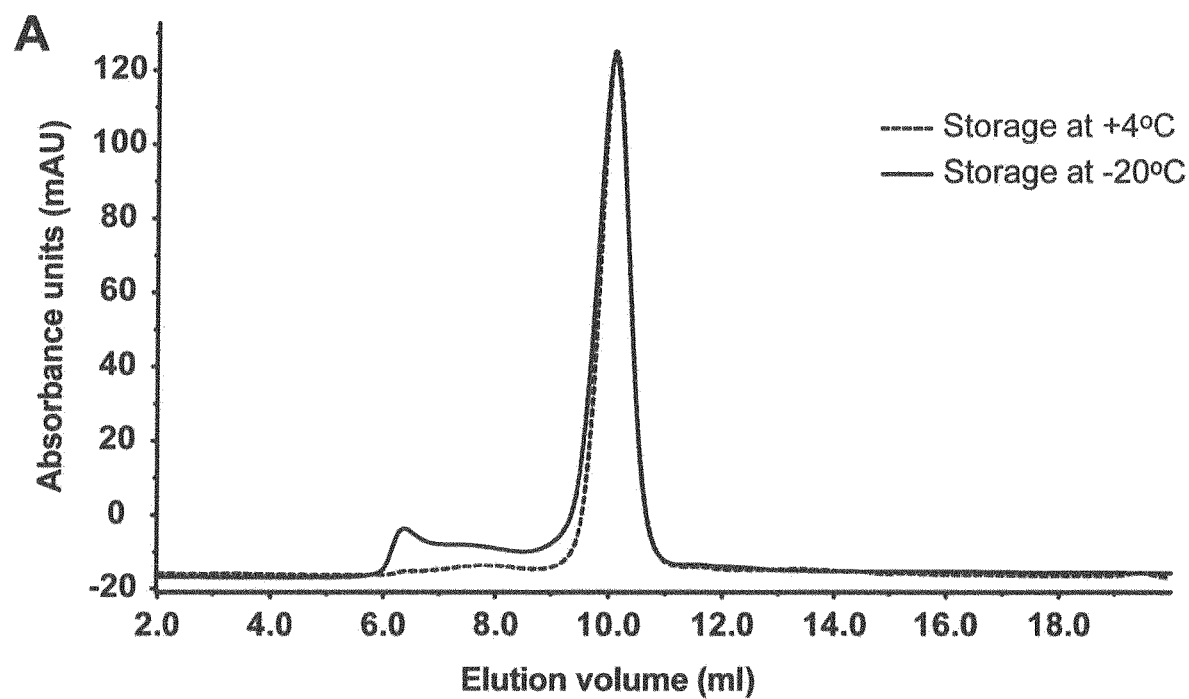
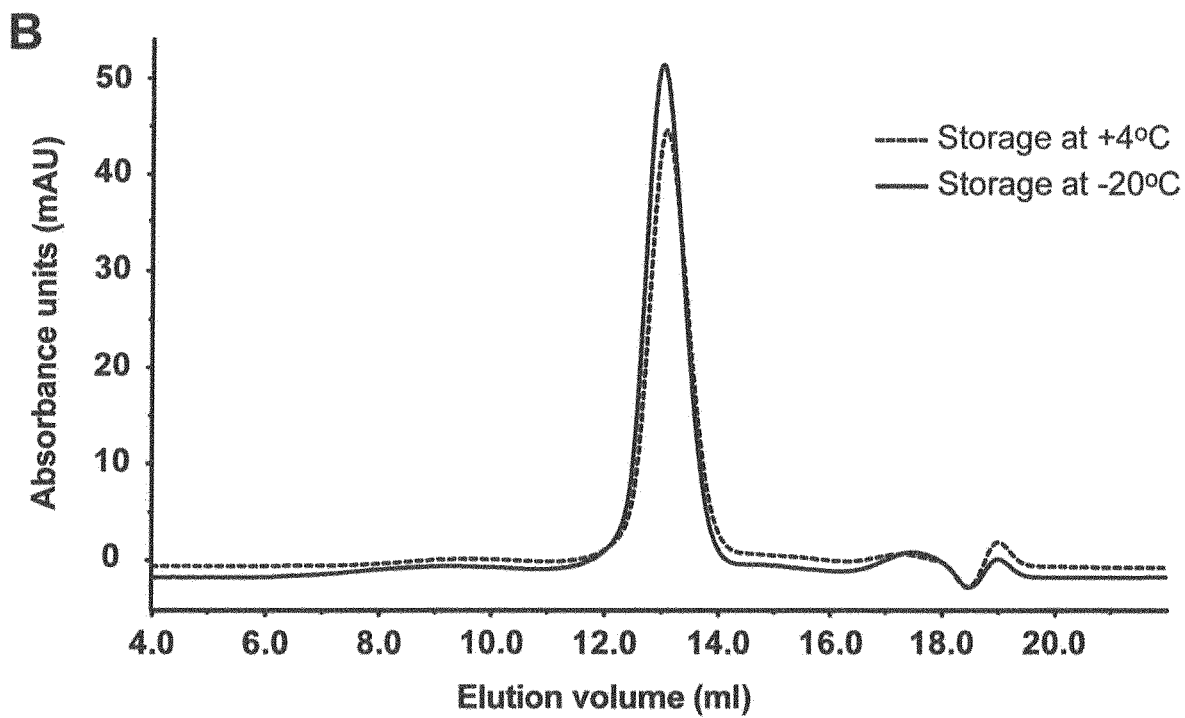

Fig 15
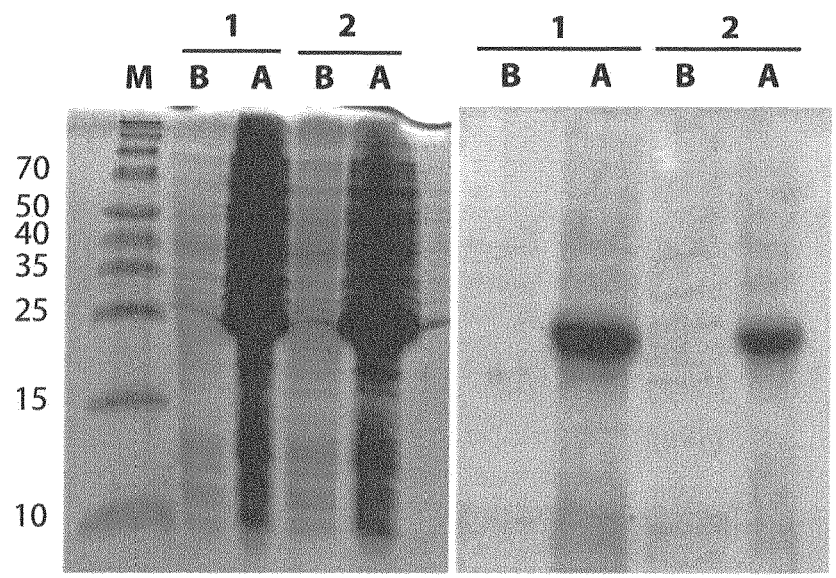
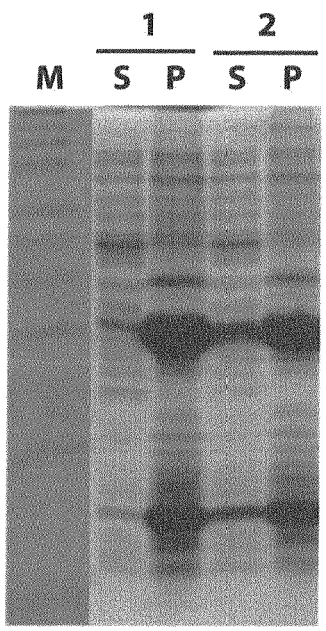
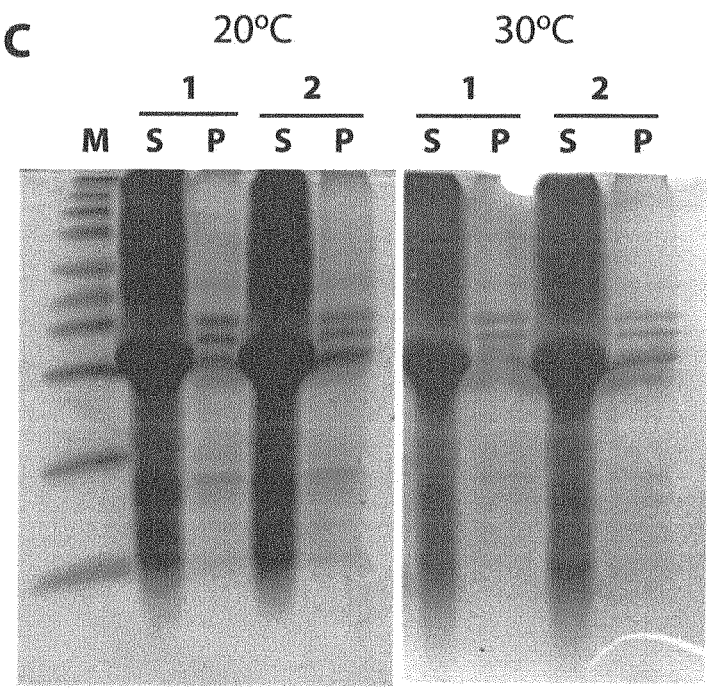

Fig 16
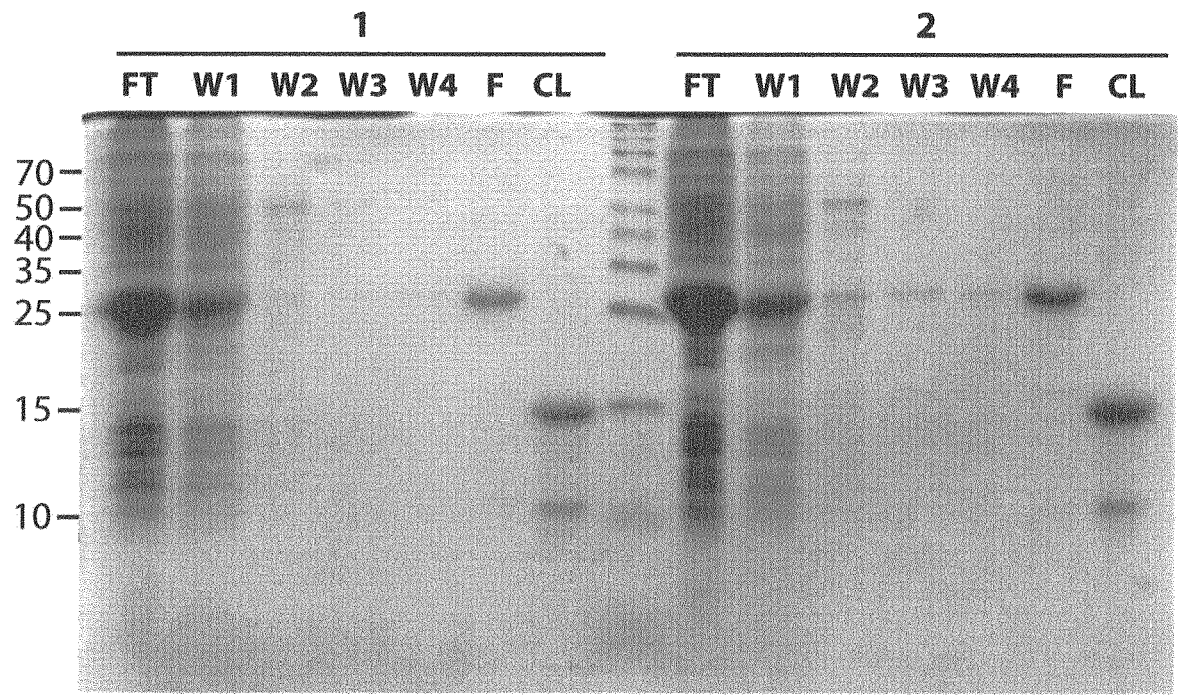
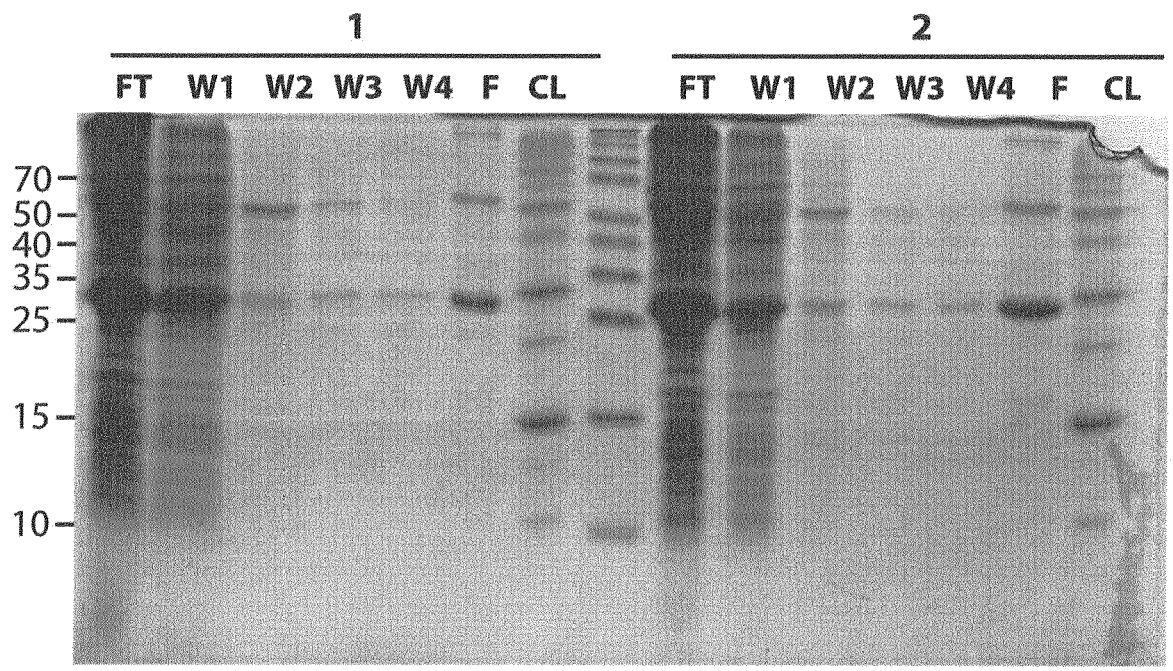

SEQUENCE LISTING

<160> NUMBER OF SEQ ID NOS: 108

<210> SEQ ID NO 1
<211> LENGTH: 137
<212> TYPE: PRT
<213> ORGANISM: Euprosthenops australis -continued
<220> FEATURE:
<221> NAME/KEY: VARIANT
<222> LOCATION: (40)..(40)
<223> OTHER INFORMATION: Arg (R)
<220> FEATURE:
<221> NAME/KEY: VARIANT
<222> LOCATION: (40)..(40)
<223> OTHER INFORMATION: His (H)
<220> FEATURE:
<221> NAME/KEY: MUTAGEN
<222> LOCATION: (40)..(40)
<220> FEATURE:
<221> NAME/KEY: VARIANT
<222> LOCATION: (65)..(65)
<223> OTHER INFORMATION: Glu (E)
<220> FEATURE:
<221> NAME/KEY: MUTAGEN
<222> LOCATION: (65)..(65)

<400> SEQUENCE: 1

Gly Ser Gly Asn Ser His Thr Thr Pro Trp Thr Asn Pro Gly Leu Ala
1               5                   10                  15

Glu Asn Phe Met Asn Ser Phe Met Gln Gly Leu Ser Ser Met Pro Gly
            20                  25                  30

Phe Thr Ala Ser Gln Leu Asp Lys Met Ser Thr Ile Ala Gln Ser Met
        35                  40                  45

Val Gln Ser Ile Gln Ser Leu Ala Ala Gln Gly Arg Thr Ser Pro Asn
    50                  55                  60

Asp Leu Gln Ala Leu Asn Met Ala Phe Ala Ser Ser Met Ala Glu Ile
65                  70                  75                  80

Ala Ala Ser Glu Glu Gly Gly Gly Ser Leu Ser Thr Lys Thr Ser Ser
                85                  90                  95

Ile Ala Ser Ala Met Ser Asn Ala Phe Leu Gln Thr Thr Gly Val Val
            100                 105                 110

Asn Gln Pro Phe Ile Asn Glu Ile Thr Gln Leu Val Ser Met Phe Ala
        115                 120                 125

Gln Ala Gly Met Asn Asp Val Ser Ala
    130                 135

<210> SEQ ID NO 2
<211> LENGTH: 133
<212> TYPE: PRT
<213> ORGANISM: Euprosthenops australis
<220> FEATURE:
<221> NAME/KEY: MUTAGEN
<222> LOCATION: (36)..(36)
<220> FEATURE:
<221> NAME/KEY: MUTAGEN
<222> LOCATION: (61)..(61)

<400> SEQUENCE: 2

Ser His Thr Thr Pro Trp Thr Asn Pro Gly Leu Ala Glu Asn Phe Met
1               5                   10                  15

Asn Ser Phe Met Gln Gly Leu Ser Ser Met Pro Gly Phe Thr Ala Ser
            20                  25                  30

Gln Leu Asp Lys Met Ser Thr Ile Ala Gln Ser Met Val Gln Ser Ile
        35                  40                  45

Gln Ser Leu Ala Ala Gln Gly Arg Thr Ser Pro Asn Asp Leu Gln Ala
    50                  55                  60

Leu Asn Met Ala Phe Ala Ser Ser Met Ala Glu Ile Ala Ala Ser Glu
65                  70                  75                  80

Glu Gly Gly Gly Ser Leu Ser Thr Lys Thr Ser Ser Ile Ala Ser Ala
                85                  90                  95

Met Ser Asn Ala Phe Leu Gln Thr Thr Gly Val Val Asn Gln Pro Phe
            100                 105                 110

Ile Asn Glu Ile Thr Gln Leu Val Ser Met Phe Ala Gln Ala Gly Met
        115                 120                 125

Asn Asp Val Ser Ala
    130

<210> SEQ ID NO 3
<211> LENGTH: 133
<212> TYPE: PRT
<213> ORGANISM: Euprosthenops australis
<220> FEATURE:
<221> NAME/KEY: MUTAGEN
<222> LOCATION: (36)..(36)
<220> FEATURE:
<221> NAME/KEY: MUTAGEN
<222> LOCATION: (61)..(61)

<400> SEQUENCE: 3

Ser His Thr Thr Pro Trp Thr Asn Pro Gly Leu Ala Glu Asn Phe Met
1               5                   10                  15

Asn Ser Phe Met Gln Gly Leu Ser Ser Met Pro Gly Phe Thr Ala Ser
            20                  25                  30

Gln Leu Asp Arg Met Ser Thr Ile Ala Gln Ser Met Val Gln Ser Ile
        35                  40                  45

Gln Ser Leu Ala Ala Gln Gly Arg Thr Ser Pro Asn Asp Leu Gln Ala
    50                  55                  60

Leu Asn Met Ala Phe Ala Ser Ser Met Ala Glu Ile Ala Ala Ser Glu
65                  70                  75                  80

Glu Gly Gly Gly Ser Leu Ser Thr Lys Thr Ser Ser Ile Ala Ser Ala
                85                  90                  95

Met Ser Asn Ala Phe Leu Gln Thr Thr Gly Val Val Asn Gln Pro Phe
            100                 105                 110

Ile Asn Glu Ile Thr Gln Leu Val Ser Met Phe Ala Gln Ala Gly Met
        115                 120                 125

Asn Asp Val Ser Ala
    130

<210> SEQ ID NO 4
<211> LENGTH: 133
<212> TYPE: PRT
<213> ORGANISM: Euprosthenops australis
<220> FEATURE:
<221> NAME/KEY: MUTAGEN
<222> LOCATION: (36)..(36)
<220> FEATURE:
<221> NAME/KEY: MUTAGEN
<222> LOCATION: (61)..(61)

<400> SEQUENCE: 4

Ser His Thr Thr Pro Trp Thr Asn Pro Gly Leu Ala Glu Asn Phe Met
1               5                   10                  15

Asn Ser Phe Met Gln Gly Leu Ser Ser Met Pro Gly Phe Thr Ala Ser
            20                  25                  30

Gln Leu Asp His Met Ser Thr Ile Ala Gln Ser Met Val Gln Ser Ile
        35                  40                  45

Gln Ser Leu Ala Ala Gln Gly Arg Thr Ser Pro Asn Asp Leu Gln Ala
    50                  55                  60

Leu Asn Met Ala Phe Ala Ser Ser Met Ala Glu Ile Ala Ala Ser Glu
65                  70                  75                  80

```
Glu Gly Gly Gly Ser Leu Ser Thr Lys Thr Ser Ser Ile Ala Ser Ala
            85                  90                  95

Met Ser Asn Ala Phe Leu Gln Thr Thr Gly Val Val Asn Gln Pro Phe
            100                 105                 110

Ile Asn Glu Ile Thr Gln Leu Val Ser Met Phe Ala Gln Ala Gly Met
        115                 120                 125

Asn Asp Val Ser Ala
    130

<210> SEQ ID NO 5
<211> LENGTH: 133
<212> TYPE: PRT
<213> ORGANISM: Euprosthenops australis
<220> FEATURE:
<221> NAME/KEY: MUTAGEN
<222> LOCATION: (36)..(36)
<220> FEATURE:
<221> NAME/KEY: MUTAGEN
<222> LOCATION: (61)..(61)

<400> SEQUENCE: 5

Ser His Thr Thr Pro Trp Thr Asn Pro Gly Leu Ala Glu Asn Phe Met
1               5                   10                  15

Asn Ser Phe Met Gln Gly Leu Ser Ser Met Pro Gly Phe Thr Ala Ser
            20                  25                  30

Gln Leu Asp Lys Met Ser Thr Ile Ala Gln Ser Met Val Gln Ser Ile
        35                  40                  45

Gln Ser Leu Ala Ala Gln Gly Arg Thr Ser Pro Asn Glu Leu Gln Ala
    50                  55                  60

Leu Asn Met Ala Phe Ala Ser Ser Met Ala Glu Ile Ala Ala Ser Glu
65                  70                  75                  80

Glu Gly Gly Gly Ser Leu Ser Thr Lys Thr Ser Ser Ile Ala Ser Ala
            85                  90                  95

Met Ser Asn Ala Phe Leu Gln Thr Thr Gly Val Val Asn Gln Pro Phe
            100                 105                 110

Ile Asn Glu Ile Thr Gln Leu Val Ser Met Phe Ala Gln Ala Gly Met
        115                 120                 125

Asn Asp Val Ser Ala
    130

<210> SEQ ID NO 6
<211> LENGTH: 133
<212> TYPE: PRT
<213> ORGANISM: Euprosthenops australis
<220> FEATURE:
<221> NAME/KEY: MUTAGEN
<222> LOCATION: (36)..(36)
<220> FEATURE:
<221> NAME/KEY: MUTAGEN
<222> LOCATION: (61)..(61)

<400> SEQUENCE: 6

Ser His Thr Thr Pro Trp Thr Asn Pro Gly Leu Ala Glu Asn Phe Met
1               5                   10                  15

Asn Ser Phe Met Gln Gly Leu Ser Ser Met Pro Gly Phe Thr Ala Ser
            20                  25                  30

Gln Leu Asp Arg Met Ser Thr Ile Ala Gln Ser Met Val Gln Ser Ile
        35                  40                  45

Gln Ser Leu Ala Ala Gln Gly Arg Thr Ser Pro Asn Glu Leu Gln Ala
    50                  55                  60
```

```
Leu Asn Met Ala Phe Ala Ser Ser Met Ala Glu Ile Ala Ser Glu
 65                  70                  75                  80

Glu Gly Gly Gly Ser Leu Ser Thr Lys Thr Ser Ile Ala Ser Ala
             85                  90                  95

Met Ser Asn Ala Phe Leu Gln Thr Thr Gly Val Val Asn Gln Pro Phe
            100                 105                 110

Ile Asn Glu Ile Thr Gln Leu Val Ser Met Phe Ala Gln Ala Gly Met
        115                 120                 125

Asn Asp Val Ser Ala
        130

<210> SEQ ID NO 7
<211> LENGTH: 133
<212> TYPE: PRT
<213> ORGANISM: Euprosthenops australis
<220> FEATURE:
<221> NAME/KEY: MUTAGEN
<222> LOCATION: (36)..(36)
<220> FEATURE:
<221> NAME/KEY: MUTAGEN
<222> LOCATION: (61)..(61)

<400> SEQUENCE: 7

Ser His Thr Thr Pro Trp Thr Asn Pro Gly Leu Ala Glu Asn Phe Met
 1               5                  10                  15

Asn Ser Phe Met Gln Gly Leu Ser Ser Met Pro Gly Phe Thr Ala Ser
             20                  25                  30

Gln Leu Asp His Met Ser Thr Ile Ala Gln Ser Met Val Gln Ser Ile
         35                  40                  45

Gln Ser Leu Ala Ala Gln Gly Arg Thr Ser Pro Asn Glu Leu Gln Ala
     50                  55                  60

Leu Asn Met Ala Phe Ala Ser Ser Met Ala Glu Ile Ala Ser Glu
 65                  70                  75                  80

Glu Gly Gly Gly Ser Leu Ser Thr Lys Thr Ser Ile Ala Ser Ala
             85                  90                  95

Met Ser Asn Ala Phe Leu Gln Thr Thr Gly Val Val Asn Gln Pro Phe
            100                 105                 110

Ile Asn Glu Ile Thr Gln Leu Val Ser Met Phe Ala Gln Ala Gly Met
        115                 120                 125

Asn Asp Val Ser Ala
        130

<210> SEQ ID NO 8
<211> LENGTH: 399
<212> TYPE: DNA
<213> ORGANISM: Euprosthenops australis

<400> SEQUENCE: 8
tcacacacta caccatggac aaacccagga ctcgcagaaa acttcatgaa cagtttcatg      60
caaggcctga gctcgatgcc aggtttcacg gcaagccaat tggataagat gtcaaccatc    120
gcacaatcca tggtacagtc aatacaatcc ttggcggcac aaggcaggac atcaccgaat    180
gacctgcagg cccttaacat ggcttttgca tcttcgatgg cagaaatcgc ggcatccgaa    240
gaaggagggg gaagcctttc accaaaaact agctctatag ccagtgcaat gtccaacgcg    300
tttctgcaaa caactggagt ggtaaaccaa ccgttcataa atgaaataac tcagctcgtt    360
agcatgtttg ctcaagcagg tatgaatgat gtcagtgct                           399
```

```
<210> SEQ ID NO 9
<211> LENGTH: 137
<212> TYPE: PRT
<213> ORGANISM: Euprosthenops australis
<220> FEATURE:
<221> NAME/KEY: VARIANT
<222> LOCATION: (6)..(6)
<223> OTHER INFORMATION: deletion (deltaHis)

<400> SEQUENCE: 9

Gly Ser Gly Asn Ser His Thr Thr Pro Trp Thr Asn Pro Gly Leu Ala
1               5                   10                  15

Glu Asn Phe Met Asn Ser Phe Met Gln Gly Leu Ser Ser Met Pro Gly
            20                  25                  30

Phe Thr Ala Ser Gln Leu Asp Asp Met Ser Thr Ile Ala Gln Ser Met
        35                  40                  45

Val Gln Ser Ile Gln Ser Leu Ala Ala Gln Gly Arg Thr Ser Pro Asn
    50                  55                  60

Lys Leu Gln Ala Leu Asn Met Ala Phe Ala Ser Ser Met Ala Glu Ile
65                  70                  75                  80

Ala Ala Ser Glu Glu Gly Gly Gly Ser Leu Ser Thr Lys Thr Ser Ser
                85                  90                  95

Ile Ala Ser Ala Met Ser Asn Ala Phe Leu Gln Thr Thr Gly Val Val
            100                 105                 110

Asn Gln Pro Phe Ile Asn Glu Ile Thr Gln Leu Val Ser Met Phe Ala
        115                 120                 125

Gln Ala Gly Met Asn Asp Val Ser Ala
    130                 135

<210> SEQ ID NO 10
<211> LENGTH: 131
<212> TYPE: PRT
<213> ORGANISM: Artificial Sequence
<220> FEATURE:
<223> OTHER INFORMATION: Consensus sequence derived from spidroin NT
      fragments
<220> FEATURE:
<221> NAME/KEY: VARIANT
<222> LOCATION: (20)..(20)
<223> OTHER INFORMATION: Leu
<220> FEATURE:
<221> NAME/KEY: VARIANT
<222> LOCATION: (42)..(42)
<223> OTHER INFORMATION: Asn
<220> FEATURE:
<221> NAME/KEY: VARIANT
<222> LOCATION: (42)..(42)
<223> OTHER INFORMATION: Gln
<220> FEATURE:
<221> NAME/KEY: VARIANT
<222> LOCATION: (50)..(50)
<223> OTHER INFORMATION: Ser
<220> FEATURE:
<221> NAME/KEY: VARIANT
<222> LOCATION: (50)..(50)
<223> OTHER INFORMATION: Lys
<220> FEATURE:
<221> NAME/KEY: VARIANT
<222> LOCATION: (56)..(56)
<223> OTHER INFORMATION: Arg
<220> FEATURE:
<221> NAME/KEY: VARIANT
<222> LOCATION: (84)..(84)
<223> OTHER INFORMATION: Leu
<220> FEATURE:
<221> NAME/KEY: VARIANT
<222> LOCATION: (114)..(114)
<223> OTHER INFORMATION: Ser
```

```
<220> FEATURE:
<221> NAME/KEY: VARIANT
<222> LOCATION: (121)..(121)
<223> OTHER INFORMATION: Asn
<220> FEATURE:
<221> NAME/KEY: VARIANT
<222> LOCATION: (123)..(123)
<223> OTHER INFORMATION: Leu
<220> FEATURE:
<221> NAME/KEY: VARIANT
<222> LOCATION: (124)..(124)
<223> OTHER INFORMATION: Ser

<400> SEQUENCE: 10

Gln Ala Asn Thr Pro Trp Ser Ser Pro Asn Leu Ala Asp Ala Phe Ile
1               5                   10                  15

Asn Ser Phe Met Ser Ala Ala Ser Ser Gly Ala Phe Ser Ala Asp
            20                  25                  30

Gln Leu Asp Asp Met Ser Thr Ile Gly Asp Thr Leu Met Ser Ala Met
        35                  40                  45

Asp Asn Met Gly Arg Ser Gly Lys Ser Thr Lys Ser Lys Leu Gln Ala
    50                  55                  60

Leu Asn Met Ala Phe Ala Ser Ser Met Ala Glu Ile Ala Ala Ala Glu
65                  70                  75                  80

Ser Gly Gly Gly Ser Val Gly Val Lys Thr Asn Ala Ile Ser Asp Ala
                85                  90                  95

Leu Ser Ser Ala Phe Tyr Gln Thr Thr Gly Ser Val Asn Pro Gln Phe
            100                 105                 110

Val Asn Glu Ile Arg Ser Leu Ile Gly Met Phe Ala Gln Ala Ser Ala
        115                 120                 125

Asn Glu Val
    130

<210> SEQ ID NO 11
<211> LENGTH: 133
<212> TYPE: PRT
<213> ORGANISM: Euprosthenops australis

<400> SEQUENCE: 11

Ser His Thr Thr Pro Trp Thr Asn Pro Gly Leu Ala Glu Asn Phe Met
1               5                   10                  15

Asn Ser Phe Met Gln Gly Leu Ser Ser Met Pro Gly Phe Thr Ala Ser
            20                  25                  30

Gln Leu Asp Asp Met Ser Thr Ile Ala Gln Ser Met Val Gln Ser Ile
        35                  40                  45

Gln Ser Leu Ala Ala Gln Gly Arg Thr Ser Pro Asn Lys Leu Gln Ala
    50                  55                  60

Leu Asn Met Ala Phe Ala Ser Ser Met Ala Glu Ile Ala Ala Ser Glu
65                  70                  75                  80

Glu Gly Gly Gly Ser Leu Ser Thr Lys Thr Ser Ser Ile Ala Ser Ala
                85                  90                  95

Met Ser Asn Ala Phe Leu Gln Thr Thr Gly Val Val Asn Gln Pro Phe
            100                 105                 110

Ile Asn Glu Ile Thr Gln Leu Val Ser Met Phe Ala Gln Ala Gly Met
        115                 120                 125

Asn Asp Val Ser Ala
    130

<210> SEQ ID NO 12
```

```
<211> LENGTH: 399
<212> TYPE: DNA
<213> ORGANISM: Euprosthenops australis

<400> SEQUENCE: 12
tcacacacta caccatggac aaacccagga ctcgcagaaa acttcatgaa cagtttcatg    60
caaggcctga gctcgatgcc aggtttcacg gcaagccaat ggatgatat gtcaaccatc    120 gcacaatcca tggtacagtc aatacaatcc ttggcggcac aaggcaggac atcaccgaat   180
aagctgcagg cccttaacat ggcttttgca tcttcgatgg cagaaatcgc ggcatccgaa   240
gaaggagggg gaagccttc caccaaaact agctctatag ccagtgcaat gtccaacgcg    300
tttctgcaaa caactggagt ggtaaaccaa ccgttcataa atgaaataac tcagctcgtt   360
agcatgtttg ctcaagcagg tatgaatgat gtcagtgct                          399

<210> SEQ ID NO 13
<211> LENGTH: 131
<212> TYPE: PRT
<213> ORGANISM: Euprosthenops australis

<400> SEQUENCE: 13

Ser His Thr Thr Pro Trp Thr Asn Pro Gly Leu Ala Glu Asn Phe Met
1               5                   10                  15

Asn Ser Phe Met Gln Gly Leu Ser Ser Met Pro Gly Phe Thr Ala Ser
            20                  25                  30

Gln Leu Asp Asp Met Ser Thr Ile Ala Gln Ser Met Val Gln Ser Ile
        35                  40                  45

Gln Ser Leu Ala Ala Gln Gly Arg Thr Ser Pro Asn Lys Leu Gln Ala
    50                  55                  60

Leu Asn Met Ala Phe Ala Ser Ser Met Ala Glu Ile Ala Ala Ser Glu
65                  70                  75                  80

Glu Gly Gly Gly Ser Leu Ser Thr Lys Thr Ser Ser Ile Ala Ser Ala
                85                  90                  95

Met Ser Asn Ala Phe Leu Gln Thr Thr Gly Val Val Asn Gln Pro Phe
            100                 105                 110

Ile Asn Glu Ile Thr Gln Leu Val Ser Met Phe Ala Gln Ala Gly Met
        115                 120                 125

Asn Asp Val
    130

<210> SEQ ID NO 14
<211> LENGTH: 127
<212> TYPE: PRT
<213> ORGANISM: Latrodectus geometricus

<400> SEQUENCE: 14

Gln Ala Asn Thr Pro Trp Ser Ser Lys Gln Asn Ala Asp Ala Phe Ile
1               5                   10                  15

Ser Ala Phe Met Thr Ala Ala Ser Gln Ser Gly Ala Phe Ser Ser Asp
            20                  25                  30

Gln Ile Asp Asp Met Ser Val Ile Ser Asn Thr Leu Met Ala Ala Met
        35                  40                  45

Asp Asn Met Gly Gly Arg Ile Thr Pro Ser Lys Leu Gln Ala Leu Asp
    50                  55                  60

Met Ala Phe Ala Ser Ser Val Ala Glu Ile Ala Ala Val Glu Gly Gln
65                  70                  75                  80

Asn Ile Gly Val Thr Thr Asn Ala Ile Ser Asp Ala Leu Thr Ser Ala
```

-continued

```
                85                  90                  95
Phe Tyr Gln Thr Thr Gly Val Val Asn Asn Lys Phe Ile Ser Glu Ile
            100                 105                 110
Arg Ser Leu Ile Asn Met Phe Ala Gln Ala Ser Ala Asn Asp Val
            115                 120                 125

<210> SEQ ID NO 15
<211> LENGTH: 127
<212> TYPE: PRT
<213> ORGANISM: Latrodectus hesperus

<400> SEQUENCE: 15

Gln Ala Asn Thr Pro Trp Ser Ser Lys Ala Asn Ala Asp Ala Phe Ile
1               5                   10                  15
Asn Ser Phe Ile Ser Ala Ala Ser Asn Thr Gly Ser Phe Ser Gln Asp
                20                  25                  30
Gln Met Glu Asp Met Ser Leu Ile Gly Asn Thr Leu Met Ala Ala Met
            35                  40                  45
Asp Asn Met Gly Gly Arg Ile Thr Pro Ser Lys Leu Gln Ala Leu Asp
        50                  55                  60
Met Ala Phe Ala Ser Ser Val Ala Glu Ile Ala Ala Ser Glu Gly Gly
65                  70                  75                  80
Asp Leu Gly Val Thr Thr Asn Ala Ile Ala Asp Ala Leu Thr Ser Ala
                85                  90                  95
Phe Tyr Gln Thr Thr Gly Val Val Asn Ser Arg Phe Ile Ser Glu Ile
            100                 105                 110
Arg Ser Leu Ile Gly Met Phe Ala Gln Ala Ser Ala Asn Asp Val
            115                 120                 125

<210> SEQ ID NO 16
<211> LENGTH: 130
<212> TYPE: PRT
<213> ORGANISM: Nephila clavipes

<400> SEQUENCE: 16

Gln Asn Thr Pro Trp Ser Ser Thr Glu Leu Ala Asp Ala Phe Ile Asn
1               5                   10                  15
Ala Phe Met Asn Glu Ala Gly Arg Thr Gly Ala Phe Thr Ala Asp Gln
                20                  25                  30
Leu Asp Asp Met Ser Thr Ile Gly Asp Thr Ile Lys Thr Ala Met Asp
            35                  40                  45
Lys Met Ala Arg Ser Asn Lys Ser Ser Lys Gly Lys Leu Gln Ala Leu
        50                  55                  60
Asn Met Ala Phe Ala Ser Ser Met Ala Glu Ile Ala Ala Val Glu Gln
65                  70                  75                  80
Gly Gly Leu Ser Val Asp Ala Lys Thr Asn Ala Ile Ala Asp Ser Leu
                85                  90                  95
Asn Ser Ala Phe Tyr Gln Thr Thr Gly Ala Ala Asn Pro Gln Phe Val
            100                 105                 110
Asn Glu Ile Arg Ser Leu Ile Asn Met Phe Ala Gln Ser Ser Ala Asn
            115                 120                 125
Glu Val
    130

<210> SEQ ID NO 17
<211> LENGTH: 131
<212> TYPE: PRT
```

<213> ORGANISM: Argiope trifasciata

<400> SEQUENCE: 17

```
Gln Gly Ala Thr Pro Trp Glu Asn Ser Gln Leu Ala Glu Ser Phe Ile
1               5                   10                  15

Ser Arg Phe Leu Arg Phe Ile Gly Gln Ser Gly Ala Phe Ser Pro Asn
            20                  25                  30

Gln Leu Asp Asp Met Ser Ser Ile Gly Asp Thr Leu Lys Thr Ala Ile
        35                  40                  45

Glu Lys Met Ala Gln Ser Arg Lys Ser Ser Lys Ser Lys Leu Gln Ala
50                  55                  60

Leu Asn Met Ala Phe Ala Ser Ser Met Ala Glu Ile Ala Val Ala Glu
65                  70                  75                  80

Gln Gly Gly Leu Ser Leu Glu Ala Lys Thr Asn Ala Ile Ala Ser Ala
                85                  90                  95

Leu Ser Ala Ala Phe Leu Glu Thr Thr Gly Tyr Val Asn Gln Gln Phe
            100                 105                 110

Val Asn Glu Ile Lys Thr Leu Ile Phe Met Ile Ala Gln Ala Ser Ser
        115                 120                 125

Asn Glu Ile
    130
```

<210> SEQ ID NO 18
<211> LENGTH: 124
<212> TYPE: PRT
<213> ORGANISM: Latrodectus geometricus

<400> SEQUENCE: 18

```
Leu Arg Trp Ser Ser Lys Asp Asn Ala Asp Arg Phe Ile Asn Ala Phe
1               5                   10                  15

Leu Gln Ala Ala Ser Asn Ser Gly Ala Phe Ser Ser Asp Gln Val Asp
            20                  25                  30

Asp Met Ser Val Ile Gly Asn Thr Leu Met Thr Ala Met Asp Asn Met
        35                  40                  45

Gly Gly Arg Ile Thr Pro Ser Lys Leu Gln Ala Leu Asp Met Ala Phe
50                  55                  60

Ala Ser Ser Val Ala Glu Ile Ala Val Ala Asp Gly Gln Asn Val Gly
65                  70                  75                  80

Gly Ala Thr Asn Ala Ile Ser Asn Ala Leu Arg Ser Ala Phe Tyr Gln
                85                  90                  95

Thr Thr Gly Val Val Asn Asn Gln Phe Ile Ser Glu Ile Ser Asn Leu
            100                 105                 110

Ile Asn Met Phe Ala Gln Val Ser Ala Asn Glu Val
        115                 120
```

<210> SEQ ID NO 19
<211> LENGTH: 127
<212> TYPE: PRT
<213> ORGANISM: Latrodectus hesperus

<400> SEQUENCE: 19

```
Gln Ala Asn Thr Pro Trp Ser Ser Lys Glu Asn Ala Asp Ala Phe Ile
1               5                   10                  15

Gly Ala Phe Met Asn Ala Ala Ser Gln Ser Gly Ala Phe Ser Ser Asp
            20                  25                  30

Gln Ile Asp Asp Met Ser Val Ile Ser Asn Thr Leu Met Ala Ala Met
        35                  40                  45
```

```
Asp Asn Met Gly Gly Arg Ile Thr Gln Ser Lys Leu Gln Ala Leu Asp
         50                  55                  60

Met Ala Phe Ala Ser Ser Val Ala Glu Ile Ala Val Ala Asp Gly Gln
 65                  70                  75                  80

Asn Val Gly Ala Ala Thr Asn Ala Ile Ser Asp Ala Leu Arg Ser Ala
                 85                  90                  95

Phe Tyr Gln Thr Thr Gly Val Val Asn Asn Gln Phe Ile Thr Gly Ile
                100                 105                 110

Ser Ser Leu Ile Gly Met Phe Ala Gln Val Ser Gly Asn Glu Val
                115                 120                 125

<210> SEQ ID NO 20
<211> LENGTH: 131
<212> TYPE: PRT
<213> ORGANISM: Nephila inaurata madagascariensis

<400> SEQUENCE: 20

Gln Ala Asn Thr Pro Trp Ser Asp Thr Ala Thr Ala Asp Ala Phe Ile
  1               5                  10                  15

Gln Asn Phe Leu Gly Ala Val Ser Gly Ser Gly Ala Phe Thr Pro Asp
                 20                  25                  30

Gln Leu Asp Asp Met Ser Thr Val Gly Asp Thr Ile Met Ser Ala Met
             35                  40                  45

Asp Lys Met Ala Arg Ser Asn Lys Ser Ser Lys Ser Lys Leu Gln Ala
         50                  55                  60

Leu Asn Met Ala Phe Ala Ser Ser Met Ala Glu Ile Ala Ala Val Glu
 65                  70                  75                  80

Gln Gly Gly Gln Ser Met Asp Val Lys Thr Asn Ala Ile Ala Asn Ala
                 85                  90                  95

Leu Asp Ser Ala Phe Tyr Met Thr Thr Gly Ser Thr Asn Gln Gln Phe
                100                 105                 110

Val Asn Glu Met Arg Ser Leu Ile Asn Met Leu Ser Ala Ala Ala Val
                115                 120                 125

Asn Glu Val
    130

<210> SEQ ID NO 21
<211> LENGTH: 131
<212> TYPE: PRT
<213> ORGANISM: Nephila clavipes

<400> SEQUENCE: 21

Gln Ala Arg Ser Pro Trp Ser Asp Thr Ala Thr Ala Asp Ala Phe Ile
  1               5                  10                  15

Gln Asn Phe Leu Ala Ala Val Ser Gly Ser Gly Ala Phe Thr Ser Asp
                 20                  25                  30

Gln Leu Asp Asp Met Ser Thr Ile Gly Asp Thr Ile Met Ser Ala Met
             35                  40                  45

Asp Lys Met Ala Arg Ser Asn Lys Ser Ser Gln His Lys Leu Gln Ala
         50                  55                  60

Leu Asn Met Ala Phe Ala Ser Ser Met Ala Glu Ile Ala Ala Val Glu
 65                  70                  75                  80

Gln Gly Gly Met Ser Met Ala Val Lys Thr Asn Ala Ile Val Asp Gly
                 85                  90                  95

Leu Asn Ser Ala Phe Tyr Met Thr Thr Gly Ala Ala Asn Pro Gln Phe
                100                 105                 110
```

```
Val Asn Glu Met Arg Ser Leu Ile Ser Met Ile Ser Ala Ala Ser Ala
        115                 120                 125
Asn Glu Val
    130

<210> SEQ ID NO 22
<211> LENGTH: 129
<212> TYPE: PRT
<213> ORGANISM: Argiope bruennichi

<400> SEQUENCE: 22

Ala Val Pro Ser Val Phe Ser Ser Pro Asn Leu Ala Ser Gly Phe Leu
1               5                   10                  15

Gln Cys Leu Thr Phe Gly Ile Gly Asn Ser Pro Ala Phe Pro Thr Gln
            20                  25                  30

Glu Gln Gln Asp Leu Asp Ala Ile Ala Gln Val Ile Leu Asn Ala Val
        35                  40                  45

Ser Ser Asn Thr Gly Ala Thr Ala Ser Ala Arg Ala Gln Ala Leu Ser
50                  55                  60

Thr Ala Leu Ala Ser Ser Leu Thr Asp Leu Leu Ile Ala Glu Ser Ala
65                  70                  75                  80

Glu Ser Asn Tyr Ser Asn Gln Leu Ser Glu Leu Thr Gly Ile Leu Ser
                85                  90                  95

Asp Cys Phe Ile Gln Thr Thr Gly Ser Asp Asn Pro Ala Phe Val Ser
            100                 105                 110

Arg Ile Gln Ser Leu Ile Ser Val Leu Ser Gln Asn Ala Asp Thr Asn
        115                 120                 125

Ile

<210> SEQ ID NO 23
<211> LENGTH: 129
<212> TYPE: PRT
<213> ORGANISM: Nephila clavata

<400> SEQUENCE: 23

Pro Val Pro Ser Val Phe Ser Ser Pro Ser Leu Ala Ser Gly Phe Leu
1               5                   10                  15

Gly Cys Leu Thr Thr Gly Ile Gly Leu Ser Pro Ala Phe Pro Phe Gln
            20                  25                  30

Glu Gln Gln Asp Leu Asp Asp Leu Ala Lys Val Ile Leu Ser Ala Val
        35                  40                  45

Thr Ser Asn Thr Asp Thr Ser Lys Ser Ala Arg Ala Gln Ala Leu Ser
50                  55                  60

Thr Ala Leu Ala Ser Ser Leu Ala Asp Leu Leu Ile Ser Glu Ser Ser
65                  70                  75                  80

Gly Ser Ser Tyr Gln Thr Gln Ile Ser Ala Leu Thr Asn Ile Leu Ser
                85                  90                  95

Asp Cys Phe Val Thr Thr Thr Gly Ser Asn Asn Pro Ala Phe Val Ser
            100                 105                 110

Arg Val Gln Thr Leu Ile Gly Val Leu Ser Gln Ser Ser Ser Asn Ala
        115                 120                 125

Ile

<210> SEQ ID NO 24
<211> LENGTH: 128
<212> TYPE: PRT
```

<213> ORGANISM: Latrodectus hesperus

<400> SEQUENCE: 24

Ala Ser Val Asn Ile Phe Asn Ser Pro Asn Ala Ala Thr Ser Phe Leu
1               5                   10                  15

Asn Cys Leu Arg Ser Asn Ile Glu Ser Ser Pro Ala Phe Pro Phe Gln
            20                  25                  30

Glu Gln Ala Asp Leu Asp Ser Ile Ala Glu Val Ile Leu Ser Asp Val
        35                  40                  45

Ser Ser Val Asn Thr Ala Ser Ser Ala Thr Ser Leu Ala Leu Ser Thr
    50                  55                  60

Ala Leu Ala Ser Ser Leu Ala Glu Leu Leu Val Thr Glu Ser Ala Glu
65                  70                  75                  80

Glu Asp Ile Asp Asn Gln Val Val Ala Leu Ser Thr Ile Leu Ser Gln
                85                  90                  95

Cys Phe Val Glu Thr Thr Gly Ser Pro Asn Pro Ala Phe Val Ala Ser
            100                 105                 110

Val Lys Ser Leu Leu Gly Val Leu Ser Gln Ser Ala Ser Asn Tyr Glu
            115                 120                 125

<210> SEQ ID NO 25
<211> LENGTH: 130
<212> TYPE: PRT
<213> ORGANISM: Nephila clavipes

<400> SEQUENCE: 25

Ile Ala Asn Ser Pro Phe Ser Asn Pro Asn Thr Ala Glu Ala Phe Ala
1               5                   10                  15

Arg Ser Phe Val Ser Asn Ile Val Ser Ser Gly Glu Phe Gly Ala Gln
            20                  25                  30

Gly Ala Glu Asp Phe Asp Asp Ile Ile Gln Ser Leu Ile Gln Ala Gln
        35                  40                  45

Ser Met Gly Lys Gly Arg His Asp Thr Lys Ala Lys Ala Lys Ala Met
    50                  55                  60

Gln Val Ala Leu Ala Ser Ser Ile Ala Glu Leu Val Ile Ala Glu Ser
65                  70                  75                  80

Ser Gly Gly Asp Val Gln Arg Lys Thr Asn Val Ile Ser Asn Ala Leu
                85                  90                  95

Arg Asn Ala Leu Met Ser Thr Thr Gly Ser Pro Asn Glu Glu Phe Val
            100                 105                 110

His Glu Val Gln Asp Leu Ile Gln Met Leu Ser Gln Gly Gln Ile Asn
            115                 120                 125

Glu Val
    130

<210> SEQ ID NO 26
<211> LENGTH: 130
<212> TYPE: PRT
<213> ORGANISM: Nephila inaurata madagascariensis

<400> SEQUENCE: 26

Ile Val Asn Ser Pro Phe Ser Asn Pro Asn Thr Ala Glu Ala Phe Ala
1               5                   10                  15

Arg Ser Phe Val Ser Asn Val Val Ser Ser Gly Glu Phe Gly Ala Gln
            20                  25                  30

Gly Ala Glu Asp Phe Asp Asp Ile Ile Gln Ser Leu Ile Gln Ala Gln
        35                  40                  45

```
Ser Met Gly Lys Gly Arg His Asp Thr Lys Ala Lys Ala Met
    50                  55                  60

Gln Val Ala Leu Ala Ser Ser Ile Ala Glu Leu Val Ile Ala Glu Ser
65                  70                  75                  80

Ser Gly Gly Asp Val Gln Arg Lys Thr Asn Val Ile Ser Asn Ala Leu
                85                  90                  95

Arg Asn Ala Leu Met Ser Thr Thr Gly Ser Pro Asn Glu Glu Phe Val
                100                 105                 110

His Glu Val Gln Asp Leu Ile Gln Met Leu Ser Gln Glu Gln Ile Asn
            115                 120                 125

Glu Val
    130

<210> SEQ ID NO 27
<211> LENGTH: 80
<212> TYPE: PRT
<213> ORGANISM: Artificial Sequence
<220> FEATURE:
<223> OTHER INFORMATION: Designed polypeptide

<400> SEQUENCE: 27

Met Gly Glu Gln Lys Leu Ile Ser Glu Glu Asp Leu Gly Met Gln Ile
1               5                   10                  15

Ser Met Asp Tyr Glu Ile Lys Phe His Gly Asp Gly Asp Asn Phe Asp
            20                  25                  30

Leu Asn Leu Asp Asp Ser Gly Gly Asp Leu Gln Leu Gln Ile Arg Gly
                35                  40                  45

Pro Gly Gly Arg Val His Val His Ile His Ser Ser Gly Lys Val
    50                  55                  60

Asp Phe His Val Asn Asn Asp Gly Gly Asp Val Glu Val Lys Met His
65                  70                  75                  80

<210> SEQ ID NO 28
<211> LENGTH: 79
<212> TYPE: PRT
<213> ORGANISM: Homo sapiens
<220> FEATURE:
<221> NAME/KEY: DISULFID
<222> LOCATION: (8)..(77)
<220> FEATURE:
<221> NAME/KEY: DISULFID
<222> LOCATION: (11)..(71)
<220> FEATURE:
<221> NAME/KEY: DISULFID
<222> LOCATION: (35)..(46)
<220> FEATURE:
<221> NAME/KEY: DISULFID
<222> LOCATION: (48)..(48)
<223> OTHER INFORMATION: Intermolecular Cys48-Cys48 linkage

<400> SEQUENCE: 28

Phe Pro Ile Pro Leu Pro Tyr Cys Trp Leu Cys Arg Ala Leu Ile Lys
1               5                   10                  15

Arg Ile Gln Ala Met Ile Pro Lys Gly Ala Leu Ala Val Ala Val Ala
            20                  25                  30

Gln Val Cys Arg Val Val Pro Leu Val Ala Gly Gly Ile Cys Gln Cys
                35                  40                  45

Leu Ala Glu Arg Tyr Ser Val Ile Leu Leu Asp Thr Leu Leu Gly Arg
        50                  55                  60

Met Leu Pro Gln Leu Val Cys Arg Leu Val Leu Arg Cys Ser Met
65                  70                  75
```

<210> SEQ ID NO 29
<211> LENGTH: 79
<212> TYPE: PRT
<213> ORGANISM: Mus musculus
<220> FEATURE:
<221> NAME/KEY: DISULFID
<222> LOCATION: (8)..(77)
<220> FEATURE:
<221> NAME/KEY: DISULFID
<222> LOCATION: (11)..(71)
<220> FEATURE:
<221> NAME/KEY: DISULFID
<222> LOCATION: (35)..(46)
<220> FEATURE:
<221> NAME/KEY: DISULFID
<222> LOCATION: (48)..(48)
<223> OTHER INFORMATION: Intermolecular Cys48-Cys48 linkage

<400> SEQUENCE: 29

Leu Pro Ile Pro Leu Pro Phe Cys Trp Leu Cys Arg Thr Leu Ile Lys
1               5                   10                  15

Arg Val Gln Ala Val Ile Pro Lys Gly Val Leu Ala Val Ala Val Ser
            20                  25                  30

Gln Val Cys His Val Val Pro Leu Val Val Gly Gly Ile Cys Gln Cys
        35                  40                  45

Leu Ala Glu Arg Tyr Thr Val Leu Leu Leu Asp Ala Leu Leu Gly Arg
    50                  55                  60

Val Val Pro Gln Leu Val Cys Gly Leu Val Leu Arg Cys Ser Thr
65                  70                  75

<210> SEQ ID NO 30
<211> LENGTH: 79
<212> TYPE: PRT
<213> ORGANISM: Sus scrofa
<220> FEATURE:
<221> NAME/KEY: DISULFID
<222> LOCATION: (8)..(77)
<220> FEATURE:
<221> NAME/KEY: DISULFID
<222> LOCATION: (11)..(71)
<220> FEATURE:
<221> NAME/KEY: DISULFID
<222> LOCATION: (35)..(46)
<220> FEATURE:
<221> NAME/KEY: DISULFID
<222> LOCATION: (48)..(48)
<223> OTHER INFORMATION: Intermolecular Cys48-Cys48 linkage

<400> SEQUENCE: 30

Phe Pro Ile Pro Leu Pro Phe Cys Trp Leu Cys Arg Thr Leu Ile Lys
1               5                   10                  15

Arg Ile Gln Ala Val Val Pro Lys Gly Val Leu Leu Lys Ala Val Ala
            20                  25                  30

Gln Val Cys His Val Val Pro Leu Pro Val Gly Gly Ile Cys Gln Cys
        35                  40                  45

Leu Ala Glu Arg Tyr Ile Val Ile Cys Leu Asn Met Leu Leu Asp Arg
    50                  55                  60

Thr Leu Pro Gln Leu Val Cys Gly Leu Val Leu Arg Cys Ser Ser
65                  70                  75

<210> SEQ ID NO 31
<211> LENGTH: 79
<212> TYPE: PRT
<213> ORGANISM: Oryctolagus cuniculus
<220> FEATURE:

```
<221> NAME/KEY: DISULFID
<222> LOCATION: (8)..(77)
<220> FEATURE:
<221> NAME/KEY: DISULFID
<222> LOCATION: (11)..(71)
<220> FEATURE:
<221> NAME/KEY: DISULFID
<222> LOCATION: (35)..(46)
<220> FEATURE:
<221> NAME/KEY: DISULFID
<222> LOCATION: (48)..(48)
<223> OTHER INFORMATION: Intermolecular Cys48-Cys48 linkage

<400> SEQUENCE: 31

Phe Pro Ile Pro Leu Pro Leu Cys Trp Leu Cys Arg Thr Leu Leu Lys
1               5                   10                  15

Arg Ile Gln Ala Met Ile Pro Lys Gly Val Leu Ala Met Ala Val Ala
                20                  25                  30

Gln Val Cys His Val Val Pro Leu Val Val Gly Gly Ile Cys Gln Cys
            35                  40                  45

Leu Ala Glu Arg Tyr Thr Val Ile Leu Leu Glu Val Leu Leu Gly His
        50                  55                  60

Val Leu Pro Gln Leu Val Cys Gly Leu Val Leu Arg Cys Ser Ser
65                  70                  75

<210> SEQ ID NO 32
<211> LENGTH: 79
<212> TYPE: PRT
<213> ORGANISM: Rattus norvegicus
<220> FEATURE:
<221> NAME/KEY: DISULFID
<222> LOCATION: (8)..(77)
<220> FEATURE:
<221> NAME/KEY: DISULFID
<222> LOCATION: (11)..(71)
<220> FEATURE:
<221> NAME/KEY: DISULFID
<222> LOCATION: (35)..(46)
<220> FEATURE:
<221> NAME/KEY: DISULFID
<222> LOCATION: (48)..(48)
<223> OTHER INFORMATION: Intermolecular Cys48-Cys48 linkage

<400> SEQUENCE: 32

Leu Pro Ile Pro Leu Pro Phe Cys Trp Leu Cys Arg Thr Leu Ile Lys
1               5                   10                  15

Arg Val Gln Ala Val Ile Pro Lys Gly Val Leu Ala Val Ala Val Ser
                20                  25                  30

Gln Val Cys His Val Val Pro Leu Val Val Gly Gly Ile Cys Gln Cys
            35                  40                  45

Leu Ala Glu Arg Tyr Thr Val Leu Leu Leu Asp Ala Leu Leu Gly Arg
        50                  55                  60

Val Val Pro Gln Leu Val Cys Gly Leu Val Leu Arg Cys Ser Thr
65                  70                  75

<210> SEQ ID NO 33
<211> LENGTH: 34
<212> TYPE: PRT
<213> ORGANISM: Artificial Sequence
<220> FEATURE:
<223> OTHER INFORMATION: Construct derived from SP-B
<220> FEATURE:
<221> NAME/KEY: DISULFID
<222> LOCATION: (1)..(33)
<220> FEATURE:
<221> NAME/KEY: DISULFID
<222> LOCATION: (4)..(27)
```

<400> SEQUENCE: 33

Cys Trp Leu Cys Arg Ala Leu Ile Lys Arg Ile Gln Ala Met Ile Pro
1               5                   10                  15

Lys Gly Gly Arg Met Leu Pro Gln Leu Val Cys Arg Leu Val Leu Arg
            20                  25                  30

Cys Ser

<210> SEQ ID NO 34
<211> LENGTH: 34
<212> TYPE: PRT
<213> ORGANISM: Artificial Sequence
<220> FEATURE:
<223> OTHER INFORMATION: Construct derived from SP-B
<220> FEATURE:
<221> NAME/KEY: DISULFID
<222> LOCATION: (1)..(33)
<220> FEATURE:
<221> NAME/KEY: DISULFID
<222> LOCATION: (4)..(27)

<400> SEQUENCE: 34

Cys Trp Leu Cys Arg Ala Leu Ile Lys Arg Ile Gln Ala Leu Ile Pro
1               5                   10                  15

Lys Gly Gly Arg Leu Leu Pro Gln Leu Val Cys Arg Leu Val Leu Arg
            20                  25                  30

Cys Ser

<210> SEQ ID NO 35
<211> LENGTH: 27
<212> TYPE: PRT
<213> ORGANISM: Artificial Sequence
<220> FEATURE:
<223> OTHER INFORMATION: Construct derived from SP-B
<220> FEATURE:
<221> NAME/KEY: DISULFID
<222> LOCATION: (1)..(27)
<220> FEATURE:
<221> NAME/KEY: DISULFID
<222> LOCATION: (4)..(21)

<400> SEQUENCE: 35

Cys Leu Leu Cys Arg Ala Leu Ile Lys Arg Phe Asn Arg Tyr Leu Thr
1               5                   10                  15

Pro Gln Leu Val Cys Arg Leu Val Leu Arg Cys
            20                  25

<210> SEQ ID NO 36
<211> LENGTH: 34
<212> TYPE: PRT
<213> ORGANISM: Artificial Sequence
<220> FEATURE:
<223> OTHER INFORMATION: Construct derived from SP-B
<220> FEATURE:
<221> NAME/KEY: DISULFID
<222> LOCATION: (1)..(33)

<400> SEQUENCE: 36

Cys Trp Leu Ala Arg Ala Leu Ile Lys Arg Ile Gln Ala Leu Ile Pro
1               5                   10                  15

Lys Gly Gly Arg Leu Leu Pro Gln Leu Val Ala Arg Leu Val Leu Arg
            20                  25                  30

Cys Ser

```
<210> SEQ ID NO 37
<211> LENGTH: 34
<212> TYPE: PRT
<213> ORGANISM: Artificial Sequence
<220> FEATURE:
<223> OTHER INFORMATION: Construct derived from SP-B
<220> FEATURE:
<221> NAME/KEY: DISULFID
<222> LOCATION: (4)..(27)

<400> SEQUENCE: 37

Ala Trp Leu Cys Arg Ala Leu Ile Lys Arg Ile Gln Ala Leu Ile Pro
1               5                   10                  15

Lys Gly Gly Arg Leu Leu Pro Gln Leu Val Cys Arg Leu Val Leu Arg
            20                  25                  30

Ala Ser

<210> SEQ ID NO 38
<211> LENGTH: 34
<212> TYPE: PRT
<213> ORGANISM: Artificial Sequence
<220> FEATURE:
<223> OTHER INFORMATION: Construct derived from SP-B
<220> FEATURE:
<221> NAME/KEY: DISULFID
<222> LOCATION: (1)..(33)

<400> SEQUENCE: 38

Cys Trp Leu Leu Arg Ala Leu Ile Lys Arg Ile Gln Ala Leu Ile Pro
1               5                   10                  15

Lys Gly Gly Arg Leu Leu Pro Gln Leu Val Leu Arg Leu Val Leu Arg
            20                  25                  30

Cys Ser

<210> SEQ ID NO 39
<211> LENGTH: 34
<212> TYPE: PRT
<213> ORGANISM: Artificial Sequence
<220> FEATURE:
<223> OTHER INFORMATION: Construct derived from SP-B
<220> FEATURE:
<221> NAME/KEY: DISULFID
<222> LOCATION: (4)..(27)

<400> SEQUENCE: 39

Leu Trp Leu Cys Arg Ala Leu Ile Lys Arg Ile Gln Ala Leu Ile Pro
1               5                   10                  15

Lys Gly Gly Arg Leu Leu Pro Gln Leu Val Cys Arg Leu Val Leu Arg
            20                  25                  30

Leu Ser

<210> SEQ ID NO 40
<211> LENGTH: 35
<212> TYPE: PRT
<213> ORGANISM: Homo sapiens

<400> SEQUENCE: 40

Phe Gly Ile Pro Cys Cys Pro Val His Leu Lys Arg Leu Leu Ile Val
1               5                   10                  15

Val Val Val Val Val Leu Ile Val Val Ile Val Gly Ala Leu Leu
            20                  25                  30

Met Gly Leu
        35
```

<210> SEQ ID NO 41
<211> LENGTH: 35
<212> TYPE: PRT
<213> ORGANISM: Artificial Sequence
<220> FEATURE:
<223> OTHER INFORMATION: Construct derived from SP-C

<400> SEQUENCE: 41

Phe Gly Ile Pro Ser Ser Pro Val His Leu Lys Arg Leu Lys Leu Leu
1               5                   10                  15

Leu Leu Leu Leu Leu Leu Ile Leu Leu Leu Ile Leu Gly Ala Leu Leu
            20                  25                  30

Met Gly Leu
        35

<210> SEQ ID NO 42
<211> LENGTH: 33
<212> TYPE: PRT
<213> ORGANISM: Artificial Sequence
<220> FEATURE:
<223> OTHER INFORMATION: Construct derived from SP-C

<400> SEQUENCE: 42

Ile Pro Ser Ser Pro Val His Leu Lys Arg Leu Lys Leu Leu Leu Leu
1               5                   10                  15

Leu Leu Leu Leu Ile Leu Leu Leu Ile Leu Gly Ala Leu Leu Met Gly
            20                  25                  30

Leu

<210> SEQ ID NO 43
<211> LENGTH: 30
<212> TYPE: PRT
<213> ORGANISM: Artificial Sequence
<220> FEATURE:
<223> OTHER INFORMATION: Construct derived from SP-C

<400> SEQUENCE: 43

Ile Pro Ser Ser Pro Val His Leu Lys Arg Leu Lys Leu Leu Leu Leu
1               5                   10                  15

Leu Leu Leu Leu Ile Leu Leu Leu Ile Leu Gly Ala Leu Leu
            20                  25                  30

<210> SEQ ID NO 44
<211> LENGTH: 33
<212> TYPE: PRT
<213> ORGANISM: Artificial Sequence
<220> FEATURE:
<223> OTHER INFORMATION: Construct derived from SP-C

<400> SEQUENCE: 44

Ile Pro Ser Ser Pro Val His Leu Lys Arg Leu Lys Leu Leu Leu Leu
1               5                   10                  15

Leu Leu Leu Leu Ile Leu Leu Leu Ile Leu Gly Ala Leu Leu Leu Gly
            20                  25                  30

Leu

<210> SEQ ID NO 45
<211> LENGTH: 37
<212> TYPE: PRT
<213> ORGANISM: Homo sapiens

<400> SEQUENCE: 45

Leu Leu Gly Asp Phe Phe Arg Lys Ser Lys Glu Lys Ile Gly Lys Glu
1               5                   10                  15

Phe Lys Arg Ile Val Gln Arg Ile Lys Asp Phe Leu Arg Asn Leu Val
            20                  25                  30

Pro Arg Thr Glu Ser
            35

<210> SEQ ID NO 46
<211> LENGTH: 21
<212> TYPE: PRT
<213> ORGANISM: Artificial Sequence
<220> FEATURE:
<223> OTHER INFORMATION: Construct derived from SP-B

<400> SEQUENCE: 46

Lys Leu Leu Leu Leu Lys Leu Leu Leu Lys Leu Leu Leu Leu Lys
1               5                   10                  15

Leu Leu Leu Leu Lys
            20

<210> SEQ ID NO 47
<211> LENGTH: 148
<212> TYPE: PRT
<213> ORGANISM: Homo sapiens

<400> SEQUENCE: 47

Ala His Leu Asp Glu Glu Leu Gln Ala Thr Leu His Asp Phe Arg His
1               5                   10                  15

Gln Ile Leu Gln Thr Arg Gly Ala Leu Ser Leu Gln Gly Ser Ile Met
            20                  25                  30

Thr Val Gly Glu Lys Val Phe Ser Ser Asn Gly Gln Ser Ile Thr Phe
        35                  40                  45

Asp Ala Ile Gln Glu Ala Cys Ala Arg Ala Gly Gly Arg Ile Ala Val
    50                  55                  60

Pro Arg Asn Pro Glu Glu Asn Glu Ala Ile Ala Ser Phe Val Lys Lys
65                  70                  75                  80

Tyr Asn Thr Tyr Ala Tyr Val Gly Leu Thr Glu Gly Pro Ser Pro Gly
                85                  90                  95

Asp Phe Arg Tyr Ser Asp Gly Thr Pro Val Asn Tyr Thr Asn Trp Tyr
            100                 105                 110

Arg Gly Glu Pro Ala Gly Arg Gly Lys Glu Gln Cys Val Glu Met Tyr
        115                 120                 125

Thr Asp Gly Gln Trp Asn Asp Arg Asn Cys Leu Tyr Ser Arg Leu Thr
    130                 135                 140

Ile Cys Glu Phe
145

<210> SEQ ID NO 48
<211> LENGTH: 148
<212> TYPE: PRT
<213> ORGANISM: Homo sapiens

<400> SEQUENCE: 48

Ala His Leu Asp Glu Glu Leu Gln Ala Thr Leu His Asp Phe Arg His
1               5                   10                  15

Gln Ile Leu Gln Thr Arg Gly Ala Leu Ser Leu Gln Gly Ser Ile Met
            20                  25                  30

Thr Val Gly Glu Lys Val Phe Ser Ser Asn Gly Gln Ser Ile Thr Phe
        35                  40                  45

```
Asp Ala Ile Gln Glu Ala Cys Ala Arg Ala Gly Gly Arg Ile Ala Val
        50                  55                  60

Pro Arg Asn Pro Glu Glu Asn Glu Ala Ile Ala Ser Phe Val Lys Lys
 65                  70                  75                  80

Tyr Asn Thr Tyr Ala Tyr Val Gly Leu Thr Glu Gly Pro Ser Pro Gly
                85                  90                  95

Asp Phe Arg Tyr Ser Asp Gly Thr Pro Val Asn Tyr Thr Asn Trp Tyr
            100                 105                 110

Arg Gly Glu Pro Ala Gly Arg Gly Lys Glu Gln Cys Val Glu Met Tyr
        115                 120                 125

Thr Asp Gly Gln Trp Asn Asp Arg Asn Cys Leu Tyr Ser Arg Leu Thr
    130                 135                 140

Ile Cys Glu Phe
145

<210> SEQ ID NO 49
<211> LENGTH: 152
<212> TYPE: PRT
<213> ORGANISM: Homo sapiens

<400> SEQUENCE: 49

Val Ala Ser Leu Arg Gln Gln Val Glu Ala Leu Gln Gly Gln Val Gln
 1               5                  10                  15

His Leu Gln Ala Ala Phe Ser Gln Tyr Lys Lys Val Glu Leu Phe Pro
             20                  25                  30

Asn Gly Gln Ser Val Gly Glu Lys Ile Phe Lys Thr Ala Gly Phe Val
         35                  40                  45

Lys Pro Phe Thr Glu Ala Gln Leu Leu Cys Thr Gln Ala Gly Gly Gln
 50                  55                  60

Leu Ala Ser Pro Arg Ser Ala Ala Glu Asn Ala Ala Leu Gln Gln Leu
 65                  70                  75                  80

Val Val Ala Lys Asn Glu Ala Ala Phe Leu Ser Met Thr Asp Ser Lys
                 85                  90                  95

Thr Glu Gly Lys Phe Thr Tyr Pro Thr Gly Glu Ser Leu Val Tyr Ser
            100                 105                 110

Asn Trp Ala Pro Gly Glu Pro Asn Asp Asp Gly Gly Ser Glu Asp Cys
        115                 120                 125

Val Glu Ile Phe Thr Asn Gly Lys Trp Asn Asp Arg Ala Cys Gly Glu
    130                 135                 140

Lys Arg Leu Val Val Cys Glu Phe
145                 150

<210> SEQ ID NO 50
<211> LENGTH: 119
<212> TYPE: PRT
<213> ORGANISM: Homo sapiens

<400> SEQUENCE: 50

Gln Thr Ile Glu Glu Asn Ile Lys Ile Phe Glu Glu Glu Glu Val Glu
 1               5                  10                  15

Phe Ile Ser Val Pro Val Pro Glu Phe Ala Asp Ser Asp Pro Ala Asn
             20                  25                  30

Ile Val His Asp Phe Asn Lys Lys Leu Thr Ala Tyr Leu Asp Leu Asn
         35                  40                  45

Leu Asp Lys Cys Tyr Val Ile Pro Leu Asn Thr Ser Ile Val Met Pro
 50                  55                  60
```

```
Pro Arg Asn Leu Leu Glu Leu Ile Asn Ile Lys Ala Gly Thr Tyr
 65                  70                  75                  80

Leu Pro Gln Ser Tyr Leu Ile His Glu His Met Val Ile Thr Asp Arg
             85                  90                  95

Ile Glu Asn Ile Asp His Leu Gly Phe Phe Ile Tyr Arg Leu Cys His
            100                 105                 110

Asp Lys Glu Thr Tyr Lys Leu
            115
```

<210> SEQ ID NO 51
<211> LENGTH: 398
<212> TYPE: PRT
<213> ORGANISM: Homo sapiens

<400> SEQUENCE: 51

```
Gly Pro Asn Ser Thr Gly Ala Thr Ser Pro Glu Glu Ala Ile Ala Asp
 1               5                  10                  15

Leu Ser Val Asn Met Tyr Asn Arg Leu Arg Ala Thr Gly Glu Asp Glu
            20                  25                  30

Asn Ile Leu Phe Ser Pro Leu Ser Ile Ala Leu Ala Met Gly Met Met
            35                  40                  45

Glu Leu Gly Ala Gln Gly Ser Thr Gln Lys Glu Ile Arg His Ser Met
 50                  55                  60

Gly Tyr Asp Ser Leu Lys Asn Gly Glu Glu Phe Ser Phe Leu Lys Glu
 65                  70                  75                  80

Phe Ser Asn Met Val Thr Ala Lys Glu Ser Gln Tyr Val Met Lys Ile
            85                  90                  95

Ala Asn Ser Leu Phe Val Gln Asn Gly Phe His Val Asn Glu Glu Phe
            100                 105                 110

Leu Gln Met Met Lys Lys Tyr Phe Asn Ala Ala Val Asn His Val Asp
            115                 120                 125

Phe Ser Gln Asn Val Ala Val Ala Asn Tyr Ile Asn Lys Trp Val Glu
            130                 135                 140

Asn Asn Thr Asn Asn Leu Val Lys Asp Leu Val Ser Pro Arg Asp Phe
145                 150                 155                 160

Asp Ala Ala Thr Tyr Leu Ala Leu Ile Asn Ala Val Tyr Phe Lys Gly
            165                 170                 175

Asn Trp Lys Ser Gln Phe Arg Pro Glu Asn Thr Arg Thr Phe Ser Phe
            180                 185                 190

Thr Lys Asp Asp Glu Ser Glu Val Gln Ile Pro Met Met Tyr Gln Gln
            195                 200                 205

Gly Glu Phe Tyr Tyr Gly Glu Phe Ser Asp Gly Ser Asn Glu Ala Gly
            210                 215                 220

Gly Ile Tyr Gln Val Leu Glu Ile Pro Tyr Glu Gly Asp Glu Ile Ser
225                 230                 235                 240

Met Met Leu Val Leu Ser Arg Gln Glu Val Pro Leu Ala Thr Leu Glu
            245                 250                 255

Pro Leu Val Lys Ala Gln Leu Val Glu Glu Trp Ala Asn Ser Val Lys
            260                 265                 270

Lys Gln Lys Val Glu Val Tyr Leu Pro Arg Phe Thr Val Glu Gln Glu
            275                 280                 285

Ile Asp Leu Lys Asp Val Leu Lys Ala Leu Gly Ile Thr Glu Ile Phe
            290                 295                 300

Ile Lys Asp Ala Asn Leu Thr Gly Leu Ser Asp Asn Lys Glu Ile Phe
```

```
                     305                 310                 315                 320

Leu Ser Lys Ala Ile His Lys Ser Phe Leu Glu Val Asn Glu Glu Gly
                325                 330                 335

Ser Glu Ala Ala Ala Val Ser Gly Met Ile Ala Ile Ser Arg Met Ala
            340                 345                 350

Val Leu Tyr Pro Gln Val Ile Val Asp His Pro Phe Phe Leu Ile
        355                 360                 365

Arg Asn Arg Arg Thr Gly Thr Ile Leu Phe Met Gly Arg Val Met His
    370                 375                 380

Pro Glu Thr Met Asn Thr Ser Gly His Asp Phe Glu Glu Leu
385                 390                 395

<210> SEQ ID NO 52
<211> LENGTH: 34
<212> TYPE: PRT
<213> ORGANISM: Artificial Sequence
<220> FEATURE:
<223> OTHER INFORMATION: Construct derived from SP-B

<400> SEQUENCE: 52

Ala Trp Leu Ala Arg Ala Leu Ile Lys Arg Ile Gln Ala Leu Ile Pro
1               5                   10                  15

Lys Gly Gly Arg Leu Leu Pro Gln Leu Val Ala Arg Leu Val Leu Arg
            20                  25                  30

Ala Ser

<210> SEQ ID NO 53
<211> LENGTH: 34
<212> TYPE: PRT
<213> ORGANISM: Artificial Sequence
<220> FEATURE:
<223> OTHER INFORMATION: Construct derived from SP-B

<400> SEQUENCE: 53

Leu Trp Leu Leu Arg Ala Leu Ile Lys Arg Ile Gln Ala Leu Ile Pro
1               5                   10                  15

Lys Gly Gly Arg Leu Leu Pro Gln Leu Val Leu Arg Leu Val Leu Arg
            20                  25                  30

Leu Ser

<210> SEQ ID NO 54
<211> LENGTH: 243
<212> TYPE: PRT
<213> ORGANISM: Aequorea victoria

<400> SEQUENCE: 54

Gly Pro Asn Ser Lys Gly Glu Glu Leu Phe Thr Gly Val Val Pro Ile
1               5                   10                  15

Leu Val Glu Leu Asp Gly Asp Val Asn Gly His Lys Phe Ser Val Ser
            20                  25                  30

Gly Glu Gly Glu Gly Asp Ala Thr Tyr Gly Lys Leu Thr Leu Lys Phe
        35                  40                  45

Ile Cys Thr Thr Gly Lys Leu Pro Val Pro Trp Pro Thr Leu Val Thr
    50                  55                  60

Thr Leu Thr Tyr Gly Val Gln Cys Phe Ser Arg Tyr Pro Asp His Met
65                  70                  75                  80

Lys Gln His Asp Phe Phe Lys Ser Ala Met Pro Glu Gly Tyr Val Gln
                85                  90                  95
```

```
Glu Arg Thr Ile Phe Phe Lys Asp Asp Gly Asn Tyr Lys Thr Arg Ala
             100                 105                 110

Glu Val Lys Phe Glu Gly Asp Thr Leu Val Asn Arg Ile Glu Leu Lys
         115                 120                 125

Gly Ile Asp Phe Lys Glu Asp Gly Asn Ile Leu Gly His Lys Leu Glu
     130                 135                 140

Tyr Asn Tyr Asn Ser His Asn Val Tyr Ile Met Ala Asp Lys Gln Lys
145                 150                 155                 160

Asn Gly Ile Lys Val Asn Phe Lys Ile Arg His Asn Ile Glu Asp Gly
                 165                 170                 175

Ser Val Gln Leu Ala Asp His Tyr Gln Gln Asn Thr Pro Ile Gly Asp
             180                 185                 190

Gly Pro Val Leu Leu Pro Asp Asn His Tyr Leu Ser Thr Gln Ser Ala
         195                 200                 205

Leu Ser Lys Asp Pro Asn Glu Lys Arg Asp His Met Val Leu Leu Glu
     210                 215                 220

Phe Val Thr Ala Ala Gly Ile Thr Leu Gly Met Asp Glu Leu Tyr Lys
225                 230                 235                 240

Leu Ile Asn

<210> SEQ ID NO 55
<211> LENGTH: 239
<212> TYPE: PRT
<213> ORGANISM: Artificial Sequence
<220> FEATURE:
<223> OTHER INFORMATION: Modified GFP

<400> SEQUENCE: 55

Lys Gly Glu Glu Leu Phe Thr Gly Val Val Pro Ile Leu Val Glu Leu
1               5                   10                  15

Asp Gly Asp Val Asn Gly His Lys Phe Ser Val Ser Gly Glu Gly Glu
                20                  25                  30

Gly Asp Ala Thr Tyr Gly Lys Leu Thr Leu Lys Phe Ile Cys Thr Thr
             35                  40                  45

Gly Lys Leu Pro Val Pro Trp Pro Thr Leu Val Thr Thr Leu Thr Tyr
         50                  55                  60

Gly Val Gln Cys Phe Ser Arg Tyr Pro Asp His Met Lys Gln His Asp
65                  70                  75                  80

Phe Phe Lys Ser Ala Met Pro Glu Gly Tyr Val Gln Glu Arg Thr Ile
                 85                  90                  95

Phe Phe Lys Asp Asp Gly Asn Tyr Lys Thr Arg Ala Glu Val Lys Phe
             100                 105                 110

Glu Gly Asp Thr Leu Val Asn Arg Ile Glu Leu Lys Gly Ile Asp Phe
         115                 120                 125

Lys Glu Asp Gly Asn Ile Leu Gly His Lys Leu Glu Tyr Asn Tyr Asn
     130                 135                 140

Ser His Asn Val Tyr Ile Met Ala Asp Lys Gln Lys Asn Gly Ile Lys
145                 150                 155                 160

Val Asn Phe Lys Ile Arg His Asn Ile Glu Asp Gly Ser Val Gln Leu
                 165                 170                 175

Ala Asp His Tyr Gln Gln Asn Thr Pro Ile Gly Asp Gly Pro Val Leu
             180                 185                 190

Leu Pro Asp Asn His Tyr Leu Ser Thr Gln Ser Ala Leu Ser Lys Asp
         195                 200                 205

Pro Asn Glu Lys Arg Asp His Met Val Leu Leu Glu Phe Val Thr Ala
```

```
                  210                 215                 220
Ala Gly Ile Thr Leu Gly Met Asp Glu Leu Tyr Lys Leu Ile Asn
225                 230                 235
```

<210> SEQ ID NO 56
<211> LENGTH: 179
<212> TYPE: PRT
<213> ORGANISM: Artificial Sequence
<220> FEATURE:
<223> OTHER INFORMATION: Fusion protein

<400> SEQUENCE: 56

```
Met Gly His His His His His Met Ser His Thr Thr Pro Trp Thr
1               5                   10                  15

Asn Pro Gly Leu Ala Glu Asn Phe Met Asn Ser Phe Met Gln Gly Leu
                20                  25                  30

Ser Ser Met Pro Gly Phe Thr Ala Ser Gln Leu Asp Lys Met Ser Thr
                35                  40                  45

Ile Ala Gln Ser Met Val Gln Ser Ile Gln Ser Leu Ala Ala Gln Gly
            50                  55                  60

Arg Thr Ser Pro Asn Asp Leu Gln Ala Leu Asn Met Ala Phe Ala Ser
65                  70                  75                  80

Ser Met Ala Glu Ile Ala Ala Ser Glu Glu Gly Gly Gly Ser Leu Ser
                85                  90                  95

Thr Lys Thr Ser Ser Ile Ala Ser Ala Met Ser Asn Ala Phe Leu Gln
                100                 105                 110

Thr Thr Gly Val Val Asn Gln Pro Phe Ile Asn Glu Ile Thr Gln Leu
                115                 120                 125

Val Ser Met Phe Ala Gln Ala Gly Met Asn Asp Val Ser Ala Gly Asn
            130                 135                 140

Ser Met Ile Pro Ser Ser Pro Val His Leu Lys Arg Leu Lys Leu Leu
145                 150                 155                 160

Leu Leu Leu Leu Leu Ile Leu Leu Leu Ile Leu Gly Ala Leu Leu
                165                 170                 175

Leu Gly Leu
```

<210> SEQ ID NO 57
<211> LENGTH: 179
<212> TYPE: PRT
<213> ORGANISM: Artificial Sequence
<220> FEATURE:
<223> OTHER INFORMATION: Fusion protein

<400> SEQUENCE: 57

```
Met Gly His His His His His Met Ser His Thr Thr Pro Trp Thr
1               5                   10                  15

Asn Pro Gly Leu Ala Glu Asn Phe Met Asn Ser Phe Met Gln Gly Leu
                20                  25                  30

Ser Ser Met Pro Gly Phe Thr Ala Ser Gln Leu Asp Asp Met Ser Thr
                35                  40                  45

Ile Ala Gln Ser Met Val Gln Ser Ile Gln Ser Leu Ala Ala Gln Gly
            50                  55                  60

Arg Thr Ser Pro Asn Lys Leu Gln Ala Leu Asn Met Ala Phe Ala Ser
65                  70                  75                  80

Ser Met Ala Glu Ile Ala Ala Ser Glu Glu Gly Gly Gly Ser Leu Ser
                85                  90                  95

Thr Lys Thr Ser Ser Ile Ala Ser Ala Met Ser Asn Ala Phe Leu Gln
```

```
              100                 105                 110
Thr Thr Gly Val Val Asn Gln Pro Phe Ile Asn Glu Ile Thr Gln Leu
            115                 120                 125

Val Ser Met Phe Ala Gln Ala Gly Met Asn Asp Val Ser Ala Gly Asn
            130                 135                 140

Ser Met Ile Pro Ser Ser Pro Val His Leu Lys Arg Leu Lys Leu Leu
145                 150                 155                 160

Leu Leu Leu Leu Leu Leu Ile Leu Leu Leu Ile Leu Gly Ala Leu Leu
                165                 170                 175

Leu Gly Leu

<210> SEQ ID NO 58
<211> LENGTH: 537
<212> TYPE: DNA
<213> ORGANISM: Artificial Sequence
<220> FEATURE:
<223> OTHER INFORMATION: Fusion protein

<400> SEQUENCE: 58
atgggccatc atcatcatca tcatatgtca cacactacac catggacaaa cccaggactc     60
gcagaaaact tcatgaacag tttcatgcaa ggcctgagct cgatgccagg tttcacggca    120
agccaattgg ataagatgtc aaccatcgca caatccatgg tacagtcaat acaatccttg    180
gcggcacaag gcaggacatc accgaatgac ctgcaggccc ttaacatggc ttttgcatct    240
tcgatggcag aaatcgcggc atccgaagaa ggaggggggaa gcctttccac caaaactagc    300
tctatagcca gtgcaatgtc caacgcgttt ctgcaaacaa ctggagtggt aaaccaaccg    360
ttcataaatg aaataactca gctcgttagc atgtttgctc aagcaggtat gaatgatgtc    420
agtgctggga attctatgat tccgagcagc ccggtgcatc tgaaacgcct gaaactgctg    480
ctgctgctgc tgctgctgat tctgctgctg attctgggcg cgctgctgct gggcctg       537

<210> SEQ ID NO 59
<211> LENGTH: 537
<212> TYPE: DNA
<213> ORGANISM: Artificial Sequence
<220> FEATURE:
<223> OTHER INFORMATION: Fusion protein

<400> SEQUENCE: 59
atgggccatc atcatcatca tcatatgtca cacactacac catggacaaa cccaggactc     60
gcagaaaact tcatgaacag tttcatgcaa ggcctgagct cgatgccagg tttcacggca    120
agccaattgg atgatatgtc aaccatcgca caatccatgg tacagtcaat acaatccttg    180
gcggcacaag gcaggacatc accgaataag ctgcaggccc ttaacatggc ttttgcatct    240
tcgatggcag aaatcgcggc atccgaagaa ggaggggggaa gcctttccac caaaactagc    300
tctatagcca gtgcaatgtc caacgcgttt ctgcaaacaa ctggagtggt aaaccaaccg    360
ttcataaatg aaataactca gctcgttagc atgtttgctc aagcaggtat gaatgatgtc    420
agtgctggga attctatgat tccgagcagc ccggtgcatc tgaaacgcct gaaactgctg    480
ctgctgctgc tgctgctgat tctgctgctg attctgggcg cgctgctgct gggcctg       537

<210> SEQ ID NO 60
<211> LENGTH: 167
<212> TYPE: PRT
<213> ORGANISM: Artificial Sequence
<220> FEATURE:
<223> OTHER INFORMATION: Fusion protein
```

<400> SEQUENCE: 60

```
Met Gly His His His His His Met Ser His Thr Thr Pro Trp Thr
1               5                   10                  15

Asn Pro Gly Leu Ala Glu Asn Phe Met Asn Ser Phe Met Gln Gly Leu
            20                  25                  30

Ser Ser Met Pro Gly Phe Thr Ala Ser Gln Leu Asp Lys Met Ser Thr
        35                  40                  45

Ile Ala Gln Ser Met Val Gln Ser Ile Gln Ser Leu Ala Ala Gln Gly
    50                  55                  60

Arg Thr Ser Pro Asn Asp Leu Gln Ala Leu Asn Met Ala Phe Ala Ser
65                  70                  75                  80

Ser Met Ala Glu Ile Ala Ala Ser Glu Glu Gly Gly Gly Ser Leu Ser
                85                  90                  95

Thr Lys Thr Ser Ser Ile Ala Ser Ala Met Ser Asn Ala Phe Leu Gln
            100                 105                 110

Thr Thr Gly Val Val Asn Gln Pro Phe Ile Asn Glu Ile Thr Gln Leu
        115                 120                 125

Val Ser Met Phe Ala Gln Ala Gly Met Asn Asp Val Ser Ala Gly Asn
    130                 135                 140

Ser Met Lys Leu Leu Leu Leu Lys Leu Leu Leu Leu Lys Leu Leu Leu
145                 150                 155                 160

Leu Lys Leu Leu Leu Leu Lys
            165
```

<210> SEQ ID NO 61
<211> LENGTH: 167
<212> TYPE: PRT
<213> ORGANISM: Artificial Sequence
<220> FEATURE:
<223> OTHER INFORMATION: Fusion protein

<400> SEQUENCE: 61

```
Met Gly His His His His His Met Ser His Thr Thr Pro Trp Thr
1               5                   10                  15

Asn Pro Gly Leu Ala Glu Asn Phe Met Asn Ser Phe Met Gln Gly Leu
            20                  25                  30

Ser Ser Met Pro Gly Phe Thr Ala Ser Gln Leu Asp Asp Met Ser Thr
        35                  40                  45

Ile Ala Gln Ser Met Val Gln Ser Ile Gln Ser Leu Ala Ala Gln Gly
    50                  55                  60

Arg Thr Ser Pro Asn Lys Leu Gln Ala Leu Asn Met Ala Phe Ala Ser
65                  70                  75                  80

Ser Met Ala Glu Ile Ala Ala Ser Glu Glu Gly Gly Gly Ser Leu Ser
                85                  90                  95

Thr Lys Thr Ser Ser Ile Ala Ser Ala Met Ser Asn Ala Phe Leu Gln
            100                 105                 110

Thr Thr Gly Val Val Asn Gln Pro Phe Ile Asn Glu Ile Thr Gln Leu
        115                 120                 125

Val Ser Met Phe Ala Gln Ala Gly Met Asn Asp Val Ser Ala Gly Asn
    130                 135                 140

Ser Met Lys Leu Leu Leu Leu Lys Leu Leu Leu Leu Lys Leu Leu Leu
145                 150                 155                 160

Leu Lys Leu Leu Leu Leu Lys
            165
```

<210> SEQ ID NO 62
<211> LENGTH: 501
<212> TYPE: DNA
<213> ORGANISM: Artificial Sequence
<220> FEATURE:
<223> OTHER INFORMATION: Fusion protein

<400> SEQUENCE: 62

```
atgggccatc atcatcatca tcatatgtca cacactacac catggacaaa cccaggactc      60
gcagaaaact tcatgaacag tttcatgcaa ggcctgagct cgatgccagg tttcacggca     120
agccaattgg ataagatgtc aaccatcgca caatccatgg tacagtcaat acaatccttg     180
gcggcacaag gcaggacatc accgaatgac ctgcaggccc ttaacatggc ttttgcatct     240
tcgatggcag aaatcgcggc atccgaagaa ggagggggaa gcctttccac caaaactagc     300
tctatagcca gtgcaatgtc caacgcgttt ctgcaaacaa ctggagtggt aaaccaaccg     360
ttcataaatg aaataactca gctcgttagc atgtttgctc aagcaggtat gaatgatgtc     420
agtgctggga attctatgaa actgcttctg ctgaaactcc tgttattgaa actactgctg     480
ttgaaactcc tgctgttaaa g                                                501
```

<210> SEQ ID NO 63
<211> LENGTH: 501
<212> TYPE: DNA
<213> ORGANISM: Artificial Sequence
<220> FEATURE:
<223> OTHER INFORMATION: Fusion protein

<400> SEQUENCE: 63

```
atgggccatc atcatcatca tcatatgtca cacactacac catggacaaa cccaggactc      60
gcagaaaact tcatgaacag tttcatgcaa ggcctgagct cgatgccagg tttcacggca     120
agccaattgg atgatatgtc aaccatcgca caatccatgg tacagtcaat acaatccttg     180
gcggcacaag gcaggacatc accgaataag ctgcaggccc ttaacatggc ttttgcatct     240
tcgatggcag aaatcgcggc atccgaagaa ggagggggaa gcctttccac caaaactagc     300
tctatagcca gtgcaatgtc caacgcgttt ctgcaaacaa ctggagtggt aaaccaaccg     360
ttcataaatg aaataactca gctcgttagc atgtttgctc aagcaggtat gaatgatgtc     420
agtgctggga attctatgaa actgcttctg ctgaaactcc tgttattgaa actactgctg     480
ttgaaactcc tgctgttaaa g                                                501
```

<210> SEQ ID NO 64
<211> LENGTH: 231
<212> TYPE: PRT
<213> ORGANISM: Artificial Sequence
<220> FEATURE:
<223> OTHER INFORMATION: Fusion protein

<400> SEQUENCE: 64

```
Met Gly His His His His His His Met Ser Thr Thr Pro Trp Thr
1               5                  10                  15

Asn Pro Gly Leu Ala Glu Asn Phe Met Asn Ser Phe Met Gln Gly Leu
            20                  25                  30

Ser Ser Met Pro Gly Phe Thr Ala Ser Gln Leu Asp Lys Met Ser Thr
        35                  40                  45

Ile Ala Gln Ser Met Val Gln Ser Ile Gln Ser Leu Ala Ala Gln Gly
    50                  55                  60

Arg Thr Ser Pro Asn Asp Leu Gln Ala Leu Asn Met Ala Phe Ala Ser
```

```
                65                  70                  75                  80
Ser Met Ala Glu Ile Ala Ala Ser Glu Glu Gly Gly Gly Ser Leu Ser
                    85                  90                  95

Thr Lys Thr Ser Ser Ile Ala Ser Ala Met Ser Asn Ala Phe Leu Gln
                100                 105                 110

Thr Thr Gly Val Val Asn Gln Pro Phe Ile Asn Glu Ile Thr Gln Leu
                115                 120                 125

Val Ser Met Phe Ala Gln Ala Gly Met Asn Asp Val Ser Ala Gly Asn
            130                 135                 140

Ser Leu Val Pro Arg Gly Ser Met Gly Glu Gln Lys Leu Ile Ser Glu
145                 150                 155                 160

Glu Asp Leu Gly Met Gln Ile Ser Met Asp Tyr Glu Ile Lys Phe His
                165                 170                 175

Gly Asp Gly Asp Asn Phe Asp Leu Asn Leu Asp Asp Ser Gly Gly Asp
            180                 185                 190

Leu Gln Leu Gln Ile Arg Gly Pro Gly Gly Arg Val His Val His Ile
                195                 200                 205

His Ser Ser Ser Gly Lys Val Asp Phe His Val Asn Asn Asp Gly Gly
        210                 215                 220

Asp Val Glu Val Lys Met His
225                 230

<210> SEQ ID NO 65
<211> LENGTH: 693
<212> TYPE: DNA
<213> ORGANISM: Artificial Sequence
<220> FEATURE:
<223> OTHER INFORMATION: Fusion protein

<400> SEQUENCE: 65
atgggccatc atcatcatca tcatatgtca cacactacac catggacaaa cccaggactc        60
gcagaaaact tcatgaacag tttcatgcaa ggcctgagct cgatgccagg tttcacggca       120
agccaattgg ataagatgtc aaccatcgca caatccatgg tacagtcaat acaatccttg       180
gcggcacaag gcaggacatc accgaatgac ctgcaggccc ttaacatggc ttttgcatct       240
tcgatggcag aaatcgcggc atccgaagaa ggaggggggaa gccttttccac caaaactagc       300 tctatagcca gtgcaatgtc caacgcgttt ctgcaaacaa ctggagtggt aaaccaaccg       360
ttcataaatg aaataactca gctcgttagc atgtttgctc aagcaggtat gaatgatgtc       420
agtgctggga attccctggt gccacgcggt tctatgggcg aacagaagtt aatctcccgag       480 gaggacttgg gaatgcagat cagcatggac tatgaaatta aatttcacgg ggatggcgat       540
aatttcgacc tcaatctgga tgattcgggg ggcgatctgc agctgcaaat cgtggtccg       600 ggcggtcgcg ttcatgtaca cattcactca agttctggca agtggacttc tcatgtcaac       660
aacgatggtg gtgatgttga agtgaaaatg cat                                    693

<210> SEQ ID NO 66
<211> LENGTH: 270
<212> TYPE: PRT
<213> ORGANISM: Artificial Sequence
<220> FEATURE:
<223> OTHER INFORMATION: Fusion protein

<400> SEQUENCE: 66

Met Gly His His His His His His Met Ser His Thr Thr Pro Trp Thr
1               5                   10                  15
```

Asn Pro Gly Leu Ala Glu Asn Phe Met Asn Ser Phe Met Gln Gly Leu
            20                  25                  30

Ser Ser Met Pro Gly Phe Thr Ala Ser Gln Leu Asp Lys Met Ser Thr
        35                  40                  45

Ile Ala Gln Ser Met Val Gln Ser Ile Gln Ser Leu Ala Ala Gln Gly
 50                  55                  60

Arg Thr Ser Pro Asn Asp Leu Gln Ala Leu Asn Met Ala Phe Ala Ser
 65                  70                  75                  80

Ser Met Ala Glu Ile Ala Ala Ser Glu Glu Gly Gly Ser Leu Ser
                85                  90                  95

Thr Lys Thr Ser Ser Ile Ala Ser Ala Met Ser Asn Ala Phe Leu Gln
            100                 105                 110

Thr Thr Gly Val Val Asn Gln Pro Phe Ile Asn Glu Ile Thr Gln Leu
            115                 120                 125

Val Ser Met Phe Ala Gln Ala Gly Met Asn Asp Val Ser Ala Gly Asn
130                 135                 140

Ser Leu Val Pro Arg Gly Ser Gln Thr Ile Glu Glu Asn Ile Lys Ile
145                 150                 155                 160

Phe Glu Glu Glu Val Glu Phe Ile Ser Val Pro Val Pro Glu Phe
                165                 170                 175

Ala Asp Ser Asp Pro Ala Asn Ile Val His Asp Phe Asn Lys Lys Leu
            180                 185                 190

Thr Ala Tyr Leu Asp Leu Asn Leu Asp Lys Cys Tyr Val Ile Pro Leu
            195                 200                 205

Asn Thr Ser Ile Val Met Pro Pro Arg Asn Leu Leu Glu Leu Leu Ile
210                 215                 220

Asn Ile Lys Ala Gly Thr Tyr Leu Pro Gln Ser Tyr Leu Ile His Glu
225                 230                 235                 240

His Met Val Ile Thr Asp Arg Ile Glu Asn Ile Asp His Leu Gly Phe
                245                 250                 255

Phe Ile Tyr Arg Leu Cys His Asp Lys Glu Thr Tyr Lys Leu
            260                 265                 270

<210> SEQ ID NO 67
<211> LENGTH: 270
<212> TYPE: PRT
<213> ORGANISM: Artificial Sequence
<220> FEATURE:
<223> OTHER INFORMATION: Fusion protein

<400> SEQUENCE: 67

Met Gly His His His His His Met Ser His Thr Thr Pro Trp Thr
 1               5                  10                  15

Asn Pro Gly Leu Ala Glu Asn Phe Met Asn Ser Phe Met Gln Gly Leu
            20                  25                  30

Ser Ser Met Pro Gly Phe Thr Ala Ser Gln Leu Asp Asp Met Ser Thr
        35                  40                  45

Ile Ala Gln Ser Met Val Gln Ser Ile Gln Ser Leu Ala Ala Gln Gly
 50                  55                  60

Arg Thr Ser Pro Asn Lys Leu Gln Ala Leu Asn Met Ala Phe Ala Ser
 65                  70                  75                  80

Ser Met Ala Glu Ile Ala Ala Ser Glu Glu Gly Gly Ser Leu Ser
                85                  90                  95

Thr Lys Thr Ser Ser Ile Ala Ser Ala Met Ser Asn Ala Phe Leu Gln
            100                 105                 110

```
Thr Thr Gly Val Val Asn Gln Pro Phe Ile Asn Glu Ile Thr Gln Leu
            115                 120                 125

Val Ser Met Phe Ala Gln Ala Gly Met Asn Asp Val Ser Ala Gly Asn
    130                 135                 140

Ser Leu Val Pro Arg Gly Ser Gln Thr Ile Glu Glu Asn Ile Lys Ile
145                 150                 155                 160

Phe Glu Glu Glu Val Glu Phe Ile Ser Val Pro Val Pro Glu Phe
                165                 170                 175

Ala Asp Ser Asp Pro Ala Asn Ile Val His Asp Phe Asn Lys Lys Leu
                180                 185                 190

Thr Ala Tyr Leu Asp Leu Asn Leu Asp Lys Cys Tyr Val Ile Pro Leu
    195                 200                 205

Asn Thr Ser Ile Val Met Pro Pro Arg Asn Leu Leu Glu Leu Leu Ile
    210                 215                 220

Asn Ile Lys Ala Gly Thr Tyr Leu Pro Gln Ser Tyr Leu Ile His Glu
225                 230                 235                 240

His Met Val Ile Thr Asp Arg Ile Glu Asn Ile Asp His Leu Gly Phe
                245                 250                 255

Phe Ile Tyr Arg Leu Cys His Asp Lys Glu Thr Tyr Lys Leu
            260                 265                 270

<210> SEQ ID NO 68
<211> LENGTH: 810
<212> TYPE: DNA
<213> ORGANISM: Artificial Sequence
<220> FEATURE:
<223> OTHER INFORMATION: Fusion protein

<400> SEQUENCE: 68
atgggccatc atcatcatca tcatatgtca cacactacac catggacaaa cccaggactc    60
gcagaaaact tcatgaacag tttcatgcaa ggcctgagct cgatgccagg tttcacggca   120
agccaattgg ataagatgtc aaccatcgca caatccatgg tacagtcaat acaatccttg   180
gcggcacaag gcaggacatc accgaatgac ctgcaggccc ttaacatggc ttttgcatct   240
tcgatggcag aaatcgcggc atccgaagaa ggagggggaa gcctttccac caaaactagc   300
tctatagcca gtgcaatgtc caacgcgttt ctgcaaacaa ctggagtggt aaaccaaccg   360
ttcataaatg aaataactca gctcgttagc atgtttgctc aagcaggtat gaatgatgtc   420
agtgctggga attccctggt gccacgcggt tctcagacaa ttgaagaaaa tattaaaatc   480
tttgaagaag aagaagttga atttatcagt gtgcctgtcc cagagtttgc agatagtgat   540
cctgccaaca ttgttcatga ctttaacaag aaacttacag cctatttaga tcttaacctg   600
gataagtgct atgtgatccc tctgaacact ccattgtta tgccacccag aaacctactg    660
gagttactta ttaacatcaa ggctggaacc tatttgcctc agtcctatct gattcatgag   720
cacatggtta ttactgatcg cattgaaaac attgatcacc tgggtttctt tatttatcga   780
ctgtgtcatg acaaggaaac ttacaaactg                                     810

<210> SEQ ID NO 69
<211> LENGTH: 810
<212> TYPE: DNA
<213> ORGANISM: Artificial Sequence
<220> FEATURE:
<223> OTHER INFORMATION: Fusion protein

<400> SEQUENCE: 69
atgggccatc atcatcatca tcatatgtca cacactacac catggacaaa cccaggactc    60
```

-continued

```
gcagaaaact tcatgaacag tttcatgcaa ggcctgagct cgatgccagg tttcacggca      120
agccaattgg atgatatgtc aaccatcgca caatccatgg tacagtcaat acaatccttg      180
gcggcacaag gcaggacatc accgaataag ctgcaggccc ttaacatggc ttttgcatct      240
tcgatggcag aaatcgcggc atccgaagaa ggagggggaa gcctttccac caaaactagc      300
tctatagcca gtgcaatgtc caacgcgttt ctgcaaacaa ctggagtggt aaaccaaccg      360
ttcataaatg aaataactca gctcgttagc atgtttgctc aagcaggtat gaatgatgtc      420
agtgctggga attccctggt gccacgcggt tctcagacaa ttgaagaaaa tattaaaatc      480
tttgaagaag aagaagttga atttatcagt gtgcctgtcc cagagtttgc agatagtgat      540
cctgccaaca ttgttcatga ctttaacaag aaacttacag cctatttaga tcttaacctg      600
gataagtgct atgtgatccc tctgaacact tccattgtta tgccacccag aaacctactg      660
gagttactta ttaacatcaa ggctggaacc tatttgcctc agtcctatct gattcatgag      720
cacatggtta ttactgatcg cattgaaaac attgatcacc tgggtttctt tatttatcga      780
ctgtgtcatg acaaggaaac ttacaaactg                                      810
```

<210> SEQ ID NO 70
<211> LENGTH: 380
<212> TYPE: PRT
<213> ORGANISM: Artificial Sequence
<220> FEATURE:
<223> OTHER INFORMATION: Fusion protein

<400> SEQUENCE: 70

```
Met Gly His His His His His His Met Ser His Thr Thr Pro Trp Thr
1               5                   10                  15

Asn Pro Gly Leu Ala Glu Asn Phe Met Asn Ser Phe Met Gln Gly Leu
            20                  25                  30

Ser Ser Met Pro Gly Phe Thr Ala Ser Gln Leu Asp Lys Met Ser Thr
        35                  40                  45

Ile Ala Gln Ser Met Val Gln Ser Ile Gln Ser Leu Ala Ala Gln Gly
    50                  55                  60

Arg Thr Ser Pro Asn Asp Leu Gln Ala Leu Asn Met Ala Phe Ala Ser
65                  70                  75                  80

Ser Met Ala Glu Ile Ala Ala Ser Glu Glu Gly Gly Gly Ser Leu Ser
                85                  90                  95

Thr Lys Thr Ser Ser Ile Ala Ser Ala Met Ser Asn Ala Phe Leu Gln
            100                 105                 110

Thr Thr Gly Val Val Asn Gln Pro Phe Ile Asn Glu Ile Thr Gln Leu
        115                 120                 125

Val Ser Met Phe Ala Gln Ala Gly Met Asn Asp Val Ser Ala Gly Asn
    130                 135                 140

Ser Leu Glu Ala Leu Phe Gln Gly Glu Val Lys Asp Val Cys Val Gly
145                 150                 155                 160

Ser Pro Gly Ile Pro Gly Thr Pro Gly Ser His Gly Leu Pro Gly Arg
                165                 170                 175

Asp Gly Arg Asp Gly Leu Lys Gly Asp Pro Gly Pro Gly Pro Met
            180                 185                 190

Gly Pro Pro Gly Glu Met Pro Cys Pro Pro Gly Asn Asp Gly Leu Pro
        195                 200                 205

Gly Ala Pro Gly Ile Pro Gly Glu Cys Gly Glu Lys Gly Glu Pro Gly
    210                 215                 220
```

Glu Arg Gly Pro Pro Gly Leu Pro Ala His Leu Asp Glu Glu Leu Gln
225                 230                 235                 240

Ala Thr Leu His Asp Phe Arg His Gln Ile Leu Gln Thr Arg Gly Ala
            245                 250                 255

Leu Ser Leu Gln Gly Ser Ile Met Thr Val Gly Glu Lys Val Phe Ser
        260                 265                 270

Ser Asn Gly Gln Ser Ile Thr Phe Asp Ala Ile Gln Glu Ala Cys Ala
    275                 280                 285

Arg Ala Gly Gly Arg Ile Ala Val Pro Arg Asn Pro Glu Glu Asn Glu
290                 295                 300

Ala Ile Ala Ser Phe Val Lys Lys Tyr Asn Thr Tyr Ala Tyr Val Gly
305                 310                 315                 320

Leu Thr Glu Gly Pro Ser Pro Gly Asp Phe Arg Tyr Ser Asp Gly Thr
                325                 330                 335

Pro Val Asn Tyr Thr Asn Trp Tyr Arg Gly Glu Pro Ala Gly Arg Gly
            340                 345                 350

Lys Glu Gln Cys Val Glu Met Tyr Thr Asp Gly Gln Trp Asn Asp Arg
        355                 360                 365

Asn Cys Leu Tyr Ser Arg Leu Thr Ile Cys Glu Phe
    370                 375                 380

<210> SEQ ID NO 71
<211> LENGTH: 380
<212> TYPE: PRT
<213> ORGANISM: Artificial Sequence
<220> FEATURE:
<223> OTHER INFORMATION: Fusion protein

<400> SEQUENCE: 71

Met Gly His His His His His His Met Ser His Thr Thr Pro Trp Thr
1               5                   10                  15

Asn Pro Gly Leu Ala Glu Asn Phe Met Asn Ser Phe Met Gln Gly Leu
            20                  25                  30

Ser Ser Met Pro Gly Phe Thr Ala Ser Gln Leu Asp Lys Met Ser Thr
        35                  40                  45

Ile Ala Gln Ser Met Val Gln Ser Ile Gln Ser Leu Ala Ala Gln Gly
    50                  55                  60

Arg Thr Ser Pro Asn Asp Leu Gln Ala Leu Asn Met Ala Phe Ala Ser
65                  70                  75                  80

Ser Met Ala Glu Ile Ala Ala Ser Glu Glu Gly Gly Ser Leu Ser
                85                  90                  95

Thr Lys Thr Ser Ser Ile Ala Ser Ala Met Ser Asn Ala Phe Leu Gln
                100                 105                 110

Thr Thr Gly Val Val Asn Gln Pro Phe Ile Asn Glu Ile Thr Gln Leu
            115                 120                 125

Val Ser Met Phe Ala Gln Ala Gly Met Asn Asp Val Ser Ala Gly Asn
130                 135                 140

Ser Leu Glu Ala Leu Phe Gln Gly Glu Val Lys Asp Val Cys Val Gly
145                 150                 155                 160

Ser Pro Gly Ile Pro Gly Thr Pro Gly Ser His Gly Leu Pro Gly Arg
                165                 170                 175

Asp Gly Arg Asp Gly Val Lys Gly Asp Pro Gly Pro Pro Gly Pro Met
            180                 185                 190

Gly Pro Pro Gly Glu Thr Pro Cys Pro Pro Gly Asn Asn Gly Leu Pro
        195                 200                 205

-continued

Gly Ala Pro Gly Val Pro Gly Glu Arg Gly Glu Lys Gly Glu Pro Gly
        210                 215                 220

Glu Arg Gly Pro Pro Gly Leu Pro Ala His Leu Asp Glu Glu Leu Gln
225                 230                 235                 240

Ala Thr Leu His Asp Phe Arg His Gln Ile Leu Gln Thr Arg Gly Ala
                245                 250                 255

Leu Ser Leu Gln Gly Ser Ile Met Thr Val Gly Glu Lys Val Phe Ser
            260                 265                 270

Ser Asn Gly Gln Ser Ile Thr Phe Asp Ala Ile Gln Glu Ala Cys Ala
        275                 280                 285

Arg Ala Gly Gly Arg Ile Ala Val Pro Arg Asn Pro Glu Glu Asn Glu
290                 295                 300

Ala Ile Ala Ser Phe Val Lys Lys Tyr Asn Thr Tyr Ala Tyr Val Gly
305                 310                 315                 320

Leu Thr Glu Gly Pro Ser Pro Gly Asp Phe Arg Tyr Ser Asp Gly Thr
                325                 330                 335

Pro Val Asn Tyr Thr Asn Trp Tyr Arg Gly Glu Pro Ala Gly Arg Gly
            340                 345                 350

Lys Glu Gln Cys Val Glu Met Tyr Thr Asp Gly Gln Trp Asn Asp Arg
        355                 360                 365

Asn Cys Leu Tyr Ser Arg Leu Thr Ile Cys Glu Phe
370                 375                 380

<210> SEQ ID NO 72
<211> LENGTH: 507
<212> TYPE: PRT
<213> ORGANISM: Artificial Sequence
<220> FEATURE:
<223> OTHER INFORMATION: Fusion protein

<400> SEQUENCE: 72

Met Gly His His His His His His Met Ser Thr Thr Pro Trp Thr
1               5                   10                  15

Asn Pro Gly Leu Ala Glu Asn Phe Met Asn Ser Phe Met Gln Gly Leu
            20                  25                  30

Ser Ser Met Pro Gly Phe Thr Ala Ser Gln Leu Asp Lys Met Ser Thr
        35                  40                  45

Ile Ala Gln Ser Met Val Gln Ser Ile Gln Ser Leu Ala Ala Gln Gly
    50                  55                  60

Arg Thr Ser Pro Asn Asp Leu Gln Ala Leu Asn Met Ala Phe Ala Ser
65                  70                  75                  80

Ser Met Ala Glu Ile Ala Ala Ser Glu Glu Gly Gly Ser Leu Ser
                85                  90                  95

Thr Lys Thr Ser Ser Ile Ala Ser Ala Met Ser Asn Ala Phe Leu Gln
            100                 105                 110

Thr Thr Gly Val Val Asn Gln Pro Phe Ile Asn Glu Ile Thr Gln Leu
        115                 120                 125

Val Ser Met Phe Ala Gln Ala Gly Met Asn Asp Val Ser Ala Gly Asn
    130                 135                 140

Ser Leu Glu Ala Leu Phe Gln Gly Ala Glu Met Lys Thr Tyr Ser His
145                 150                 155                 160

Arg Thr Met Pro Ser Ala Cys Thr Leu Val Met Cys Ser Ser Val Glu
                165                 170                 175

Ser Gly Leu Pro Gly Arg Asp Gly Arg Asp Gly Arg Glu Gly Pro Arg
            180                 185                 190

Gly Glu Lys Gly Asp Pro Gly Leu Pro Gly Ala Ala Gly Gln Ala Gly
            195                 200                 205

Met Pro Gly Gln Ala Gly Pro Val Gly Pro Lys Gly Asp Asn Gly Ser
    210                 215                 220

Val Gly Glu Pro Gly Pro Lys Gly Asp Thr Gly Pro Ser Gly Pro Pro
225                 230                 235                 240

Gly Pro Pro Gly Val Pro Gly Ala Gly Arg Glu Gly Pro Leu Gly
            245                 250                 255

Lys Gln Gly Asn Ile Gly Pro Gln Lys Pro Gly Pro Lys Gly Glu
            260                 265                 270

Ala Gly Pro Lys Gly Glu Val Gly Ala Pro Gly Met Gln Gly Ser Ala
            275                 280                 285

Gly Ala Arg Gly Leu Ala Gly Pro Lys Gly Glu Arg Gly Val Pro Gly
            290                 295                 300

Glu Arg Gly Val Pro Gly Asn Thr Gly Ala Ala Gly Ser Ala Gly Ala
305                 310                 315                 320

Met Gly Pro Gln Gly Ser Pro Gly Ala Arg Gly Pro Pro Gly Leu Lys
            325                 330                 335

Gly Asp Lys Gly Ile Pro Gly Asp Lys Gly Ala Lys Gly Glu Ser Gly
            340                 345                 350

Leu Pro Asp Val Ala Ser Leu Arg Gln Gln Val Glu Ala Leu Gln Gly
            355                 360                 365

Gln Val Gln His Leu Gln Ala Ala Phe Ser Gln Tyr Lys Lys Val Glu
            370                 375                 380

Leu Phe Pro Asn Gly Gln Ser Val Gly Glu Lys Ile Phe Lys Thr Ala
385                 390                 395                 400

Gly Phe Val Lys Pro Phe Thr Glu Ala Gln Leu Leu Cys Thr Gln Ala
            405                 410                 415

Gly Gly Gln Leu Ala Ser Pro Arg Ser Ala Ala Glu Asn Ala Ala Leu
            420                 425                 430

Gln Gln Leu Val Val Ala Lys Asn Glu Ala Ala Phe Leu Ser Met Thr
            435                 440                 445

Asp Ser Lys Thr Glu Gly Lys Phe Thr Tyr Pro Thr Gly Glu Ser Leu
450                 455                 460

Val Tyr Ser Asn Trp Ala Pro Gly Glu Pro Asn Asp Asp Gly Gly Ser
465                 470                 475                 480

Glu Asp Cys Val Glu Ile Phe Thr Asn Gly Lys Trp Asn Asp Arg Ala
            485                 490                 495

Cys Gly Glu Lys Arg Leu Val Val Cys Glu Phe
            500                 505

<210> SEQ ID NO 73
<211> LENGTH: 300
<212> TYPE: PRT
<213> ORGANISM: Artificial Sequence
<220> FEATURE:
<223> OTHER INFORMATION: Fusion protein

<400> SEQUENCE: 73

Met Gly His His His His His His Met Ser His Thr Thr Pro Trp Thr
1               5                   10                  15

Asn Pro Gly Leu Ala Glu Asn Phe Met Asn Ser Phe Met Gln Gly Leu
            20                  25                  30

Ser Ser Met Pro Gly Phe Thr Ala Ser Gln Leu Asp Lys Met Ser Thr
            35                  40                  45

```
Ile Ala Gln Ser Met Val Gln Ser Ile Gln Ser Leu Ala Ala Gln Gly
    50                  55                  60

Arg Thr Ser Pro Asn Asp Leu Gln Ala Leu Asn Met Ala Phe Ala Ser
65                  70                  75                  80

Ser Met Ala Glu Ile Ala Ala Ser Glu Glu Gly Gly Gly Ser Leu Ser
                85                  90                  95

Thr Lys Thr Ser Ser Ile Ala Ser Ala Met Ser Asn Ala Phe Leu Gln
            100                 105                 110

Thr Thr Gly Val Val Asn Gln Pro Phe Ile Asn Glu Ile Thr Gln Leu
                115                 120                 125

Val Ser Met Phe Ala Gln Ala Gly Met Asn Asp Val Ser Ala Gly Asn
130                 135                 140

Ser Leu Glu Ala Leu Phe Gln Gly Ala His Leu Asp Glu Glu Leu Gln
145                 150                 155                 160

Ala Thr Leu His Asp Phe Arg His Gln Ile Leu Gln Thr Arg Gly Ala
                165                 170                 175

Leu Ser Leu Gln Gly Ser Ile Met Thr Val Gly Glu Lys Val Phe Ser
                180                 185                 190

Ser Asn Gly Gln Ser Ile Thr Phe Asp Ala Ile Gln Glu Ala Cys Ala
            195                 200                 205

Arg Ala Gly Gly Arg Ile Ala Val Pro Arg Asn Pro Glu Glu Asn Glu
210                 215                 220

Ala Ile Ala Ser Phe Val Lys Lys Tyr Asn Thr Tyr Ala Tyr Val Gly
225                 230                 235                 240

Leu Thr Glu Gly Pro Ser Pro Gly Asp Phe Arg Tyr Ser Asp Gly Thr
                245                 250                 255

Pro Val Asn Tyr Thr Asn Trp Tyr Arg Gly Glu Pro Ala Gly Arg Gly
                260                 265                 270

Lys Glu Gln Cys Val Glu Met Tyr Thr Asp Gly Gln Trp Asn Asp Arg
            275                 280                 285

Asn Cys Leu Tyr Ser Arg Leu Thr Ile Cys Glu Phe
290                 295                 300

<210> SEQ ID NO 74
<211> LENGTH: 300
<212> TYPE: PRT
<213> ORGANISM: Artificial Sequence
<220> FEATURE:
<223> OTHER INFORMATION: Fusion protein

<400> SEQUENCE: 74

Met Gly His His His His His His Met Ser His Thr Thr Pro Trp Thr
1               5                   10                  15

Asn Pro Gly Leu Ala Glu Asn Phe Met Asn Ser Phe Met Gln Gly Leu
                20                  25                  30

Ser Ser Met Pro Gly Phe Thr Ala Ser Gln Leu Asp Lys Met Ser Thr
            35                  40                  45

Ile Ala Gln Ser Met Val Gln Ser Ile Gln Ser Leu Ala Ala Gln Gly
    50                  55                  60

Arg Thr Ser Pro Asn Asp Leu Gln Ala Leu Asn Met Ala Phe Ala Ser
65                  70                  75                  80

Ser Met Ala Glu Ile Ala Ala Ser Glu Glu Gly Gly Gly Ser Leu Ser
                85                  90                  95

Thr Lys Thr Ser Ser Ile Ala Ser Ala Met Ser Asn Ala Phe Leu Gln
            100                 105                 110
```

```
Thr Thr Gly Val Val Asn Gln Pro Phe Ile Asn Glu Ile Thr Gln Leu
            115                 120                 125

Val Ser Met Phe Ala Gln Ala Gly Met Asn Asp Val Ser Ala Gly Asn
    130                 135                 140

Ser Leu Glu Ala Leu Phe Gln Gly Ala His Leu Asp Glu Glu Leu Gln
145                 150                 155                 160

Ala Thr Leu His Asp Phe Arg His Gln Ile Leu Gln Thr Arg Gly Ala
                165                 170                 175

Leu Ser Leu Gln Gly Ser Ile Met Thr Val Gly Glu Lys Val Phe Ser
            180                 185                 190

Ser Asn Gly Gln Ser Ile Thr Phe Asp Ala Ile Gln Glu Ala Cys Ala
        195                 200                 205

Arg Ala Gly Gly Arg Ile Ala Val Pro Arg Asn Pro Glu Glu Asn Glu
    210                 215                 220

Ala Ile Ala Ser Phe Val Lys Lys Tyr Asn Thr Tyr Ala Tyr Val Gly
225                 230                 235                 240

Leu Thr Glu Gly Pro Ser Pro Gly Asp Phe Arg Tyr Ser Asp Gly Thr
                245                 250                 255

Pro Val Asn Tyr Thr Asn Trp Tyr Arg Gly Glu Pro Ala Gly Arg Gly
            260                 265                 270

Lys Glu Gln Cys Val Glu Met Tyr Thr Asp Gly Gln Trp Asn Asp Arg
        275                 280                 285

Asn Cys Leu Tyr Ser Arg Leu Thr Ile Cys Glu Phe
    290                 295                 300

<210> SEQ ID NO 75
<211> LENGTH: 304
<212> TYPE: PRT
<213> ORGANISM: Artificial Sequence
<220> FEATURE:
<223> OTHER INFORMATION: Fusion protein

<400> SEQUENCE: 75

Met Gly His His His His His Met Ser His Thr Thr Pro Trp Thr
1               5                   10                  15

Asn Pro Gly Leu Ala Glu Asn Phe Met Asn Ser Phe Met Gln Gly Leu
            20                  25                  30

Ser Ser Met Pro Gly Phe Thr Ala Ser Gln Leu Asp Lys Met Ser Thr
        35                  40                  45

Ile Ala Gln Ser Met Val Gln Ser Ile Gln Ser Leu Ala Ala Gln Gly
    50                  55                  60

Arg Thr Ser Pro Asn Asp Leu Gln Ala Leu Asn Met Ala Phe Ala Ser
65                  70                  75                  80

Ser Met Ala Glu Ile Ala Ala Ser Glu Glu Gly Gly Gly Ser Leu Ser
                85                  90                  95

Thr Lys Thr Ser Ser Ile Ala Ser Ala Met Ser Asn Ala Phe Leu Gln
            100                 105                 110

Thr Thr Gly Val Val Asn Gln Pro Phe Ile Asn Glu Ile Thr Gln Leu
        115                 120                 125

Val Ser Met Phe Ala Gln Ala Gly Met Asn Asp Val Ser Ala Gly Asn
    130                 135                 140

Ser Leu Glu Ala Leu Phe Gln Gly Val Ala Ser Leu Arg Gln Gln Val
145                 150                 155                 160

Glu Ala Leu Gln Gly Gln Val Gln His Leu Gln Ala Ala Phe Ser Gln
                165                 170                 175
```

Tyr Lys Lys Val Glu Leu Phe Pro Asn Gly Gln Ser Val Gly Glu Lys
            180                 185                 190

Ile Phe Lys Thr Ala Gly Phe Val Lys Pro Phe Thr Glu Ala Gln Leu
        195                 200                 205

Leu Cys Thr Gln Ala Gly Gly Gln Leu Ala Ser Pro Arg Ser Ala Ala
    210                 215                 220

Glu Asn Ala Ala Leu Gln Gln Leu Val Val Ala Lys Asn Glu Ala Ala
225                 230                 235                 240

Phe Leu Ser Met Thr Asp Ser Lys Thr Glu Gly Lys Phe Thr Tyr Pro
                245                 250                 255

Thr Gly Glu Ser Leu Val Tyr Ser Asn Trp Ala Pro Gly Glu Pro Asn
            260                 265                 270

Asp Asp Gly Gly Ser Glu Asp Cys Val Glu Ile Phe Thr Asn Gly Lys
        275                 280                 285

Trp Asn Asp Arg Ala Cys Gly Glu Lys Arg Leu Val Val Cys Glu Phe
    290                 295                 300

<210> SEQ ID NO 76
<211> LENGTH: 1140
<212> TYPE: DNA
<213> ORGANISM: Artificial Sequence
<220> FEATURE:
<223> OTHER INFORMATION: Fusion protein

<400> SEQUENCE: 76
atgggccatc atcatcatca tcatatgtca cacactacac catggacaaa cccaggactc      60
gcagaaaact tcatgaacag tttcatgcaa ggcctgagct cgatgccagg tttcacggca     120
agccaattgg ataagatgtc aaccatcgca caatccatgg tacagtcaat acaatccttg     180
gcggcacaag gcaggacatc accgaatgac ctgcaggccc ttaacatggc ttttgcatct     240
tcgatggcag aaatcgcggc atccgaagaa ggaggggggaa gcctttccac caaaactagc     300
tctatagcca gtgcaatgtc caacgcgttt ctgcaaacaa ctggagtggt aaaccaaccg     360
ttcataaatg aaataactca gctcgttagc atgtttgctc aagcaggtat gaatgatgtc     420
agtgctggga attcactgga agcgctgttc cagggcgaag tgaaggacgt tgtgttggga     480
agccctggta tccccggcac tcctggatcc cacggcctgc aggcaggga cgggagagat     540
ggtctcaaag gagaccctgg ccctccaggc cccatgggtc cgcctggaga atgccatgt      600
cctcctggaa atgatgggct gcctggagcc ctggtatcc ctggagagtg tggagagaag     660
ggggagcctg gcgagagggg ccctccaggg cttccagctc atctagatga ggagctccaa     720
gccacactcc acgactttag acatcaaatc ctgcagacaa ggggagccct cagtctgcag     780
ggctccataa tgacggtagg agagaaggtc ttctccagca atgggcagtc catcacttt      840
gatgccattc aggaggcatg tgccagagca ggcggccgca ttgctgtccc aaggaatcca     900
gaggaaaatg aggccattgc aagcttcgtg aagaagtaca acacatatgc ctatgtaggc     960
ctgactgagg gtcccagccc tggagacttc cgctactcag acgggacccc tgtaaactac    1020
accaactggt accgagggga gcccgcaggt cggggaaaag agcagtgtgt ggagatgtac    1080
acagatgggc agtggaatga caggaactgc ctgtactccc gactgaccat ctgtgagttc    1140

<210> SEQ ID NO 77
<211> LENGTH: 1140
<212> TYPE: DNA
<213> ORGANISM: Artificial Sequence
<220> FEATURE:
<223> OTHER INFORMATION: Fusion protein

<400> SEQUENCE: 77

```
atgggccatc atcatcatca tcatatgtca cacactacac catggacaaa cccaggactc      60
gcagaaaact tcatgaacag tttcatgcaa ggcctgagct cgatgccagg tttcacggca     120
agccaattgg ataagatgtc aaccatcgca caatccatgg tacagtcaat acaatccttg     180
gcggcacaag gcaggacatc accgaatgac ctgcaggccc ttaacatggc ttttgcatct     240
tcgatggcag aaatcgcggc atccgaagaa gaggggggaa gcctttccac caaaactagc     300
tctatagcca gtgcaatgtc caacgcgttt ctgcaaacaa ctggagtggt aaaccaaccg     360
ttcataaatg aaataactca gctcgttagc atgtttgctc aagcaggtat gaatgatgtc     420
agtgctggga attcactgga agcgctgttc cagggcgaag tgaaggacgt ttgtgttgga     480
agccctggta tccccggcac tcctggatcc acggcctgc caggcaggga cgggagagat     540
ggtgtcaaag gagaccctgg ccctccaggc ccatgggtc cgcctggaga acaccatgt      600
cctcctggga taatgggct gcctggagcc cctggtgtcc ctggagagcg tggagagaag     660
ggggagcctg cgagagagg ccctccaggg cttccagctc atctagatga ggagctccaa     720
gccacactcc acgacttcag acatcaaatc ctgcagacaa gggagcccct cagtctgcag     780
ggctccataa tgacagtagg agagaaggtc ttctccagca atgggcagtc catcactttt     840
gatgccattc aggaggcatg tgccagagca ggcggccgca ttgctgtccc aaggaatcca     900
gaggaaaatg aggccattgc aagcttcgtg aagaagtaca acacatatgc ctatgtaggc     960
ctgactgagg gtcccagccc tggagacttc cgctactcag atgggacccc tgtaaactac    1020
accaactggt accgagggga gcctgcaggt cggggaaaag agcagtgtgt ggagatgtac    1080
acagatgggc agtggaatga caggaactgc ctgtactccc gactgaccat ctgtgagttc    1140
```

<210> SEQ ID NO 78
<211> LENGTH: 1521
<212> TYPE: DNA
<213> ORGANISM: Artificial Sequence
<220> FEATURE:
<223> OTHER INFORMATION: Fusion protein

<400> SEQUENCE: 78

```
atgggccatc atcatcatca tcatatgtca cacactacac catggacaaa cccaggactc      60
gcagaaaact tcatgaacag tttcatgcaa ggcctgagct cgatgccagg tttcacggca     120
agccaattgg ataagatgtc aaccatcgca caatccatgg tacagtcaat acaatccttg     180
gcggcacaag gcaggacatc accgaatgac ctgcaggccc ttaacatggc ttttgcatct     240
tcgatggcag aaatcgcggc atccgaagaa gaggggggaa gcctttccac caaaactagc     300
tctatagcca gtgcaatgtc caacgcgttt ctgcaaacaa ctggagtggt aaaccaaccg     360
ttcataaatg aaataactca gctcgttagc atgtttgctc aagcaggtat gaatgatgtc     420
agtgctggga attcactgga agcgctgttc cagggcgcag aaatgaagac ctactcccac     480
agaacaatgc ccagtgcttg caccctggtc atgtgtagct cagtggagag tggcctgcct     540
ggtcgcgatg gacgggatgg gagagagggc cctcggggcg agaaggggga cccaggtttg     600
ccaggagctg cagggcaagc agggatgcct ggacaagctg cccagttggg ccccaagggg     660
gacaatggct ctgttggaga acctggacca agggagacag ctgggccaag tggacctcca     720
ggacctcccg gtgtgcctgg tccagctgga agagaaggtc ccctggggaa gcagggggaac     780
ataggacctc agggcaagcc aggcccaaaa ggagaagctg ggcccaaagg agaagtaggt    840
```

| | |
|---|---|
| gccccaggca tgcagggctc ggcaggggca agaggcctcg caggccctaa gggagagcga | 900 |
| ggtgtccctg gtgagcgtgg agtccctgga acacagggg cagcagggtc tgctggagcc | 960 |
| atgggtcccc agggaagtcc aggtgccagg gaccccccgg gattgaaggg ggacaaaggc | 1020 |
| attcctggag acaaaggagc aaagggagaa agtgggcttc cagatgttgc ttctctgagg | 1080 |
| cagcaggttg aggccttaca gggacaagta cagcacctcc aggctgcttt ctctcagtat | 1140 |
| aagaaagttg agctcttccc aaatggccaa agtgtcgggg agaagatttt caagacagca | 1200 |
| ggctttgtaa aaccatttac ggaggcacag ctgctgtgca cacaggctgg tggacagttg | 1260 |
| gcctctccac gctctgccgc tgagaatgcc gccttgcaac agctggtcgt agctaagaac | 1320 |
| gaggctgctt tcctgagcat gactgattcc aagacagagg gcaagttcac ctaccccaca | 1380 |
| ggagagtccc tggtctattc caactgggcc caggggagc caacgatga tggcgggtca | 1440 |
| gaggactgtg tggagatctt caccaatggc aagtggaatg cagggcttg tggagaaaag | 1500 |
| cgtcttgtgg tctgcgagtt c | 1521 |

<210> SEQ ID NO 79
<211> LENGTH: 900
<212> TYPE: DNA
<213> ORGANISM: Artificial Sequence
<220> FEATURE:
<223> OTHER INFORMATION: Fusion protein

<400> SEQUENCE: 79

| | |
|---|---|
| atgggccatc atcatcatca tcatatgtca cacactacac catggacaaa cccaggactc | 60 |
| gcagaaaact tcatgaacag tttcatgcaa ggcctgagct cgatgccagg tttcacggca | 120 |
| agccaattgg ataagatgtc aaccatcgca caatccatgg tacagtcaat acaatccttg | 180 |
| gcggcacaag gcaggacatc accgaatgac ctgcaggccc ttaacatggc ttttgcatct | 240 |
| tcgatggcag aaatcgcggc atccgaagaa ggaggggggaa gcctttccac caaaactagc | 300 |
| tctatagcca gtgcaatgtc caacgcgttt ctgcaaacaa ctggagtggt aaaccaaccg | 360 |
| ttcataaatg aaataactca gctcgttagc atgtttgctc aagcaggtat gaatgatgtc | 420 |
| agtgctggga attcactgga agcgctgttc caggcgctc atctagatga ggagctccaa | 480 |
| gccacactcc acgactttag acatcaaatc ctgcagacaa ggggagccct cagtctgcag | 540 |
| ggctccataa tgacggtagg agagaaggtc ttctccagca atgggcagtc catcactttt | 600 |
| gatgccattc aggaggcatg tgccagagca ggcggccgca ttgctgtccc aaggaatcca | 660 |
| gaggaaaatg aggccattgc aagcttcgtg aagaagtaca acacatatgc ctatgtaggc | 720 |
| ctgactgagg gtcccagccc tggagacttc cgctactcag acgggacccc tgtaaactac | 780 |
| accaactggt accgagggga gcccgcaggt cggggaaaag agcagtgtgt ggagatgtac | 840 |
| acagatgggc agtggaatga caggaactgc ctgtactccc gactgaccat ctgtgagttc | 900 |

<210> SEQ ID NO 80
<211> LENGTH: 900
<212> TYPE: DNA
<213> ORGANISM: Artificial Sequence
<220> FEATURE:
<223> OTHER INFORMATION: Fusion protein

<400> SEQUENCE: 80

| | |
|---|---|
| atgggccatc atcatcatca tcatatgtca cacactacac catggacaaa cccaggactc | 60 |
| gcagaaaact tcatgaacag tttcatgcaa ggcctgagct cgatgccagg tttcacggca | 120 |
| agccaattgg ataagatgtc aaccatcgca caatccatgg tacagtcaat acaatccttg | 180 |

```
gcggcacaag gcaggacatc accgaatgac ctgcaggccc ttaacatggc ttttgcatct    240
tcgatggcag aaatcgcggc atccgaagaa ggaggggggaa gcctttccac caaaactagc    300
tctatagcca gtgcaatgtc caacgcgttt ctgcaaacaa ctggagtggt aaaccaaccg    360
ttcataaatg aaataactca gctcgttagc atgtttgctc aagcaggtat gaatgatgtc    420
agtgctggga attcactgga agcgctgttc cagggcgctc atctagatga ggagctccaa    480
gccacactcc acgacttcag acatcaaatc ctgcagacaa gggagcccct cagtctgcag    540
ggctccataa tgacagtagg agagaaggtc ttctccagca atgggcagtc catcactttt    600
gatgccattc aggaggcatg tgccagagca ggcggccgca ttgctgtccc aaggaatcca    660
gaggaaaatg aggccattgc aagcttcgtg aagaagtaca acacatatgc ctatgtaggc    720
ctgactgagg gtcccagccc tggagacttc cgctactcag atgggacccc tgtaaactac    780
accaactggt accgagggga gcctgcaggt cggggaaaag agcagtgtgt ggagatgtac    840
acagatgggc agtggaatga caggaactgc ctgtactccc gactgaccat ctgtgagttc    900
```

<210> SEQ ID NO 81
<211> LENGTH: 912
<212> TYPE: DNA
<213> ORGANISM: Artificial Sequence
<220> FEATURE:
<223> OTHER INFORMATION: Fusion protein

<400> SEQUENCE: 81

```
atgggccatc atcatcatca tcatatgtca cacactacac catggacaaa cccaggactc     60
gcagaaaact tcatgaacag tttcatgcaa ggcctgagct cgatgccagg tttcacggca    120
agccaattgg ataagatgtc aaccatcgca caatccatgg tacagtcaat acaatccttg    180
gcggcacaag gcaggacatc accgaatgac ctgcaggccc ttaacatggc ttttgcatct    240
tcgatggcag aaatcgcggc atccgaagaa ggaggggggaa gcctttccac caaaactagc    300
tctatagcca gtgcaatgtc caacgcgttt ctgcaaacaa ctggagtggt aaaccaaccg    360
ttcataaatg aaataactca gctcgttagc atgtttgctc aagcaggtat gaatgatgtc    420
agtgctggga attcactgga agcgctgttc cagggcgttg cttctctgag gcagcaggtt    480
gaggccttac agggacaagt acagcaccct caggctgctt tctctcagta taagaaagtt    540
gagctcttcc caaatggcca aagtgtcggg gagaagattt caagacagc aggctttgta    600 aaaccattta cggaggcaca gctgctgtgc acacaggctg gtggacagtt ggcctctcca    660
cgctctgccg ctgagaatgc cgccttgcaa cagctggtcg tagctaagaa cgaggctgct    720
ttcctgagca tgactgattc caagacagag ggcaagttca cctaccccac aggagagtcc    780
ctggtctatt ccaactgggc cccaggggag cccaacgatg atggcgggtc agaggactgt    840
gtggagatct tcaccaatgg caagtggaat gacagggctt gtggagaaaa gcgtcttgtg    900
gtctgcgagt tc                                                        912
```

<210> SEQ ID NO 82
<211> LENGTH: 193
<212> TYPE: PRT
<213> ORGANISM: Artificial Sequence
<220> FEATURE:
<223> OTHER INFORMATION: Fusion protein

<400> SEQUENCE: 82

```
Met Gly His His His His His His Met Ser His Thr Thr Pro Trp Thr
1               5                   10                  15
```

Asn Pro Gly Leu Ala Glu Asn Phe Met Asn Ser Phe Met Gln Gly Leu
                20                  25                  30

Ser Ser Met Pro Gly Phe Thr Ala Ser Gln Leu Asp Lys Met Ser Thr
            35                  40                  45

Ile Ala Gln Ser Met Val Gln Ser Ile Gln Ser Leu Ala Ala Gln Gly
 50                  55                  60

Arg Thr Ser Pro Asn Asp Leu Gln Ala Leu Asn Met Ala Phe Ala Ser
 65                  70                  75                  80

Ser Met Ala Glu Ile Ala Ala Ser Glu Glu Gly Gly Ser Leu Ser
                85                  90                  95

Thr Lys Thr Ser Ser Ile Ala Ser Ala Met Ser Asn Ala Phe Leu Gln
                100                 105                 110

Thr Thr Gly Val Val Asn Gln Pro Phe Ile Asn Glu Ile Thr Gln Leu
            115                 120                 125

Val Ser Met Phe Ala Gln Ala Gly Met Asn Asp Val Ser Ala Gly Asn
130                 135                 140

Ser Leu Val Pro Arg Gly Ser Asp Ala Glu Phe Arg His Asp Ser Gly
145                 150                 155                 160

Tyr Glu Val His His Gln Lys Leu Val Phe Phe Ala Glu Asp Val Gly
                165                 170                 175

Ser Asn Lys Gly Ala Ile Ile Gly Leu Met Val Gly Gly Val Val Ile
            180                 185                 190

Ala

<210> SEQ ID NO 83
<211> LENGTH: 579
<212> TYPE: DNA
<213> ORGANISM: Artificial Sequence
<220> FEATURE:
<223> OTHER INFORMATION: Fusion protein

<400> SEQUENCE: 83
atgggccatc atcatcatca tcatatgtca cacactacac catggacaaa cccaggactc      60
gcagaaaact tcatgaacag tttcatgcaa ggcctgagct cgatgccagg tttcacggca     120
agccaattgg ataagatgtc aaccatcgca caatccatgg tacagtcaat acaatccttg     180
gcggcacaag gcaggacatc accgaatgac ctgcaggccc ttaacatggc ttttgcatct     240
tcgatggcag aaatcgcggc atccgaagaa ggaggggaa gccttccac caaaactagc      300 tctatagcca gtgcaatgtc caacgcgttt ctgcaaacaa ctggagtggt aaaccaaccg     360
ttcataaatg aaataactca gctcgttagc atgtttgctc aagcaggtat gaatgatgtc     420
agtgctggga attccctggt gccacgcggt tctgacgctg aattccgtca cgactctggt     480
tacgaagttc accaccagaa gctggtgttc ttcgctgaag acgtgggttc taacaagggt     540
gctatcatcg gtctgatggt tggtggcgtt gtgatcgcg                           579

<210> SEQ ID NO 84
<211> LENGTH: 188
<212> TYPE: PRT
<213> ORGANISM: Artificial Sequence
<220> FEATURE:
<223> OTHER INFORMATION: Fusion protein

<400> SEQUENCE: 84

Met Gly His His His His His His Met Ser His Thr Thr Pro Trp Thr
 1               5                   10                  15

```
Asn Pro Gly Leu Ala Glu Asn Phe Met Asn Ser Phe Met Gln Gly Leu
            20                  25                  30

Ser Ser Met Pro Gly Phe Thr Ala Ser Gln Leu Asp Lys Met Ser Thr
        35                  40                  45

Ile Ala Gln Ser Met Val Gln Ser Ile Gln Ser Leu Ala Ala Gln Gly
    50                  55                  60

Arg Thr Ser Pro Asn Asp Leu Gln Ala Leu Asn Met Ala Phe Ala Ser
65                  70                  75                  80

Ser Met Ala Glu Ile Ala Ala Ser Glu Gly Gly Gly Ser Leu Ser
                85                  90                  95

Thr Lys Thr Ser Ser Ile Ala Ser Ala Met Ser Asn Ala Phe Leu Gln
                100                 105                 110

Thr Thr Gly Val Val Asn Gln Pro Phe Ile Asn Glu Ile Thr Gln Leu
            115                 120                 125

Val Ser Met Phe Ala Gln Ala Gly Met Asn Asp Val Ser Ala Gly Asn
    130                 135                 140

Ser Leu Val Pro Arg Gly Ser Lys Cys Asn Thr Ala Thr Cys Ala Thr
145                 150                 155                 160

Gln Arg Leu Ala Asn Phe Leu Val His Ser Ser Asn Asn Phe Gly Ala
                165                 170                 175

Ile Leu Ser Ser Thr Asn Val Gly Ser Asn Thr Tyr
            180                 185
```

<210> SEQ ID NO 85
<211> LENGTH: 564
<212> TYPE: DNA
<213> ORGANISM: Artificial Sequence
<220> FEATURE:
<223> OTHER INFORMATION: Fusion protein

<400> SEQUENCE: 85

```
atgggccatc atcatcatca tcatatgtca cacactacac catggacaaa cccaggactc      60
gcagaaaact tcatgaacag tttcatgcaa ggcctgagct cgatgccagg tttcacggca     120
agccaattgg ataagatgtc aaccatcgca caatccatgg tacagtcaat acaatccttg     180
gcggcacaag caggacatc accgaatgac ctgcaggccc ttaacatggc ttttgcatct     240
tcgatggcag aaatcgcggc atccgaagaa ggagggggaa gccttccac aaaactagc      300
tctatagcca gtgcaatgtc caacgcgttt ctgcaaacaa ctggagtggt aaaccaaccg     360
ttcataaatg aaataactca gctcgttagc atgtttgctc aagcaggtat gaatgatgtc     420
agtgctggga ttcctggt gccacgcggt tctaaatgca acactgccac atgtgcaacg      480
cagcgcctgg caatttttt agttcattcc agcaacaact tggtgccat tctctcatct      540
accaacgtgg gatccaatac atat                                            564
```

<210> SEQ ID NO 86
<211> LENGTH: 291
<212> TYPE: PRT
<213> ORGANISM: Artificial Sequence
<220> FEATURE:
<223> OTHER INFORMATION: Fusion protein

<400> SEQUENCE: 86

```
Met Gly His His His His His His Met Ser His Thr Thr Pro Trp Thr
1               5                   10                  15

Asn Pro Gly Leu Ala Glu Asn Phe Met Asn Ser Phe Met Gln Gly Leu
            20                  25                  30
```

```
Ser Ser Met Pro Gly Phe Thr Ala Ser Gln Leu Asp Asp Met Ser Thr
        35                  40                  45

Ile Ala Gln Ser Met Val Gln Ser Ile Gln Ser Leu Ala Ala Gln Gly
 50                  55                  60

Arg Thr Ser Pro Asn Lys Leu Gln Ala Leu Asn Met Ala Phe Ala Ser
 65                  70                  75                  80

Ser Met Ala Glu Ile Ala Ala Ser Glu Glu Gly Gly Ser Leu Ser
                 85                  90                  95

Thr Lys Thr Ser Ser Ile Ala Ser Ala Met Ser Asn Ala Phe Leu Gln
                100                 105                 110

Thr Thr Gly Val Val Asn Gln Pro Phe Ile Asn Glu Ile Thr Gln Leu
                115                 120                 125

Val Ser Met Phe Ala Gln Ala Gly Met Asn Asp Val Ser Ala Gly Asn
130                 135                 140

Ser Leu Val Pro Arg Gly Ser Gln Val Leu Ser Tyr Lys Glu Ala Val
145                 150                 155                 160

Leu Arg Ala Ile Asp Gly Ile Asn Gln Arg Ser Ser Asp Ala Asn Leu
                165                 170                 175

Tyr Arg Leu Leu Asp Leu Asp Pro Arg Pro Thr Met Asp Gly Asp Pro
                180                 185                 190

Asp Thr Pro Lys Pro Val Ser Phe Thr Val Lys Glu Thr Val Cys Pro
                195                 200                 205

Arg Thr Thr Gln Gln Ser Pro Glu Asp Cys Asp Phe Lys Lys Asp Gly
                210                 215                 220

Leu Val Lys Arg Cys Met Gly Thr Val Thr Leu Asn Gln Ala Arg Gly
225                 230                 235                 240

Ser Phe Asp Ile Ser Cys Asp Lys Asp Asn Lys Arg Phe Ala Leu Leu
                245                 250                 255

Gly Asp Phe Phe Arg Lys Ser Lys Glu Lys Ile Gly Lys Glu Phe Lys
                260                 265                 270

Arg Ile Val Gln Arg Ile Lys Asp Phe Leu Arg Asn Leu Val Pro Arg
                275                 280                 285

Thr Glu Ser
   290

<210> SEQ ID NO 87
<211> LENGTH: 291
<212> TYPE: PRT
<213> ORGANISM: Artificial Sequence
<220> FEATURE:
<223> OTHER INFORMATION: Fusion protein

<400> SEQUENCE: 87

Met Gly His His His His His His Met Ser His Thr Thr Pro Trp Thr
  1               5                  10                  15

Asn Pro Gly Leu Ala Glu Asn Phe Met Asn Ser Phe Met Gln Gly Leu
                 20                  25                  30

Ser Ser Met Pro Gly Phe Thr Ala Ser Gln Leu Asp Lys Met Ser Thr
        35                  40                  45

Ile Ala Gln Ser Met Val Gln Ser Ile Gln Ser Leu Ala Ala Gln Gly
 50                  55                  60

Arg Thr Ser Pro Asn Asp Leu Gln Ala Leu Asn Met Ala Phe Ala Ser
 65                  70                  75                  80

Ser Met Ala Glu Ile Ala Ala Ser Glu Glu Gly Gly Ser Leu Ser
                 85                  90                  95
```

| | | | | | | | | | | | |
|---|---|---|---|---|---|---|---|---|---|---|---|
|Thr|Lys|Thr|Ser|Ser|Ile|Ala|Ser|Ala|Met|Ser|Asn|Ala|Phe|Leu|Gln|
| | | |100| | | |105| | | |110| | | | |

Thr Lys Thr Ser Ser Ile Ala Ser Ala Met Ser Asn Ala Phe Leu Gln
                100                 105                 110

Thr Thr Gly Val Val Asn Gln Pro Phe Ile Asn Glu Ile Thr Gln Leu
        115                 120                 125

Val Ser Met Phe Ala Gln Ala Gly Met Asn Asp Val Ser Ala Gly Asn
    130                 135                 140

Ser Leu Val Pro Arg Gly Ser Gln Val Leu Ser Tyr Lys Glu Ala Val
145                 150                 155                 160

Leu Arg Ala Ile Asp Gly Ile Asn Gln Arg Ser Ser Asp Ala Asn Leu
                165                 170                 175

Tyr Arg Leu Leu Asp Leu Asp Pro Arg Pro Thr Met Asp Gly Asp Pro
            180                 185                 190

Asp Thr Pro Lys Pro Val Ser Phe Thr Val Lys Glu Thr Val Cys Pro
        195                 200                 205

Arg Thr Thr Gln Gln Ser Pro Glu Asp Cys Asp Phe Lys Lys Asp Gly
    210                 215                 220

Leu Val Lys Arg Cys Met Gly Thr Val Thr Leu Asn Gln Ala Arg Gly
225                 230                 235                 240

Ser Phe Asp Ile Ser Cys Asp Lys Asp Asn Lys Arg Phe Ala Leu Leu
                245                 250                 255

Gly Asp Phe Phe Arg Lys Ser Lys Glu Lys Ile Gly Lys Glu Phe Lys
            260                 265                 270

Arg Ile Val Gln Arg Ile Lys Asp Phe Leu Arg Asn Leu Val Pro Arg
        275                 280                 285

Thr Glu Ser
    290

<210> SEQ ID NO 88
<211> LENGTH: 873
<212> TYPE: DNA
<213> ORGANISM: Artificial Sequence
<220> FEATURE:
<223> OTHER INFORMATION: Fusion protein

<400> SEQUENCE: 88

| | |
|---|---|
|atgggccatc atcatcatca tcatatgtca cacactacac catggacaaa cccaggactc|60|
|gcagaaaact tcatgaacag tttcatgcaa ggcctgagct cgatgccagg tttcacggca|120|
|agccaattgg atgatatgtc aaccatcgca caatccatgg tacagtcaat acaatccttg|180|
|gcggcacaag gcaggacatc accgaataag ctgcaggccc ttaacatggc ttttgcatct|240|
|tcgatggcag aaatcgcggc atccgaagaa ggagggggaa gcctttccac caaaactagc|300|
|tctatagcca gtgcaatgtc caacgcgttt ctgcaaacaa ctggagtggt aaaccaaccg|360|
|ttcataaatg aaataactca gctcgttagc atgtttgctc aagcaggtat gaatgatgtc|420|
|agtgctggga attccctggt gccacgcggt tctcaggtcc tcagctacaa ggaagctgtg|480|
|cttcgtgcta tagatggcat caaccagcgg tcctcggatg ctaacctcta ccgcctcctg|540|
|gacctggacc ccaggcccac gatggatggg acccagaca cgccaaagcc tgtgagcttc|600|
|acagtgaagg agacagtgtg ccccaggacg acacagcagt caccagagga ttgtgacttc|660|
|aagaaggacg gcctggtgaa gcggtgtatg gggacagtga ccctcaacca ggccaggggc|720|
|tcctttgaca tcagttgtga taaggataac aagagatttg ccctgctggg tgatttcttc|780|
|cggaaatcta agagaagat tggcaaagag tttaaagaa ttgtccagag aatcaaggat|840|
|ttttttgcgga atcttgtacc caggacagag tcc|873|

<210> SEQ ID NO 89
<211> LENGTH: 873
<212> TYPE: DNA
<213> ORGANISM: Artificial Sequence
<220> FEATURE:
<223> OTHER INFORMATION: Fusion protein

<400> SEQUENCE: 89

```
atgggccatc atcatcatca tcatatgtca cacactacac catggacaaa cccaggactc      60
gcagaaaact tcatgaacag tttcatgcaa ggcctgagct cgatgccagg tttcacggca     120
agccaattgg ataagatgtc aaccatcgca aatccatgg tacagtcaat acaatccttg     180
gcggcacaag gcaggacatc accgaatgac ctgcaggccc ttaacatggc ttttgcatct     240
tcgatggcag aaatcgcggc atccgaagaa ggaggggggaa gcctttccac caaaactagc     300
tctatagcca gtgcaatgtc caacgcgttt ctgcaaacaa ctggagtggt aaaccaaccg     360
ttcataaatg aaataactca gctcgttagc atgtttgctc aagcaggtat gaatgatgtc     420
agtgctggga attccctggt gccacgcggt tctcaggtcc tcagctacaa ggaagctgtg     480
cttcgtgcta tagatggcat caaccagcgg tcctcggatg ctaacctcta ccgcctcctg     540
gacctggacc ccaggcccac gatggatggg gacccagaca cgccaaagcc tgtgagcttc     600
acagtgaagg agacagtgtg ccccaggacg acacagcagt caccagagga ttgtgacttc     660
aagaaggacg ggctggtgaa gcggtgtatg gggacagtga ccctcaacca ggccaggggc     720
tcctttgaca tcagttgtga taaggataac aagagatttg ccctgctggg tgatttcttc     780
cggaaatcta agagaagat tggcaaagag tttaaagaa ttgtccagag aatcaaggat     840
tttttgcgga atcttgtacc caggacagag tcc                                 873
```

<210> SEQ ID NO 90
<211> LENGTH: 787
<212> TYPE: PRT
<213> ORGANISM: Artificial Sequence
<220> FEATURE:
<223> OTHER INFORMATION: Fusion protein

<400> SEQUENCE: 90

```
Met Gly His His His His His His Met Ser His Thr Thr Pro Trp Thr
1               5                   10                  15

Asn Pro Gly Leu Ala Glu Asn Phe Met Asn Ser Phe Met Gln Gly Leu
            20                  25                  30

Ser Ser Met Pro Gly Phe Thr Ala Ser Gln Leu Asp Lys Met Ser Thr
        35                  40                  45

Ile Ala Gln Ser Met Val Gln Ser Ile Gln Ser Leu Ala Ala Gln Gly
    50                  55                  60

Arg Thr Ser Pro Asn Asp Leu Gln Ala Leu Asn Met Ala Phe Ala Ser
65                  70                  75                  80

Ser Met Ala Glu Ile Ala Ala Ser Glu Glu Gly Gly Gly Ser Leu Ser
                85                  90                  95

Thr Lys Thr Ser Ser Ile Ala Ser Ala Met Ser Asn Ala Phe Leu Gln
            100                 105                 110

Thr Thr Gly Val Val Asn Gln Pro Phe Ile Asn Glu Ile Thr Gln Leu
        115                 120                 125

Val Ser Met Phe Ala Gln Ala Gly Met Asn Asp Val Ser Ala Gly Asn
    130                 135                 140

Ser Leu Val Pro Arg Gly Ser Asn Ser Val Glu Arg Lys Ile Tyr Ile
145                 150                 155                 160
```

```
Pro Leu Asn Lys Thr Ala Pro Cys Val Arg Leu Leu Asn Ala Thr His
            165                 170                 175

Gln Ile Gly Cys Gln Ser Ser Ile Ser Gly Asp Thr Gly Val Ile His
            180                 185                 190

Val Val Glu Lys Glu Glu Asp Leu Gln Trp Val Leu Thr Asp Gly Pro
            195                 200                 205

Asn Pro Pro Tyr Met Val Leu Leu Glu Ser Lys His Phe Thr Arg Asp
            210                 215                 220

Leu Met Glu Lys Leu Lys Gly Arg Thr Ser Arg Ile Ala Gly Leu Ala
225                 230                 235                 240

Val Ser Leu Thr Lys Pro Ser Pro Ala Ser Gly Phe Ser Pro Ser Val
            245                 250                 255

Gln Cys Pro Asn Asp Gly Phe Gly Val Tyr Ser Asn Ser Tyr Gly Pro
            260                 265                 270

Glu Phe Ala His Cys Arg Glu Ile Gln Trp Asn Ser Leu Gly Asn Gly
            275                 280                 285

Leu Ala Tyr Glu Asp Phe Ser Phe Pro Ile Phe Leu Leu Glu Asp Glu
            290                 295                 300

Asn Glu Thr Lys Val Ile Lys Gln Cys Tyr Gln Asp His Asn Leu Ser
305                 310                 315                 320

Gln Asn Gly Ser Ala Pro Thr Phe Pro Leu Cys Ala Met Gln Leu Phe
            325                 330                 335

Ser His Met His Ala Val Ile Ser Thr Ala Thr Cys Met Arg Arg Ser
            340                 345                 350

Ser Ile Gln Ser Thr Phe Ser Ile Asn Pro Glu Ile Val Cys Asp Pro
            355                 360                 365

Leu Ser Asp Tyr Asn Val Trp Ser Met Leu Lys Pro Ile Asn Thr Thr
            370                 375                 380

Gly Thr Leu Lys Pro Asp Asp Arg Val Val Ala Ala Thr Arg Leu
385                 390                 395                 400

Asp Ser Arg Ser Phe Phe Trp Asn Val Ala Pro Gly Ala Glu Ser Ala
            405                 410                 415

Val Ala Ser Phe Val Thr Gln Leu Ala Ala Glu Ala Leu Gln Lys
            420                 425                 430

Ala Pro Asp Val Thr Thr Leu Pro Arg Asn Val Met Phe Val Phe Phe
            435                 440                 445

Gln Gly Glu Thr Phe Asp Tyr Ile Gly Ser Ser Arg Met Val Tyr Asp
            450                 455                 460

Met Glu Lys Gly Lys Phe Pro Val Gln Leu Glu Asn Val Asp Ser Phe
465                 470                 475                 480

Val Glu Leu Gly Gln Val Ala Leu Arg Thr Ser Leu Glu Leu Trp Met
            485                 490                 495

His Thr Asp Pro Val Ser Gln Lys Asn Glu Ser Val Arg Asn Gln Val
            500                 505                 510

Glu Asp Leu Leu Ala Thr Leu Glu Lys Ser Gly Ala Gly Val Pro Ala
            515                 520                 525

Val Ile Leu Arg Arg Pro Asn Gln Ser Gln Pro Leu Pro Pro Ser Ser
            530                 535                 540

Leu Gln Arg Phe Leu Arg Ala Arg Asn Ile Ser Gly Val Val Leu Ala
545                 550                 555                 560

Asp His Ser Gly Ala Phe His Asn Lys Tyr Tyr Gln Ser Ile Tyr Asp
            565                 570                 575
```

```
Thr Ala Glu Asn Ile Asn Val Ser Tyr Pro Glu Trp Leu Ser Pro Glu
            580                 585                 590

Glu Asp Leu Asn Phe Val Thr Asp Thr Ala Lys Ala Leu Ala Asp Val
            595                 600                 605

Ala Thr Val Leu Gly Arg Ala Leu Tyr Glu Leu Ala Gly Gly Thr Asn
        610                 615                 620

Phe Ser Asp Thr Val Gln Ala Asp Pro Gln Thr Val Thr Arg Leu Leu
625                 630                 635                 640

Tyr Gly Phe Leu Ile Lys Ala Asn Asn Ser Trp Phe Gln Ser Ile Leu
                645                 650                 655

Arg Gln Asp Leu Arg Ser Tyr Leu Gly Asp Gly Pro Leu Gln His Tyr
            660                 665                 670

Ile Ala Val Ser Ser Pro Thr Asn Thr Thr Tyr Val Val Gln Tyr Ala
        675                 680                 685

Leu Ala Asn Leu Thr Gly Thr Val Val Asn Leu Thr Arg Glu Gln Cys
    690                 695                 700

Gln Asp Pro Ser Lys Val Pro Ser Glu Asn Lys Asp Leu Tyr Glu Tyr
705                 710                 715                 720

Ser Trp Val Gln Gly Pro Leu His Ser Asn Glu Thr Asp Arg Leu Pro
                725                 730                 735

Arg Cys Val Arg Ser Thr Ala Arg Leu Ala Arg Ala Leu Ser Pro Ala
            740                 745                 750

Phe Glu Leu Ser Gln Trp Ser Ser Thr Glu Tyr Ser Thr Trp Thr Glu
        755                 760                 765

Ser Arg Trp Lys Asp Ile Arg Ala Arg Ile Phe Leu Ile Ala Ser Lys
770                 775                 780

Glu Leu Glu
785

<210> SEQ ID NO 91
<211> LENGTH: 2361
<212> TYPE: DNA
<213> ORGANISM: Artificial Sequence
<220> FEATURE:
<223> OTHER INFORMATION: Fusion protein

<400> SEQUENCE: 91
atgggccatc atcatcatca tcatatgtca cacactacac catggacaaa cccaggactc     60
gcagaaaact tcatgaacag tttcatgcaa ggcctgagct cgatgccagg tttcacggca    120
agccaattgg ataagatgtc aaccatcgca caatccatgg tacagtcaat acaatccttg    180
gcggcacaag gcaggacatc accgaatgac ctgcaggccc ttaacatggc ttttgcatct    240
tcgatggcag aaatcgcggc atccgaagaa ggaggggaa gccttccac caaaactagc    300 tctatagcca gtgcaatgtc caacgcgttt ctgcaaacaa ctggagtggt aaaccaaccg    360
ttcataaatg aaataactca gctcgttagc atgtttgctc aagcaggtat gaatgatgtc    420
agtgctggga attccctggt gccacgcggt tctaactcag tggagaggaa gatatatatc    480
cccttaaata aaacagctcc ctgtgttcgc ctgctcaacg ccactcatca gattggctgc    540
cagtcttcaa ttagtggaga cagggggtt atccacgtag tagagaaaga ggaggaccta    600
cagtgggtat tgactgatgg ccccaacccc ccttacatgg ttctgctgga gagcaagcat    660
tttaccaggg atttaatgga gaagctgaaa gggagaacca gccgaattgc tggtcttgca    720
gtgtccttga ccaagcccag tcctgcctca ggcttctctc ctagtgtaca gtgcccaaat    780
gatgggtttg gtgtttactc caattcctat gggccagagt ttgctcactg cagagaaata    840
```

```
cagtggaatt cgctgggcaa tggtttggct tatgaagact ttagtttccc catctttctt    900
cttgaagatg aaaatgaaac caaagtcatc aagcagtgct atcaagatca aacctgagt    960
cagaatggct cagcaccaac cttcccacta tgtgccatgc agctcttttc acacatgcat   1020
gctgtcatca gcactgccac ctgcatgcgg cgcagctcca tccaaagcac cttcagcatc   1080
aacccagaaa tcgtctgtga ccccctgtct gattacaatg tgtggagcat gctaaagcct   1140
ataaatacaa ctgggacatt aaagcctgac gacaggttg tggttgctgc cacccggctg    1200
gatagtcgtt ccttttcctg gaatgtggcc ccaggggctg aaagcgcagt ggcttccttt   1260
gtcacccagc tggctgctgc tgaagctttg caaaaggcac ctgatgtgac caccctgccc   1320
cgcaatgtca tgtttgtctt ctttcaaggg gaaacttttg actacattgg cagctcgagg   1380
atggtctacg atatggagaa gggcaagttt cccgtgcagt tagagaatgt tgactcattt   1440
gtggagctgg acaggtggcc cttaagaact tcattagagc tttggatgca cacagatcct   1500
gtttctcaga aaaatgagtc tgtacggaac caggtgagg atctcctggc acattggag    1560
aagagtggtg ctggtgtccc tgctgtcatc ctcaggaggc caaatcagtc ccagcctctc   1620
ccaccatctt ccctgcagcg atttcttcga gctcgaaaca tctctggcgt tgttctggct   1680
gaccactctg gtgccttcca taacaaatat taccagagta tttacgacac tgctgagaac   1740
attaatgtga gctatcccga atggctgagc cctgaagagg acctgaactt tgtaacagac   1800
actgccaagg ccctggcaga tgtggccacg gtgctgggac gtgctctgta tgagcttgca   1860
ggaggaacca acttcagcga cacagttcag gctgatcccc aaacggttac ccgcctgctc   1920
tatgggttcc tgattaaagc caacaactca tggttccagt ctatcctcag gcaggaccta   1980
aggtcctact gggtgacgg gcctcttcaa cattacatcg ctgtctccag ccccaccaac   2040
accacttatg ttgtacagta tgccttggca aatttgactg gcacagtggt caacctcacc   2100
cgagagcagt gccaggatcc aagtaaagtc ccaagtgaaa acaaggatct gtatgagtac   2160
tcatgggtcc agggcccttt gcattctaat gagacggacc gactcccccg tgtgtgcgt    2220
tctactgcac gattagccag ggccttgtct cctgcctttg aactgagtca gtggagctct   2280
actgaatact ctacatggac tgagagccgc tggaaagata tccgtgcccg gatatttctc   2340
atcgccagca aagagcttga g                                             2361
```

<210> SEQ ID NO 92
<211> LENGTH: 390
<212> TYPE: PRT
<213> ORGANISM: Artificial Sequence
<220> FEATURE:
<223> OTHER INFORMATION: Fusion protein

<400> SEQUENCE: 92

```
Met Gly His His His His His His Met Ser His Thr Thr Pro Trp Thr
1               5                   10                  15

Asn Pro Gly Leu Ala Glu Asn Phe Met Asn Ser Phe Met Gln Gly Leu
            20                  25                  30

Ser Ser Met Pro Gly Phe Thr Ala Ser Gln Leu Asp Asp Met Ser Thr
        35                  40                  45

Ile Ala Gln Ser Met Val Gln Ser Ile Gln Ser Leu Ala Ala Gln Gly
    50                  55                  60

Arg Thr Ser Pro Asn Lys Leu Gln Ala Leu Asn Met Ala Phe Ala Ser
65                  70                  75                  80

Ser Met Ala Glu Ile Ala Ala Ser Glu Glu Gly Gly Gly Ser Leu Ser
```

```
                    85                  90                  95
Thr Lys Thr Ser Ser Ile Ala Ser Ala Met Ser Asn Ala Phe Leu Gln
                100                 105                 110
Thr Thr Gly Val Val Asn Gln Pro Phe Ile Asn Glu Ile Thr Gln Leu
                115                 120                 125
Val Ser Met Phe Ala Gln Ala Gly Met Asn Asp Val Ser Ala Gly Asn
            130                 135                 140
Ser Leu Val Pro Arg Gly Ser Lys Gly Glu Glu Leu Phe Thr Gly Val
145                 150                 155                 160
Val Pro Ile Leu Val Glu Leu Asp Gly Asp Val Asn Gly His Lys Phe
                165                 170                 175
Ser Val Ser Gly Glu Gly Glu Gly Asp Ala Thr Tyr Gly Lys Leu Thr
                180                 185                 190
Leu Lys Phe Ile Cys Thr Thr Gly Lys Leu Pro Val Pro Trp Pro Thr
                195                 200                 205
Leu Val Thr Thr Leu Thr Tyr Gly Val Gln Cys Phe Ser Arg Tyr Pro
            210                 215                 220
Asp His Met Lys Gln His Asp Phe Phe Lys Ser Ala Met Pro Glu Gly
225                 230                 235                 240
Tyr Val Gln Glu Arg Thr Ile Phe Phe Lys Asp Asp Gly Asn Tyr Lys
                245                 250                 255
Thr Arg Ala Glu Val Lys Phe Glu Gly Asp Thr Leu Val Asn Arg Ile
                260                 265                 270
Glu Leu Lys Gly Ile Asp Phe Lys Glu Asp Gly Asn Ile Leu Gly His
            275                 280                 285
Lys Leu Glu Tyr Asn Tyr Asn Ser His Asn Val Tyr Ile Met Ala Asp
290                 295                 300
Lys Gln Lys Asn Gly Ile Lys Val Asn Phe Lys Ile Arg His Asn Ile
305                 310                 315                 320
Glu Asp Gly Ser Val Gln Leu Ala Asp His Tyr Gln Gln Asn Thr Pro
                325                 330                 335
Ile Gly Asp Gly Pro Val Leu Leu Pro Asp Asn His Tyr Leu Ser Thr
            340                 345                 350
Gln Ser Ala Leu Ser Lys Asp Pro Asn Glu Lys Arg Asp His Met Val
            355                 360                 365
Leu Leu Glu Phe Val Thr Ala Ala Gly Ile Thr Leu Gly Met Asp Glu
            370                 375                 380
Leu Tyr Lys Leu Ile Asn
385                 390

<210> SEQ ID NO 93
<211> LENGTH: 390
<212> TYPE: PRT
<213> ORGANISM: Artificial Sequence
<220> FEATURE:
<223> OTHER INFORMATION: Fusion protein

<400> SEQUENCE: 93

Met Gly His His His His His His Met Ser His Thr Thr Pro Trp Thr
1               5                   10                  15
Asn Pro Gly Leu Ala Glu Asn Phe Met Asn Ser Phe Met Gln Gly Leu
                20                  25                  30
Ser Ser Met Pro Gly Phe Thr Ala Ser Gln Leu Asp Lys Met Ser Thr
            35                  40                  45
Ile Ala Gln Ser Met Val Gln Ser Ile Gln Ser Leu Ala Ala Gln Gly
```

```
                50                  55                  60
Arg Thr Ser Pro Asn Asp Leu Gln Ala Leu Asn Met Ala Phe Ala Ser
 65                  70                  75                  80

Ser Met Ala Glu Ile Ala Ala Ser Glu Glu Gly Gly Ser Leu Ser
                 85                  90                  95

Thr Lys Thr Ser Ser Ile Ala Ser Ala Met Ser Asn Ala Phe Leu Gln
                100                 105                 110

Thr Thr Gly Val Val Asn Gln Pro Phe Ile Asn Glu Ile Thr Gln Leu
            115                 120                 125

Val Ser Met Phe Ala Gln Ala Gly Met Asn Asp Val Ser Ala Gly Asn
        130                 135                 140

Ser Leu Val Pro Arg Gly Ser Lys Gly Glu Glu Leu Phe Thr Gly Val
145                 150                 155                 160

Val Pro Ile Leu Val Glu Leu Asp Gly Asp Val Asn Gly His Lys Phe
                165                 170                 175

Ser Val Ser Gly Glu Gly Glu Gly Asp Ala Thr Tyr Gly Lys Leu Thr
            180                 185                 190

Leu Lys Phe Ile Cys Thr Thr Gly Lys Leu Pro Val Pro Trp Pro Thr
        195                 200                 205

Leu Val Thr Thr Leu Thr Tyr Gly Val Gln Cys Phe Ser Arg Tyr Pro
210                 215                 220

Asp His Met Lys Gln His Asp Phe Phe Lys Ser Ala Met Pro Glu Gly
225                 230                 235                 240

Tyr Val Gln Glu Arg Thr Ile Phe Phe Lys Asp Asp Gly Asn Tyr Lys
                245                 250                 255

Thr Arg Ala Glu Val Lys Phe Glu Gly Asp Thr Leu Val Asn Arg Ile
            260                 265                 270

Glu Leu Lys Gly Ile Asp Phe Lys Glu Asp Gly Asn Ile Leu Gly His
        275                 280                 285

Lys Leu Glu Tyr Asn Tyr Asn Ser His Asn Val Tyr Ile Met Ala Asp
290                 295                 300

Lys Gln Lys Asn Gly Ile Lys Val Asn Phe Lys Ile Arg His Asn Ile
305                 310                 315                 320

Glu Asp Gly Ser Val Gln Leu Ala Asp His Tyr Gln Gln Asn Thr Pro
                325                 330                 335

Ile Gly Asp Gly Pro Val Leu Leu Pro Asp Asn His Tyr Leu Ser Thr
            340                 345                 350

Gln Ser Ala Leu Ser Lys Asp Pro Asn Glu Lys Arg Asp His Met Val
        355                 360                 365

Leu Leu Glu Phe Val Thr Ala Ala Gly Ile Thr Leu Gly Met Asp Glu
370                 375                 380

Leu Tyr Lys Leu Ile Asn
385                 390

<210> SEQ ID NO 94
<211> LENGTH: 1170
<212> TYPE: DNA
<213> ORGANISM: Artificial Sequence
<220> FEATURE:
<223> OTHER INFORMATION: Fusion protein

<400> SEQUENCE: 94
atgggccatc atcatcatca tcatatgtca cacactacac catggacaaa cccaggactc        60
gcagaaaact tcatgaacag tttcatgcaa ggcctgagct cgatgccagg tttcacggca       120
```

| | |
|---|---|
| agccaattgg atgatatgtc aaccatcgca caatccatgg tacagtcaat acaatccttg | 180 |
| gcggcacaag gcaggacatc accgaataag ctgcaggccc ttaacatggc ttttgcatct | 240 |
| tcgatggcag aaatcgcggc atccgaagaa ggagggggaa gcctttccac caaaactagc | 300 |
| tctatagcca gtgcaatgtc caacgcgttt ctgcaaacaa ctggagtggt aaaccaaccg | 360 |
| ttcataaatg aaataactca gctcgttagc atgtttgctc aagcaggtat gaatgatgtc | 420 |
| agtgctggga attccctggt gccacgcggt tctaagggcg aggagctgtt caccggggtg | 480 |
| gtgcccatcc tggtcgagct ggacggcgac gtaaacggcc acaagttcag cgtgtccggc | 540 |
| gagggcgagg gcgatgccac ctacggcaag ctgaccctga agttcatctg caccaccggc | 600 |
| aagctgcccg tgcctggcc caccctcgtg accaccctga cctacggcgt gcagtgcttc | 660 |
| agccgctacc ccgaccacat gaagcagcac gacttcttca gtccgccat gcccgaaggc | 720 |
| tacgtccagg agcgcaccat cttcttcaag gacgacggca actacaagac ccgcgccgag | 780 |
| gtgaagttcg agggcgacac cctggtgaac cgcatcgagc tgaagggcat cgacttcaag | 840 |
| gaggacggca acatcctggg gcacaagctg gagtacaact acaacagcca caacgtctat | 900 |
| atcatggccg acaagcagaa gaacggcatc aaggtgaact tcaagatccg ccacaacatc | 960 |
| gaggacggca gcgtgcagct cgccgaccac taccagcaga caccccccat cggcgacggc | 1020 |
| cccgtgctgc tgcccgacaa ccactacctg agcacccagt ccgccctgag caaagacccc | 1080 |
| aacgagaagc gcgatcacat ggtcctgctg gagttcgtga ccgccgccgg gatcactctc | 1140 |
| ggcatggacg agctgtacaa gttaattaac | 1170 |

<210> SEQ ID NO 95
<211> LENGTH: 1170
<212> TYPE: DNA
<213> ORGANISM: Artificial Sequence
<220> FEATURE:
<223> OTHER INFORMATION: Fusion protein

<400> SEQUENCE: 95

| | |
|---|---|
| atgggccatc atcatcatca tcatatgtca cacactacac catggacaaa cccaggactc | 60 |
| gcagaaaact tcatgaacag tttcatgcaa ggcctgagct cgatgccagg tttcacggca | 120 |
| agccaattgg ataagatgtc aaccatcgca caatccatgg tacagtcaat acaatccttg | 180 |
| gcggcacaag gcaggacatc accgaatgac ctgcaggccc ttaacatggc ttttgcatct | 240 |
| tcgatggcag aaatcgcggc atccgaagaa ggagggggaa gcctttccac caaaactagc | 300 |
| tctatagcca gtgcaatgtc caacgcgttt ctgcaaacaa ctggagtggt aaaccaaccg | 360 |
| ttcataaatg aaataactca gctcgttagc atgtttgctc aagcaggtat gaatgatgtc | 420 |
| agtgctggga attccctggt gccacgcggt tctaagggcg aggagctgtt caccggggtg | 480 |
| gtgcccatcc tggtcgagct ggacggcgac gtaaacggcc acaagttcag cgtgtccggc | 540 |
| gagggcgagg gcgatgccac ctacggcaag ctgaccctga agttcatctg caccaccggc | 600 |
| aagctgcccg tgcctggcc caccctcgtg accaccctga cctacggcgt gcagtgcttc | 660 |
| agccgctacc ccgaccacat gaagcagcac gacttcttca gtccgccat gcccgaaggc | 720 |
| tacgtccagg agcgcaccat cttcttcaag gacgacggca actacaagac ccgcgccgag | 780 |
| gtgaagttcg agggcgacac cctggtgaac cgcatcgagc tgaagggcat cgacttcaag | 840 |
| gaggacggca acatcctggg gcacaagctg gagtacaact acaacagcca caacgtctat | 900 |
| atcatggccg acaagcagaa gaacggcatc aaggtgaact tcaagatccg ccacaacatc | 960 |
| gaggacggca gcgtgcagct cgccgaccac taccagcaga caccccccat cggcgacggc | 1020 |

```
cccgtgctgc tgcccgacaa ccactacctg agcacccagt ccgccctgag caaagacccc      1080
aacgagaagc gcgatcacat ggtcctgctg gagttcgtga ccgccgccgg gatcactctc      1140
ggcatggacg agctgtacaa gttaattaac                                       1170
```

<210> SEQ ID NO 96
<211> LENGTH: 133
<212> TYPE: PRT
<213> ORGANISM: Araneus ventricosus

<400> SEQUENCE: 96

| Gly | Ser | Gly | Asn | Ser | Gln | Pro | Ile | Trp | Thr | Asn | Pro | Asn | Ala | Ala | Met |
| 1   |     |     |     | 5   |     |     |     |     | 10  |     |     |     |     | 15  |     |

| Thr | Met | Thr | Asn | Asn | Leu | Val | Gln | Cys | Ala | Ser | Arg | Ser | Gly | Val | Leu |
|     |     |     | 20  |     |     |     |     | 25  |     |     |     |     | 30  |     |     |

| Thr | Ala | Asp | Gln | Met | Asp | Asp | Met | Gly | Met | Met | Ala | Asp | Ser | Val | Asn |
|     |     | 35  |     |     |     |     | 40  |     |     |     |     | 45  |     |     |     |

| Ser | Gln | Met | Gln | Lys | Met | Gly | Pro | Asn | Pro | Pro | Gln | His | Arg | Leu | Arg |
|     | 50  |     |     |     |     | 55  |     |     |     |     | 60  |     |     |     |     |

| Ala | Met | Asn | Thr | Ala | Met | Ala | Ala | Glu | Val | Ala | Glu | Val | Val | Ala | Thr |
| 65  |     |     |     |     | 70  |     |     |     |     | 75  |     |     |     |     | 80  |

| Ser | Pro | Pro | Gln | Ser | Tyr | Ser | Ala | Val | Leu | Asn | Thr | Ile | Gly | Ala | Cys |
|     |     |     |     | 85  |     |     |     |     | 90  |     |     |     |     | 95  |     |

| Leu | Arg | Glu | Ser | Met | Met | Gln | Ala | Thr | Gly | Ser | Val | Asp | Asn | Ala | Phe |
|     |     |     | 100 |     |     |     |     | 105 |     |     |     |     | 110 |     |     |

| Thr | Asn | Glu | Val | Met | Gln | Leu | Val | Lys | Met | Leu | Ser | Ala | Asp | Ser | Ala |
|     |     | 115 |     |     |     |     | 120 |     |     |     |     | 125 |     |     |     |

| Asn | Glu | Val | Ser | Thr |
|     |     | 130 |     |     |

<210> SEQ ID NO 97
<211> LENGTH: 129
<212> TYPE: PRT
<213> ORGANISM: Latrodectus hesperus

<400> SEQUENCE: 97

| Asp | Ala | Ala | Ser | Val | Trp | Asp | Ser | Thr | Ala | Thr | Ala | Glu | Ala | Phe | Ile |
| 1   |     |     |     | 5   |     |     |     |     | 10  |     |     |     |     | 15  |     |

| Gly | Ser | Phe | Asn | Ser | Gly | Met | Glu | Arg | Ser | Gly | Val | Leu | Ser | Arg | Ser |
|     |     |     | 20  |     |     |     |     | 25  |     |     |     |     | 30  |     |     |

| Gln | Met | Asp | Asp | Ile | Ser | Ser | Ile | Ser | Asp | Thr | Ile | Ile | Ser | Ala | Ile |
|     |     |     | 35  |     |     |     |     | 40  |     |     |     |     | 45  |     |     |

| Glu | Arg | Asn | Pro | Asn | Asn | Ser | Lys | Ser | Lys | Leu | Gln | Ala | Leu | Asn | Met |
|     | 50  |     |     |     |     | 55  |     |     |     |     | 60  |     |     |     |     |

| Ala | Phe | Ala | Ser | Ser | Val | Ser | Glu | Ile | Ala | Phe | Ser | Glu | Asn | Asn | Gly |
| 65  |     |     |     |     | 70  |     |     |     |     | 75  |     |     |     |     | 80  |

| Ile | Ser | Asn | Ser | Ala | Lys | Ile | Gln | Ala | Ile | Ile | Asp | Ala | Leu | Arg | Gly |
|     |     |     |     | 85  |     |     |     |     | 90  |     |     |     |     | 95  |     |

| Ala | Phe | Leu | Gln | Thr | Ile | Gly | Thr | Val | Asp | Gln | Thr | Phe | Leu | Asn | Glu |
|     |     |     | 100 |     |     |     |     | 105 |     |     |     |     | 110 |     |     |

| Ile | Ser | Ser | Leu | Val | Lys | Met | Phe | Ser | Gln | Val | Ser | Ala | Glu | Asn | Ala |
|     |     | 115 |     |     |     |     | 120 |     |     |     |     | 125 |     |     |     |

| Val |

<210> SEQ ID NO 98
<211> LENGTH: 128

```
<212> TYPE: PRT
<213> ORGANISM: Uloborus diversus

<400> SEQUENCE: 98

Gln Gly Ala Ser Val Trp Ser Ser Pro Gln Met Ala Glu Asn Phe Met
1               5                   10                  15

Asn Gly Phe Ser Met Ala Leu Ser Gln Ala Gly Ala Phe Ser Gly Gln
            20                  25                  30

Glu Met Lys Asp Phe Asp Asp Val Arg Asp Ile Met Asn Ser Ala Met
        35                  40                  45

Asp Lys Met Ile Arg Ser Gly Lys Ser Gly Arg Gly Ala Met Arg Ala
    50                  55                  60

Met Asn Ala Ala Phe Gly Ser Ala Ile Ala Glu Ile Val Ala Ala Asn
65                  70                  75                  80

Gly Gly Lys Glu Tyr Gln Ile Gly Ala Val Leu Asp Ala Val Thr Asn
                85                  90                  95

Thr Leu Leu Gln Leu Thr Gly Asn Ala Asp Asn Gly Phe Leu Asn Glu
            100                 105                 110

Ile Ser Arg Leu Ile Thr Leu Phe Ser Ser Val Glu Ala Asn Asp Val
            115                 120                 125

<210> SEQ ID NO 99
<211> LENGTH: 128
<212> TYPE: PRT
<213> ORGANISM: Metepeira grandiosa

<400> SEQUENCE: 99

Ala His Gly His Ile Trp Gly Thr Pro Gly Ala Gly Lys Ser Val Thr
1               5                   10                  15

Gly Ser Ile Val Gln Cys Ala Gly Gln Ser Gly Val Phe Ser Gly Asp
            20                  25                  30

Gln Met Gln Asp Leu Gly Asp Met Ala Asp Ala Val Asn Arg Gln Leu
        35                  40                  45

Asp Arg Leu Gly Pro Asn Ala Pro Asp His Arg Leu Lys Gly Val Thr
    50                  55                  60

Thr Met Met Ala Ala Gly Ile Ala Asp Ala Ala Val Asn Ser Pro Gly
65                  70                  75                  80

Gln Ser Leu Asp Val Met Ile Asn Thr Ile Ser Gly Cys Met Thr Gln
                85                  90                  95

Ala Met Ser Gln Ala Val Gly Tyr Val Asp Gln Thr Leu Ile Arg Glu
            100                 105                 110

Val Ala Glu Met Val Asn Met Leu Ala Asn Glu Asn Ala Asn Ala Val
            115                 120                 125

<210> SEQ ID NO 100
<211> LENGTH: 176
<212> TYPE: PRT
<213> ORGANISM: Artificial Sequence
<220> FEATURE:
<223> OTHER INFORMATION: Fusion protein

<400> SEQUENCE: 100

Met Gly His His His His His His Met Ser His Thr Thr Pro Trp Thr
1               5                   10                  15

Asn Pro Gly Leu Ala Glu Asn Phe Met Asn Ser Phe Met Gln Gly Leu
            20                  25                  30

Ser Ser Met Pro Gly Phe Thr Ala Ser Gln Leu Asp Asp Met Ser Thr
        35                  40                  45
```

```
Ile Ala Gln Ser Met Val Gln Ser Ile Gln Ser Leu Ala Ala Gln Gly
        50                  55                  60

Arg Thr Ser Pro Asn Lys Leu Gln Ala Leu Asn Met Arg Phe Ala Ser
 65                  70                  75                  80

Ser Met Ala Glu Ile Ala Ala Ser Glu Glu Gly Gly Gly Ser Leu Ser
                85                  90                  95

Thr Lys Thr Ser Ser Ile Ala Ser Ala Met Ser Asn Ala Phe Leu Gln
            100                 105                 110

Thr Thr Gly Val Val Asn Gln Pro Phe Ile Asn Glu Ile Thr Gln Leu
            115                 120                 125

Val Ser Met Phe Ala Gln Ala Gly Met Asn Asp Val Ser Ala Met Ile
        130                 135                 140

Pro Ser Ser Pro Val His Leu Lys Arg Leu Lys Leu Leu Leu Leu Leu
145                 150                 155                 160

Leu Leu Leu Ile Leu Leu Leu Ile Leu Gly Ala Leu Leu Leu Gly Leu
                165                 170                 175

<210> SEQ ID NO 101
<211> LENGTH: 426
<212> TYPE: PRT
<213> ORGANISM: Artificial Sequence
<220> FEATURE:
<223> OTHER INFORMATION: Fusion protein

<400> SEQUENCE: 101

Met Gly Ser Ser Gly His His His His His Met Gly Gly Gly Gly
 1               5                  10                  15

Ser Ser His Thr Thr Pro Trp Thr Asn Pro Gly Leu Ala Glu Asn Phe
                20                  25                  30

Met Asn Ser Phe Met Gln Gly Leu Ser Ser Met Pro Gly Phe Thr Ala
            35                  40                  45

Ser Gln Leu Asp Lys Met Ser Thr Ile Ala Gln Ser Met Val Gln Ser
        50                  55                  60

Ile Gln Ser Leu Ala Ala Gln Gly Arg Thr Ser Pro Asn Asp Leu Gln
 65                  70                  75                  80

Ala Leu Asn Met Ala Phe Ala Ser Ser Met Ala Glu Ile Ala Ala Ser
                85                  90                  95

Glu Glu Gly Gly Gly Ser Leu Ser Thr Lys Thr Ser Ser Ile Ala Ser
            100                 105                 110

Ala Met Ser Asn Ala Phe Leu Gln Thr Thr Gly Val Val Asn Gln Pro
            115                 120                 125

Phe Ile Asn Glu Ile Thr Gln Leu Val Ser Met Phe Ala Gln Ala Gly
        130                 135                 140

Met Asn Asp Val Leu Glu Ala Leu Phe Gln Gly Pro Asn Ser Cys Thr
145                 150                 155                 160

Gly Arg Gly Asp Ser Pro Ala Cys Gly Ser Ala Ser Gly Gln Gly Gly
                165                 170                 175

Tyr Gly Gly Leu Gly Gln Gly Gly Tyr Gly Gln Gly Ala Gly Ser Ser
            180                 185                 190

Ala Ala Ala Ala Ala Ala Ala Ala Ala Ala Ala Gly Gly Gln Gly
            195                 200                 205

Gly Gln Gly Gln Gly Gly Tyr Gly Gln Gly Ser Gly Gly Ser Ala Ala
        210                 215                 220

Ala Ala Ala Ala Ala Ala Ala Ala Ala Ala Ala Ala Gly Arg Gly
225                 230                 235                 240
```

```
Gln Gly Gly Tyr Gly Gln Gly Ser Gly Gly Asn Ala Ala Ala Ala
                245                 250                 255

Ala Ala Ala Ala Ala Ala Ala Ala Ala Gly Gln Gly Gly Gln Gly
            260                 265                 270

Gly Tyr Gly Arg Gln Ser Gln Gly Ala Gly Ser Ala Ala Ala Ala
        275                 280                 285

Ala Ala Ala Ala Ala Ala Ala Gly Ser Gly Gln Gly Gly Tyr
        290                 295                 300

Gly Gly Gln Gly Gln Gly Gly Tyr Gly Gln Ser Ser Ala Ser Ala Ser
305                 310                 315                 320

Ala Ala Ala Ser Ala Ala Gly Ser Tyr Ala Gly Ala Val Asn Arg Leu
            325                 330                 335

Ser Ser Ala Glu Ala Ala Ser Arg Val Ser Ser Asn Ile Ala Ala Ile
            340                 345                 350

Ala Ser Gly Gly Ala Ser Ala Leu Pro Ser Val Ile Ser Asn Ile Tyr
            355                 360                 365

Ser Gly Val Val Ala Ser Gly Val Ser Ser Asn Glu Ala Leu Ile Gln
        370                 375                 380

Ala Leu Leu Glu Leu Leu Ser Ala Leu Val His Val Leu Ser Ser Ala
385                 390                 395                 400

Ser Ile Gly Asn Val Ser Ser Val Gly Val Asp Ser Thr Leu Asn Val
            405                 410                 415

Val Gln Asp Ser Val Gly Gln Tyr Val Gly
            420                 425

<210> SEQ ID NO 102
<211> LENGTH: 353
<212> TYPE: PRT
<213> ORGANISM: Artificial Sequence
<220> FEATURE:
<223> OTHER INFORMATION: Fusion protein

<400> SEQUENCE: 102

Met Gly Ser Ser Gly His His His His His Met Gly Gly Gly Gly
1               5                   10                  15

Ser Val Asp Asn Lys Phe Asn Lys Glu Gln Gln Asn Ala Phe Tyr Glu
            20                  25                  30

Ile Leu His Leu Pro Asn Leu Asn Glu Glu Gln Arg Asn Ala Phe Ile
        35                  40                  45

Gln Ser Leu Lys Asp Asp Pro Ser Gln Ser Ala Asn Leu Leu Ala Glu
    50                  55                  60

Ala Lys Lys Leu Asn Asp Ala Gln Ala Pro Lys Leu Glu Ala Leu Phe
65                  70                  75                  80

Gln Gly Pro Asn Ser Cys Thr Gly Arg Gly Asp Ser Pro Ala Cys Gly
                85                  90                  95

Ser Ala Ser Gly Gln Gly Gly Tyr Gly Gly Leu Gly Gln Gly Gly Tyr
            100                 105                 110

Gly Gln Gly Ala Gly Ser Ser Ala Ala Ala Ala Ala Ala Ala Ala
        115                 120                 125

Ala Ala Ala Gly Gly Gln Gly Gly Gln Gly Gly Tyr Gly Gln
        130                 135                 140

Gly Ser Gly Gly Ser Ala Ala Ala Ala Ala Ala Ala Ala Ala
145                 150                 155                 160

Ala Ala Ala Ala Gly Arg Gly Gln Gly Gly Tyr Gly Gln Gly Ser Gly
            165                 170                 175
```

```
Gly Asn Ala Ala Ala Ala Ala Ala Ala Ala Ala Ala
            180                 185                 190

Ala Gly Gln Gly Gly Gln Gly Tyr Gly Arg Gln Ser Gln Gly Ala
        195                 200                 205

Gly Ser Ala Ala Ala Ala Ala Ala Ala Ala Ala Ala
    210                 215                 220

Gly Ser Gly Gln Gly Gly Tyr Gly Gly Gln Gly Gln Gly Gly Tyr Gly
225                 230                 235                 240

Gln Ser Ser Ala Ser Ala Ser Ala Ala Ser Ala Ala Gly Ser Tyr
                245                 250                 255

Ala Gly Ala Val Asn Arg Leu Ser Ser Ala Glu Ala Ala Ser Arg Val
            260                 265                 270

Ser Ser Asn Ile Ala Ala Ile Ala Ser Gly Gly Ala Ser Ala Leu Pro
            275                 280                 285

Ser Val Ile Ser Asn Ile Tyr Ser Gly Val Val Ala Ser Gly Val Ser
            290                 295                 300

Ser Asn Glu Ala Leu Ile Gln Ala Leu Leu Glu Leu Leu Ser Ala Leu
305                 310                 315                 320

Val His Val Leu Ser Ser Ala Ser Ile Gly Asn Val Ser Ser Val Gly
                325                 330                 335

Val Asp Ser Thr Leu Asn Val Val Gln Asp Ser Val Gly Gln Tyr Val
                340                 345                 350

Gly

<210> SEQ ID NO 103
<211> LENGTH: 431
<212> TYPE: PRT
<213> ORGANISM: Artificial Sequence
<220> FEATURE:
<223> OTHER INFORMATION: Fusion protein

<400> SEQUENCE: 103

Met Gly Ser Ser Gly His His His His His Met Gly Gly Gly
1               5                   10                  15

Ser Ser His Thr Thr Pro Trp Thr Asn Pro Gly Leu Ala Glu Asn Phe
                20                  25                  30

Met Asn Ser Phe Met Gln Gly Leu Ser Ser Met Pro Gly Phe Thr Ala
            35                  40                  45

Ser Gln Leu Asp Lys Met Ser Thr Ile Ala Gln Ser Met Val Gln Ser
        50                  55                  60

Ile Gln Ser Leu Ala Ala Gln Gly Arg Thr Ser Pro Asn Asp Leu Gln
65                  70                  75                  80

Ala Leu Asn Met Ala Phe Ala Ser Ser Met Ala Glu Ile Ala Ala Ser
                85                  90                  95

Glu Glu Gly Gly Gly Ser Leu Ser Thr Lys Thr Ser Ser Ile Ala Ser
            100                 105                 110

Ala Met Ser Asn Ala Phe Leu Gln Thr Thr Gly Val Val Asn Gln Pro
        115                 120                 125

Phe Ile Asn Glu Ile Thr Gln Leu Val Ser Met Phe Ala Gln Ala Gly
    130                 135                 140

Met Asn Asp Val Leu Glu Ala Leu Phe Gln Gly Pro Asn Ser Cys Thr
145                 150                 155                 160

Gly Arg Gly Asp Ser Pro Ala Cys Gly Ser Ala Ser Gly Gln Gly Gly
                165                 170                 175
```

Tyr Gly Gly Leu Gly Gln Gly Gly Tyr Gly Gln Gly Ala Gly Ser Ser
            180                 185                 190

Ala Ala Ala Ala Ala Ala Ala Ala Ala Ala Gly Gly Gln Gly
        195                 200                 205

Gly Gln Gly Gln Gly Gly Tyr Gly Gln Gly Ser Gly Gly Ser Ala Ala
    210                 215                 220

Ala Ala Ala Ala Ala Ala Ala Ala Ala Ala Ala Ala Gly Arg Gly
225                 230                 235                 240

Gln Gly Gly Tyr Gly Gln Gly Ser Gly Gly Asn Ala Ala Ala Ala
                245                 250                 255

Ala Ala Ala Ala Ala Ala Ala Ala Ala Ala Gly Gln Gly Gly Gln Gly
        260                 265                 270

Gly Tyr Gly Arg Gln Ser Gln Gly Ala Gly Ser Ala Ala Ala Ala
                275                 280                 285

Ala Ala Ala Ala Ala Ala Ala Ala Gly Ser Gly Gln Gly Gly Tyr
        290                 295                 300

Gly Gly Gln Gly Gln Gly Gly Tyr Gly Gln Ser Ser Ala Ser Ala Ser
305                 310                 315                 320

Ala Ala Ala Ser Ala Ala Ser Thr Val Ala Asn Ser Val Ser Arg Leu
                325                 330                 335

Ser Ser Pro Ser Ala Val Ser Arg Val Ser Ser Ala Val Ser Ser Leu
            340                 345                 350

Val Ser Asn Gly Gln Val Asn Met Ala Ala Leu Pro Asn Ile Ile Ser
            355                 360                 365

Asn Ile Ser Ser Val Ser Ala Ser Pro Gly Ala Ser Gly Cys
            370                 375                 380

Glu Val Ile Val Gln Ala Leu Leu Glu Val Ile Thr Ala Leu Val Gln
385                 390                 395                 400

Ile Val Ser Ser Ser Val Gly Tyr Ile Asn Pro Ser Ala Val Asn
                405                 410                 415

Gln Ile Thr Asn Val Val Ala Asn Ala Met Ala Gln Val Met Gly
            420                 425                 430

<210> SEQ ID NO 104
<211> LENGTH: 358
<212> TYPE: PRT
<213> ORGANISM: Artificial Sequence
<220> FEATURE:
<223> OTHER INFORMATION: Fusion protein

<400> SEQUENCE: 104

Met Gly Ser Ser Gly His His His His His Met Gly Gly Gly Gly
1               5                   10                  15

Ser Val Asp Asn Lys Phe Asn Lys Glu Gln Gln Asn Ala Phe Tyr Glu
                20                  25                  30

Ile Leu His Leu Pro Asn Leu Asn Glu Glu Gln Arg Asn Ala Phe Ile
            35                  40                  45

Gln Ser Leu Lys Asp Asp Pro Ser Gln Ser Ala Asn Leu Leu Ala Glu
        50                  55                  60

Ala Lys Lys Leu Asn Asp Ala Gln Ala Pro Lys Leu Glu Ala Leu Phe
65                  70                  75                  80

Gln Gly Pro Asn Ser Cys Thr Gly Arg Gly Asp Ser Pro Ala Cys Gly
                85                  90                  95

Ser Ala Ser Gly Gln Gly Gly Tyr Gly Gly Leu Gly Gln Gly Gly Tyr
            100                 105                 110

Gly Gln Gly Ala Gly Ser Ser Ala Ala Ala Ala Ala Ala Ala Ala
            115                 120                 125

Ala Ala Ala Gly Gly Gln Gly Gly Gln Gly Gly Tyr Gly Gln
        130                 135                 140

Gly Ser Gly Gly Ser Ala Ala Ala Ala Ala Ala Ala Ala Ala
145                 150                 155                 160

Ala Ala Ala Ala Gly Arg Gly Gln Gly Gly Tyr Gly Gln Ser Gly
                165                 170                 175

Gly Asn Ala Ala Ala Ala Ala Ala Ala Ala Ala Ala Ala
        180                 185                 190

Ala Gly Gln Gly Gly Gln Gly Gly Tyr Gly Arg Gln Ser Gln Gly Ala
    195                 200                 205

Gly Ser Ala Ala Ala Ala Ala Ala Ala Ala Ala Ala Ala
    210                 215                 220

Gly Ser Gly Gln Gly Gly Tyr Gly Gly Gln Gly Gln Gly Gly Tyr Gly
225                 230                 235                 240

Gln Ser Ser Ala Ser Ala Ser Ala Ala Ser Ala Ala Ser Thr Val
            245                 250                 255

Ala Asn Ser Val Ser Arg Leu Ser Ser Pro Ser Ala Val Ser Arg Val
            260                 265                 270

Ser Ser Ala Val Ser Ser Leu Val Ser Asn Gly Gln Val Asn Met Ala
275                 280                 285

Ala Leu Pro Asn Ile Ile Ser Asn Ile Ser Ser Ser Val Ser Ala Ser
        290                 295                 300

Ala Pro Gly Ala Ser Gly Cys Glu Val Ile Val Gln Ala Leu Leu Glu
305                 310                 315                 320

Val Ile Thr Ala Leu Val Gln Ile Val Ser Ser Ser Val Gly Tyr
                325                 330                 335

Ile Asn Pro Ser Ala Val Asn Gln Ile Thr Asn Val Val Ala Asn Ala
            340                 345                 350

Met Ala Gln Val Met Gly
        355

<210> SEQ ID NO 105
<211> LENGTH: 661
<212> TYPE: PRT
<213> ORGANISM: Artificial Sequence
<220> FEATURE:
<223> OTHER INFORMATION: Fusion protein

<400> SEQUENCE: 105

Met Gly Ser Ser Gly His His His His His Met Gly Gly Gly
1               5                   10                  15

Ser Ser His Thr Thr Pro Trp Thr Asn Pro Gly Leu Ala Glu Asn Phe
            20                  25                  30

Met Asn Ser Phe Met Gln Gly Leu Ser Ser Met Pro Gly Phe Thr Ala
        35                  40                  45

Ser Gln Leu Asp Lys Met Ser Thr Ile Ala Gln Ser Met Val Gln Ser
    50                  55                  60

Ile Gln Ser Leu Ala Ala Gln Gly Arg Thr Ser Pro Asn Asp Leu Gln
65                  70                  75                  80

Ala Leu Asn Met Ala Phe Ala Ser Ser Met Ala Glu Ile Ala Ala Ser
                85                  90                  95

Glu Glu Gly Gly Gly Ser Leu Ser Thr Lys Thr Ser Ser Ile Ala Ser
            100                 105                 110

```
Ala Met Ser Asn Ala Phe Leu Gln Thr Thr Gly Val Val Asn Gln Pro
            115                 120                 125

Phe Ile Asn Glu Ile Thr Gln Leu Val Ser Met Phe Ala Gln Ala Gly
        130                 135                 140

Met Asn Asp Val Leu Glu Ala Leu Phe Gln Gly Pro Asn Ser Glu Val
145                 150                 155                 160

Gln Leu Leu Glu Ser Gly Gly Leu Val Gln Pro Gly Gly Ser Leu
                165                 170                 175

Arg Leu Ser Cys Ala Ala Ser Gly Phe Thr Phe Ser Ser Tyr Ala Met
                180                 185                 190

Ser Trp Val Arg Gln Ala Pro Gly Lys Gly Leu Glu Trp Val Ser Gly
        195                 200                 205

Ile Gly Ser Tyr Gly Gly Gly Thr Tyr Tyr Ala Asp Ser Val Lys Gly
    210                 215                 220

Arg Phe Thr Ile Ser Arg Asp Asn Ser Lys Asn Thr Leu Tyr Leu Gln
225                 230                 235                 240

Met Asn Ser Leu Arg Ala Glu Asp Thr Ala Val Tyr Tyr Cys Ala Arg
                245                 250                 255

Tyr Val Asn Phe Gly Met Asp Tyr Trp Gly Gln Gly Thr Leu Val Thr
            260                 265                 270

Val Ser Ser Gly Gly Gly Gly Ser Gly Gly Gly Ser Gly Gly Gly
            275                 280                 285

Gly Ser Asp Ile Gln Met Thr Gln Ser Pro Ser Ser Leu Ser Ala Ser
    290                 295                 300

Val Gly Asp Arg Val Thr Ile Thr Cys Arg Ala Ser Gln Ser Ile Ser
305                 310                 315                 320

Ser Tyr Leu Asn Trp Tyr Gln Gln Lys Pro Gly Lys Ala Pro Lys Leu
                325                 330                 335

Leu Ile Tyr Ala Ala Ser Ser Leu Gln Ser Gly Val Pro Ser Arg Phe
            340                 345                 350

Ser Gly Ser Gly Ser Gly Thr Asp Phe Thr Leu Thr Ile Ser Ser Leu
            355                 360                 365

Gln Pro Glu Asp Phe Ala Thr Tyr Tyr Cys Gln Gln Tyr Gly Arg Asn
    370                 375                 380

Pro Pro Thr Phe Gly Gln Gly Thr Lys Leu Glu Ile Lys Arg Gly Ser
385                 390                 395                 400

Ala Ser Gly Gln Gly Gly Tyr Gly Gly Leu Gly Gln Gly Gly Tyr Gly
                405                 410                 415

Gln Gly Ala Gly Ser Ser Ala Ala Ala Ala Ala Ala Ala Ala Ala
            420                 425                 430

Ala Ala Gly Gly Gln Gly Gly Gln Gly Gln Gly Gly Tyr Gly Gln Gly
            435                 440                 445

Ser Gly Gly Ser Ala Ala Ala Ala Ala Ala Ala Ala Ala Ala Ala
            450                 455                 460

Ala Ala Ala Gly Arg Gly Gln Gly Gly Tyr Gly Gln Gly Ser Gly Gly
465                 470                 475                 480

Asn Ala Ala Ala Ala Ala Ala Ala Ala Ala Ala Ala Ala Ala Ala
                485                 490                 495

Gly Gln Gly Gly Gln Gly Gly Tyr Gly Arg Gln Ser Gln Gly Ala Gly
            500                 505                 510

Ser Ala Ala Ala Ala Ala Ala Ala Ala Ala Ala Ala Ala Ala Gly
            515                 520                 525
```

Ser Gly Gln Gly Gly Tyr Gly Gly Gln Gly Gly Tyr Gly Gln
    530                 535                 540

Ser Ser Ala Ser Ala Ser Ala Ala Ser Ala Ala Ser Thr Val Ala
545                 550                 555                 560

Asn Ser Val Ser Arg Leu Ser Ser Pro Ser Ala Val Ser Arg Val Ser
                565                 570                 575

Ser Ala Val Ser Ser Leu Val Ser Asn Gly Gln Val Asn Met Ala Ala
                580                 585                 590

Leu Pro Asn Ile Ile Ser Asn Ile Ser Ser Val Ser Ala Ser Ala
                595                 600                 605

Pro Gly Ala Ser Gly Cys Glu Val Ile Val Gln Ala Leu Leu Glu Val
            610                 615                 620

Ile Thr Ala Leu Val Gln Ile Val Ser Ser Ser Val Gly Tyr Ile
625                 630                 635                 640

Asn Pro Ser Ala Val Asn Gln Ile Thr Asn Val Val Ala Asn Ala Met
                645                 650                 655

Ala Gln Val Met Gly
            660

<210> SEQ ID NO 106
<211> LENGTH: 588
<212> TYPE: PRT
<213> ORGANISM: Artificial Sequence
<220> FEATURE:
<223> OTHER INFORMATION: Fusion protein

<400> SEQUENCE: 106

Met Gly Ser Ser Gly His His His His His Met Gly Gly Gly
1               5                   10                  15

Ser Val Asp Asn Lys Phe Asn Lys Glu Gln Gln Asn Ala Phe Tyr Glu
                20                  25                  30

Ile Leu His Leu Pro Asn Leu Asn Glu Glu Gln Arg Asn Ala Phe Ile
            35                  40                  45

Gln Ser Leu Lys Asp Asp Pro Ser Gln Ser Ala Asn Leu Leu Ala Glu
    50                  55                  60

Ala Lys Lys Leu Asn Asp Ala Gln Ala Pro Lys Leu Glu Ala Leu Phe
65                  70                  75                  80

Gln Gly Pro Asn Ser Glu Val Gln Leu Leu Glu Ser Gly Gly Gly Leu
                85                  90                  95

Val Gln Pro Gly Gly Ser Leu Arg Leu Ser Cys Ala Ala Ser Gly Phe
                100                 105                 110

Thr Phe Ser Ser Tyr Ala Met Ser Trp Val Arg Gln Ala Pro Gly Lys
            115                 120                 125

Gly Leu Glu Trp Val Ser Gly Ile Gly Ser Tyr Gly Gly Gly Thr Tyr
    130                 135                 140

Tyr Ala Asp Ser Val Lys Gly Arg Phe Thr Ile Ser Arg Asp Asn Ser
145                 150                 155                 160

Lys Asn Thr Leu Tyr Leu Gln Met Asn Ser Leu Arg Ala Glu Asp Thr
                165                 170                 175

Ala Val Tyr Tyr Cys Ala Arg Tyr Val Asn Phe Gly Met Asp Tyr Trp
            180                 185                 190

Gly Gln Gly Thr Leu Val Thr Val Ser Ser Gly Gly Gly Ser Gly
    195                 200                 205

Gly Gly Gly Ser Gly Gly Gly Gly Ser Asp Ile Gln Met Thr Gln Ser
210                 215                 220

Pro Ser Ser Leu Ser Ala Ser Val Gly Asp Arg Val Thr Ile Thr Cys
225                 230                 235                 240

Arg Ala Ser Gln Ser Ile Ser Ser Tyr Leu Asn Trp Tyr Gln Gln Lys
            245                 250                 255

Pro Gly Lys Ala Pro Lys Leu Leu Ile Tyr Ala Ala Ser Ser Leu Gln
        260                 265                 270

Ser Gly Val Pro Ser Arg Phe Ser Gly Ser Gly Ser Gly Thr Asp Phe
    275                 280                 285

Thr Leu Thr Ile Ser Ser Leu Gln Pro Glu Asp Phe Ala Thr Tyr Tyr
290                 295                 300

Cys Gln Gln Tyr Gly Arg Asn Pro Pro Thr Phe Gly Gln Gly Thr Lys
305                 310                 315                 320

Leu Glu Ile Lys Arg Gly Ser Ala Ser Gly Gln Gly Tyr Gly Gly
            325                 330                 335

Leu Gly Gln Gly Gly Tyr Gly Gln Gly Ala Gly Ser Ser Ala Ala Ala
    340                 345                 350

Ala Ala Ala Ala Ala Ala Ala Ala Gly Gly Gln Gly Gly Gln Gly
            355                 360                 365

Gln Gly Gly Tyr Gly Gln Gly Ser Gly Gly Ser Ala Ala Ala Ala
370                 375                 380

Ala Ala Ala Ala Ala Ala Ala Ala Gly Arg Gly Gln Gly Gly
385                 390                 395                 400

Tyr Gly Gln Gly Ser Gly Gly Asn Ala Ala Ala Ala Ala Ala Ala
            405                 410                 415

Ala Ala Ala Ala Ala Ala Gly Gln Gly Gly Gln Gly Gly Tyr Gly
            420                 425                 430

Arg Gln Ser Gln Gly Ala Gly Ser Ala Ala Ala Ala Ala Ala Ala
            435                 440                 445

Ala Ala Ala Ala Ala Ala Gly Ser Gly Gln Gly Gly Tyr Gly Gly Gln
    450                 455                 460

Gly Gln Gly Gly Tyr Gly Gln Ser Ser Ala Ser Ala Ser Ala Ala
465                 470                 475                 480

Ser Ala Ala Ser Thr Val Ala Asn Ser Val Ser Arg Leu Ser Ser Pro
            485                 490                 495

Ser Ala Val Ser Arg Val Ser Ser Ala Val Ser Ser Leu Val Ser Asn
        500                 505                 510

Gly Gln Val Asn Met Ala Ala Leu Pro Asn Ile Ile Ser Asn Ile Ser
    515                 520                 525

Ser Ser Val Ser Ala Ser Ala Pro Gly Ala Ser Gly Cys Glu Val Ile
530                 535                 540

Val Gln Ala Leu Leu Glu Val Ile Thr Ala Leu Val Gln Ile Val Ser
545                 550                 555                 560

Ser Ser Ser Val Gly Tyr Ile Asn Pro Ser Ala Val Asn Gln Ile Thr
            565                 570                 575

Asn Val Val Ala Asn Ala Met Ala Gln Val Met Gly
            580                 585

<210> SEQ ID NO 107
<211> LENGTH: 414
<212> TYPE: PRT
<213> ORGANISM: Artificial Sequence
<220> FEATURE:
<223> OTHER INFORMATION: Fusion protein

<400> SEQUENCE: 107

```
Met Gly Ser Ser Gly His His His His His His Met Gly Gly Gly
1               5                   10                  15

Ser Ser His Thr Thr Pro Trp Thr Asn Pro Gly Leu Ala Glu Asn Phe
            20                  25                  30

Met Asn Ser Phe Met Gln Gly Leu Ser Ser Met Pro Gly Phe Thr Ala
            35                  40                  45

Ser Gln Leu Asp Lys Met Ser Thr Ile Ala Gln Ser Met Val Gln Ser
            50                  55                  60

Ile Gln Ser Leu Ala Ala Gln Gly Arg Thr Ser Pro Asn Asp Leu Gln
65                  70                  75                  80

Ala Leu Asn Met Ala Phe Ala Ser Ser Met Ala Glu Ile Ala Ala Ser
                85                  90                  95

Glu Glu Gly Gly Gly Ser Leu Ser Thr Lys Thr Ser Ser Ile Ala Ser
            100                 105                 110

Ala Met Ser Asn Ala Phe Leu Gln Thr Thr Gly Val Val Asn Gln Pro
            115                 120                 125

Phe Ile Asn Glu Ile Thr Gln Leu Val Ser Met Phe Ala Gln Ala Gly
            130                 135                 140

Met Asn Asp Val Leu Glu Ala Leu Phe Gln Gly Pro Asn Ser Glu Val
145                 150                 155                 160

Gln Leu Leu Glu Ser Gly Gly Gly Leu Val Gln Pro Gly Gly Ser Leu
                165                 170                 175

Arg Leu Ser Cys Ala Ala Ser Gly Phe Thr Phe Ser Ser Tyr Ala Met
            180                 185                 190

Ser Trp Val Arg Gln Ala Pro Gly Lys Gly Leu Glu Trp Val Ser Gly
            195                 200                 205

Ile Gly Ser Tyr Gly Gly Gly Thr Tyr Tyr Ala Asp Ser Val Lys Gly
            210                 215                 220

Arg Phe Thr Ile Ser Arg Asp Asn Ser Lys Asn Thr Leu Tyr Leu Gln
225                 230                 235                 240

Met Asn Ser Leu Arg Ala Glu Asp Thr Ala Val Tyr Tyr Cys Ala Arg
                245                 250                 255

Tyr Val Asn Phe Gly Met Asp Tyr Trp Gly Gln Gly Thr Leu Val Thr
            260                 265                 270

Val Ser Ser Gly Gly Gly Gly Ser Gly Gly Gly Gly Ser Gly Gly Gly
            275                 280                 285

Gly Ser Asp Ile Gln Met Thr Gln Ser Pro Ser Ser Leu Ser Ala Ser
            290                 295                 300

Val Gly Asp Arg Val Thr Ile Thr Cys Arg Ala Ser Gln Ser Ile Ser
305                 310                 315                 320

Ser Tyr Leu Asn Trp Tyr Gln Gln Lys Pro Gly Lys Ala Pro Lys Leu
                325                 330                 335

Leu Ile Tyr Ala Ala Ser Ser Leu Gln Ser Gly Val Pro Ser Arg Phe
            340                 345                 350

Ser Gly Ser Gly Ser Gly Thr Asp Phe Thr Leu Thr Ile Ser Ser Leu
            355                 360                 365

Gln Pro Glu Asp Phe Ala Thr Tyr Tyr Cys Gln Gln Tyr Gly Arg Asn
            370                 375                 380

Pro Pro Thr Phe Gly Gln Gly Thr Lys Leu Glu Ile Lys Arg Gly Ser
385                 390                 395                 400

Ala Ser Gly Ser Gly Ser Gly Ser Leu Pro Glu Thr Gly Gly
                405                 410
```

<210> SEQ ID NO 108
<211> LENGTH: 341
<212> TYPE: PRT
<213> ORGANISM: Artificial Sequence
<220> FEATURE:
<223> OTHER INFORMATION: Fusion protein

<400> SEQUENCE: 108

```
Met Gly Ser Ser Gly His His His His His Met Gly Gly Gly
1               5                   10                  15

Ser Val Asp Asn Lys Phe Asn Lys Glu Gln Gln Asn Ala Phe Tyr Glu
            20                  25                  30

Ile Leu His Leu Pro Asn Leu Asn Glu Glu Gln Arg Asn Ala Phe Ile
        35                  40                  45

Gln Ser Leu Lys Asp Asp Pro Ser Gln Ser Ala Asn Leu Leu Ala Glu
    50                  55                  60

Ala Lys Lys Leu Asn Asp Ala Gln Ala Pro Lys Leu Glu Ala Leu Phe
65                  70                  75                  80

Gln Gly Pro Asn Ser Glu Val Gln Leu Leu Glu Ser Gly Gly Gly Leu
                85                  90                  95

Val Gln Pro Gly Gly Ser Leu Arg Leu Ser Cys Ala Ala Ser Gly Phe
            100                 105                 110

Thr Phe Ser Ser Tyr Ala Met Ser Trp Val Arg Gln Ala Pro Gly Lys
        115                 120                 125

Gly Leu Glu Trp Val Ser Gly Ile Gly Ser Tyr Gly Gly Thr Tyr
    130                 135                 140

Tyr Ala Asp Ser Val Lys Gly Arg Phe Thr Ile Ser Arg Asp Asn Ser
145                 150                 155                 160

Lys Asn Thr Leu Tyr Leu Gln Met Asn Ser Leu Arg Ala Glu Asp Thr
                165                 170                 175

Ala Val Tyr Tyr Cys Ala Arg Tyr Val Asn Phe Gly Met Asp Tyr Trp
            180                 185                 190

Gly Gln Gly Thr Leu Val Thr Val Ser Ser Gly Gly Gly Gly Ser Gly
        195                 200                 205

Gly Gly Gly Ser Gly Gly Gly Ser Asp Ile Gln Met Thr Gln Ser
    210                 215                 220

Pro Ser Ser Leu Ser Ala Ser Val Gly Asp Arg Val Thr Ile Thr Cys
225                 230                 235                 240

Arg Ala Ser Gln Ser Ile Ser Ser Tyr Leu Asn Trp Tyr Gln Gln Lys
                245                 250                 255

Pro Gly Lys Ala Pro Lys Leu Leu Ile Tyr Ala Ala Ser Ser Leu Gln
            260                 265                 270

Ser Gly Val Pro Ser Arg Phe Ser Gly Ser Gly Ser Gly Thr Asp Phe
        275                 280                 285

Thr Leu Thr Ile Ser Ser Leu Gln Pro Glu Asp Phe Ala Thr Tyr Tyr
    290                 295                 300

Cys Gln Gln Tyr Gly Arg Asn Pro Pro Thr Phe Gly Gln Gly Thr Lys
305                 310                 315                 320

Leu Glu Ile Lys Arg Gly Ser Ala Ser Gly Ser Gly Ser Leu
                325                 330                 335

Pro Glu Thr Gly Gly
            340
```

CHARGE-REVERSED N-TERMINAL SPIDER SILK PROTEIN DOMAIN AND USES THEREOF

TECHNICAL FIELD OF THE INVENTION

The present invention relates to the field of proteins and polypeptides, and more specifically to expression and production of spider silk proteins (spidroins) and other, non-spidroin proteins and polypeptides. The present invention provides novel proteins which are useful in themselves and as a moiety in novel fusion proteins for expression and production of the desired proteins and polypeptides, as well as nucleic acid molecules encoding these novel proteins and fusion proteins. The present invention also provides a method of expressing and producing a desired protein or polypeptide.

BACKGROUND TO THE INVENTION

Production of proteins and polypeptides from DNA can be achieved in various hosts, but a common problem is the formation of insoluble protein/polypeptide aggregates. This may severely impede or even prevent production of a functional protein/polypeptide. The problem is typically aggravated with low-solubility proteins and polypeptides, e.g. membrane-associated proteins and polypeptides.

Membrane-associated proteins account for 20-30% of the proteome of the cell and are the targets of many currently available pharmaceutical drugs. In order to get inserted into the membrane, the protein needs at least one stretch of 15-20 amino acid residues that, according to the biological hydrophobicity scale, promotes membrane insertion. At the same time, hydrophobicity of the amino acid side chains is an important determinant of aggregation potential, and hydrophobic amino acid residues (Val, Ile, Phe and Cys) promote β-sheet formation and are overrepresented in amyloid forming core regions of many disease associated proteins. Accordingly, membrane associated proteins are prone to aggregate, which may severely impede or even prevent the production of a functional recombinant protein.

For instance, lung surfactant protein C (SP-C) is a transmembrane (TM) protein that is difficult to produce recombinantly because of its extremely hydrophobic nature. SP-C is produced by alveolar type II cells and is a constituent of surfactant, that is necessary to prevent alveolar collapse at end expiration. Neonatals often suffer from respiratory distress due to insufficient amounts of surfactant. Today, this condition is treated with surfactant preparations extracted from animal lungs, e.g. Curosurf®, Infasurf®, Alveofact® and Survanta®. Treatment with exogenous surfactant is also potentially beneficial for adult patients with respiratory distress, but the supply of surfactant is too limited and the price very high. Surfactant preparations based on peptides produced in a heterologous system would be superior to the natural extracts used today (and formulations containing chemically synthesized peptides) due to lower production cost and higher production volume. It would also be favourable from a regulatory point of view.

SP-C33Leu is a variant of SP-C, where the N-terminal part is truncated with two residues, two Cys residues are replaced with Ser, one Leu residue is replaced with Lys, and one Met residue is replaced with Leu, and the residues spanning the membrane (normally mainly Val) are exchanged for Leu in order to enhance the stability of the transmembrane helix. KL4 is another surfactant analogue designed to imitate the properties of the lung surfactant protein B (SP-B) and consists of iterated repeats of Lys-Leu-Leu-Leu-Leu. SP-C33Leu and KL4 recapitulate the function of native surfactant peptides, including transmembraneous insertion, but are less prone to aggregate and may therefore be feasible to produce in large quantities for development of a synthetic surfactant preparation. Both peptides can be produced by chemical synthesis but the cost is considerable and the process renders bi-products that may be difficult to remove and to characterize.

The pulmonary surfactant proteins A (SP-A) and D (SP-D) do not insert into membranes but rather play a role in the pulmonary immune response through their carbohydrate-binding domains. They are large water-soluble protein complexes involved in the first line defence of the lungs and regulate the functions of the innate immune cells (e.g. macrophages) as well as the adaptive immune cells. The proteins belong to the collectin family of C-type lectins composed of an N-terminal collagen-like region and a C-terminal calcium-dependent carbohydrate recognition domain. In their functional form, the proteins are arranged as trimeric polypeptide chains via their N-terminal regions and further assemble into larger oligomers of different shapes. SP-A consists of six trimeric subunits arranged as a "bouquet", while SP-D arrange as a cruciform of four trimeric subunits. Although the proteins are hydrophilic, they are reluctant to recombinant production and have so far been expressed as insoluble inclusion bodies and purified by denaturation and refolding. Currently, surfactant preparations in clinical use do not contain SP-A or SP-D and there is an interest to investigate if current surfactant therapies could be improved by adding these components that are a natural part of surfactants. Human SP-A and SP-D can be isolated from patients with alveolar proteinosis or from amniotic fluid but the yields are low and the oligomeric state is non-uniform. Recombinant production of the proteins would allow for scaled-up and reproducible manufacturing for therapeutic use but so far the attempts have been unconvincing.

Other examples of proteins and polypeptides that pose difficulties when expressed from recombinant DNA are Aβ-peptide, IAPP, PrP, α-synuclein, calcitonin, prolactin, cystatin, ATF and actin; SP-B, α-defensins and β-defensins; class A-H apolipoproteins; LL-37, hCAP18, SP-C, SP-C33, Brichos, GFP, eGFP, nicastrin, neuroserpin; hormones, including EPO and GH, and growth factors, including IGF-I and IGF-II; avidin and streptavidin; protease 3C; and immunoglobulins and fragments thereof.

One solution to this problem is to express the desired protein or polypeptide as a fusion protein with a solubility enhancing peptide/domain, i.e. a protein or polypeptide that provides the required solubility. The fusion protein may be cleaved, and the desired protein isolated. Alternatively, the desired protein/polypeptide may be maintained integrated in the soluble fusion protein, where it remains functional and can be subjected to further characterization, e.g. activity and interaction studies, structure determination and crystallization. Thioredoxin (Trx) is among the most widely used solubility enhancing fusion partners that accumulate to high levels in the *E. coli* cytoplasm and has proven to dramatically increase the solubility of many heterologous proteins and small peptides. Another successful fusion partner is the immunoglobulin binding domain B1 from Streptococcal protein G (PGB1). The high stability and small size (56 residues) of this domain gives it exceptional qualities for expression of small domains and peptides and for downstream structural characterization.

WO 2011/115538 discloses a fusion protein comprising a solubility-enhancing moiety which is derived from the N-terminal (NT) fragment of a spider silk protein and a moiety which is a desired protein or polypeptide. A pH above 6.4 is preferred to prevent assembly of the solubility-enhancing moiety.

EP 2 644 619 A1 also discloses a fusion protein comprising a solubility-enhancing moiety which is derived from the N-terminal (NT) fragment of a spider silk protein and a moiety which is a desired protein or polypeptide. The solubility-enhancing moiety is a constitutive monomer also below a pH of 6.4, but does not increase expression levels of the resulting fusion proteins compared to the wildtype NT fragment.

Despite these progresses in the field, the fusion protein approach has limitations in terms of expression, stability and solubility of the product. The use of fusion partners in large-scale heterologous protein production is uncommon, mainly due to the need of additional expensive chromatographic steps and/or difficulties in removing the fusion partner.

SUMMARY OF THE INVENTION

It is an object of the present invention to provide a fusion partner, i.e. a moiety in a fusion protein, which is useful for enhancing the solubility of another moiety in the fusion protein, which is a desired protein or polypeptide.

It is also an object to provide novel proteins and a method for improved recombinant production method for hydrophobic proteins and polypeptides and proteins and polypeptides with hydrophobic regions.

It is a further object of the present invention to provide a fusion partner which is a stable monomer over a broad pH range.

It is another object of the present invention to provide a simplified method of producing and isolating a desired protein or polypeptide involving expression in a fusion protein.

For these and other objects that will be evident from the following specification, the present invention provides according to a first aspect a protein according to the appended claims. The present invention is generally based on the discovery that this charge-reversed NT mutant is unable to dimerize, stabilized, hypersoluble and enables efficient production of transmembrane and aggregation-prone proteins. Fusion proteins according to the invention can advantageously form micelles. The present invention provides according to a second aspect use of this protein as a moiety in a fusion protein for enhancing the solubility of another moiety in the fusion protein, which is a desired protein or polypeptide.

The present invention provides according to a third aspect a method of producing a desired protein or polypeptide according to the appended claims.

LIST OF APPENDED SEQUENCES

SEQ ID NO
1 $NT_{D40K/R/H,K65D/E}$
2 $NT_{D40K,K65D}$
3 $NT_{D40R,K65D}$
4 $NT_{D40H,K65D}$
5 $NT_{D40K,K65E}$
6 $NT_{D40R,K65E}$
7 $NT_{D40H,K65E}$
8 $NT_{D40K,K65D}$ (DNA)
9 NT full-length
10 consensus NT sequence
11 $NT_{wt}$
12 $NT_{wt}$ (DNA)
13 NT *Euprosthenops australis* MaSp1
14 NT *Latrodectus geometricus* MaSp1
15 NT *Latrodectus hesperus* MaSp1
16 NT *Nephila clavipes* MaSp1
17 NT *Argiope trifasciata* MaSp2
18 NT *Latrodectus geometricus* MaSp2
19 NT *Latrodectus hesperus* MaSp2
20 NT *Nephila inaurata madagascariensis* MaSp2
21 NT *Nephila clavipes* MaSp2
22 NT *Argiope bruennichi* cylindriform spidroin 1
23 NT *Nephila clavata* cylindriform spidroin 1
24 NT *Latrodectus hesperus* tubuliform spidroin
25 NT *Nephila clavipes* flagelliform silk protein
26 NT *Nephila inaurata madagascariensis* flagelliform silk protein
27 β17
28 Human SP-B
29 Mouse SP-B
30 Pig SP-B
31 Rabbit SP-B
32 Rat SP-B
33 Mini-B
34 Mini-BLeu
35 Mini-B27
36 1a AA
37 1b AA
38 1a LL
39 1b LL
40 SP-C
41 SP-C(Leu)
42 SP-C33
43 SP-C30
44 SP-C33(Leu)
45 LL-37
46 KL4
47 $hSP-A1_{81-228}$
48 $hSP-A2_{81-228}$
49 $hSP-D_{204-355}$
50 $Bri2_{113-231}$ (Bri2-Brichos)
51 Neuroserpin
52 0 AAAA
53 0 LLLL
54 Green Fluorescent Protein (GFP)
55 eGFP
56 $NT_{D40K,K65D}$-SP-C33Leu
57 $NT_{wt}$-SP-C33Leu
58 $NT_{D40K,K65D}$-SP-C33Leu (DNA)
59 $NT_{wt}$-SP-C33Leu (DNA)
60 $NT_{D40K,K65D}$-KL4
61 $NT_{wt}$-KL4
62 $NT_{D40K,K65D}$-KL4 (DNA)
63 $N_{wt}$-KL4 (DNA)
64 $NT_{D40K,K65D}$-β17
65 $NT_{D40K,K65D}$-β17 (DNA)
66 $NT_{D40K,K65D}$-$Bri2_{113-231}$
67 $NT_{wt}$-$Bri2_{113-231}$
68 $NT_{D40K,K65D}$-$Bri2_{113-231}$ (DNA)
69 $NT_{wt}$-$Bri2_{113-231}$ (DNA)
70 $NT_{D40K,K65D}$-hSP-A1
71 $NT_{D40K,K65D}$-hSP-A2
72 $NT_{D40K,K65D}$-hSP-D
73 $NT_{D40K,K65D}$-$hSP-A1_{81-228}$
74 $NT_{D40K,K65D}$-$hSP-A2_{81-228}$ 75 NT$_{D40K,K65D}$-hSP-D$_{204-355}$
76 NT$_{D40K,K65D}$-hSP-A1 (DNA)
77 NT$_{D40K,K65D}$-hSP-A2 (DNA)
78 NT$_{D40K,K65D}$-hSP-D (DNA)
79 NT$_{D40K,K65D}$-hSP-A1$_{81-228}$ (DNA)
80 NT$_{D40K,K65D}$-hSP-A2$_{81-228}$ (DNA)
81 NT$_{D40K,K65D}$-hSP-D$_{204-355}$ (DNA)
82 NT$_{D40K,K65D}$-Aβ$_{1-42}$
83 NT$_{D40K,K65D}$-Aβ$_{1-42}$ (DNA)
84 NT$_{D40K,K65D}$-hIAPP
85 NT$_{D40K,K65D}$-hIAPP (DNA)
86 NT$_{wt}$-hCAP18
87 NT$_{D40K,K65D}$-hCAP18
88 NT$_{wt}$-hCAP18 (DNA)
89 NT$_{D40K,K65D}$-hCAP18 (DNA)
90 NT$_{D40K,K65D}$-nicastrin
91 NT$_{D40K,K65D}$-nicastrin (DNA)
92 NT$_{wt}$-eGFP
93 NT$_{D40K,K65D}$eGFP
94 NT$_{wt}$-eGFP (DNA)
95 NT$_{D40K,K65D}$-eGFP (DNA)
96 NT *Araneus ventricosus* MiSp
97 NT *Latrodectus hesperus* MiSp
98 NT *Uloborus diversus* MiSp
99 NT *Metepeira grandiosa* MiSp
100 NT$_{A72R}$-SP-C33Leu
101 NT$_{D40K,K65D}$-FN$_{CC}$-4Rep-CT$_{MiSp}$
102 Z-FN$_{CC}$-4Rep-CT$_{MiSp}$
103 NT$_{D40K,K65D}$-FN$_{CC}$-4Rep-CT$_{MaSp}$
104 Z-FN$_{CC}$-4Rep-CT$_{MaSp}$
105 NT$_{D40K,K65D}$-sCD40-4Rep-CT$_{MaSp}$
106 Z-sCD40-4Rep-CT$_{MaSp}$
107 NT$_{D40K,K65D}$-sCD40-sortase
108 Z-sCD40-sortase

BRIEF DESCRIPTION OF THE DRAWINGS

FIG. 1 is a sequence alignment of spidroin N-terminal domains.

FIG. 7-8 are SDS-PAGE evaluations of fusion proteins and resulting purified proteins and peptides.

FIG. 9 shows ESI-MS spectra of SP-C33Leu produced by the inventive method.

FIG. 10 illustrates the effects of rSP-C33Leu on tidal volumes.

FIG. 11 illustrates the effects of rSP-C33Leu on lung gas volumes.

FIG. 12 is an SDS-PAGE evaluation of β17 fusion proteins and resulting purified polypeptide.

FIG. 13 shows gel filtration of soluble NT$_{D40K/K65D}$-β17 fusion protein.

FIG. 15 is an SDS-PAGE evaluation of expression and solubility of Bri2 BRICHOS fusion proteins.

FIG. 16 is an SDS-PAGE analysis of Bri2 BRICHOS purification.

DETAILED DESCRIPTION OF THE INVENTION

Figure 2:
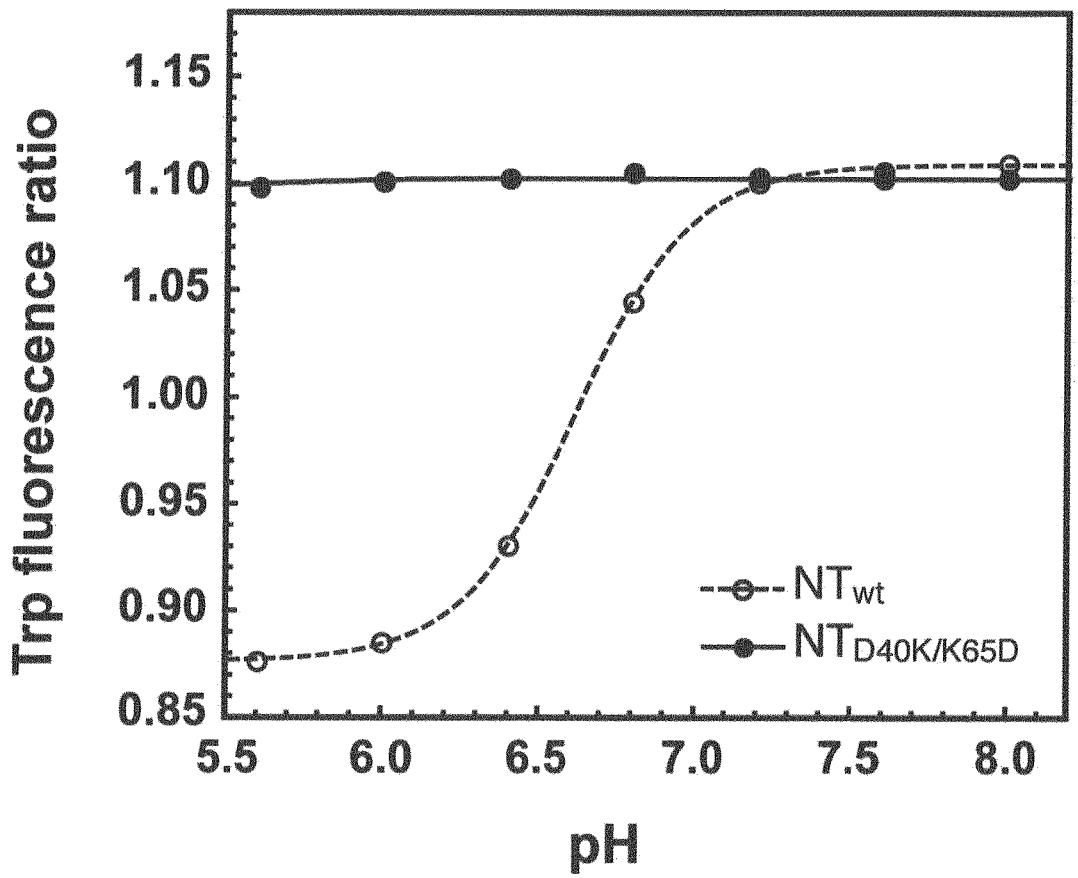
FIG. 2 shows the ratio of fluorescence emission at 339 nm and 351 nm vs pH for NT$_{D40K/K65D}$ and wild type NT.
Figure 3:
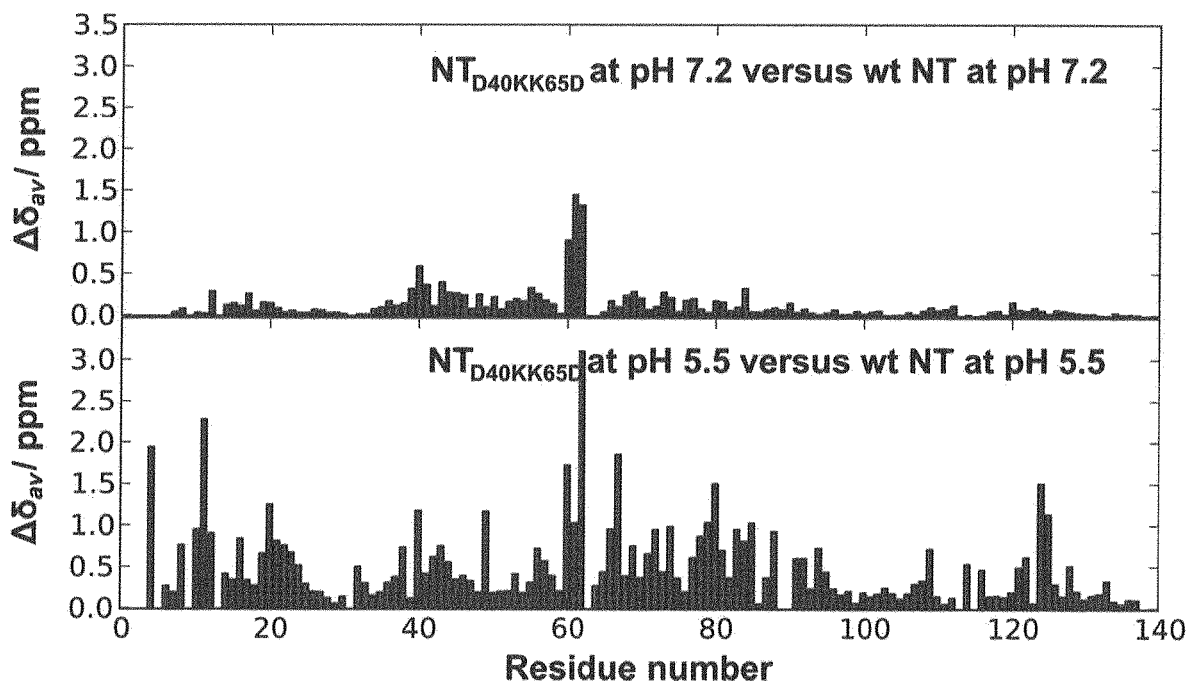
FIG. 3 is a comparison of NT$_{wt}$ and NT$_{D40K/K65D}$ using 2D HSQC NMR.
Figure 4:
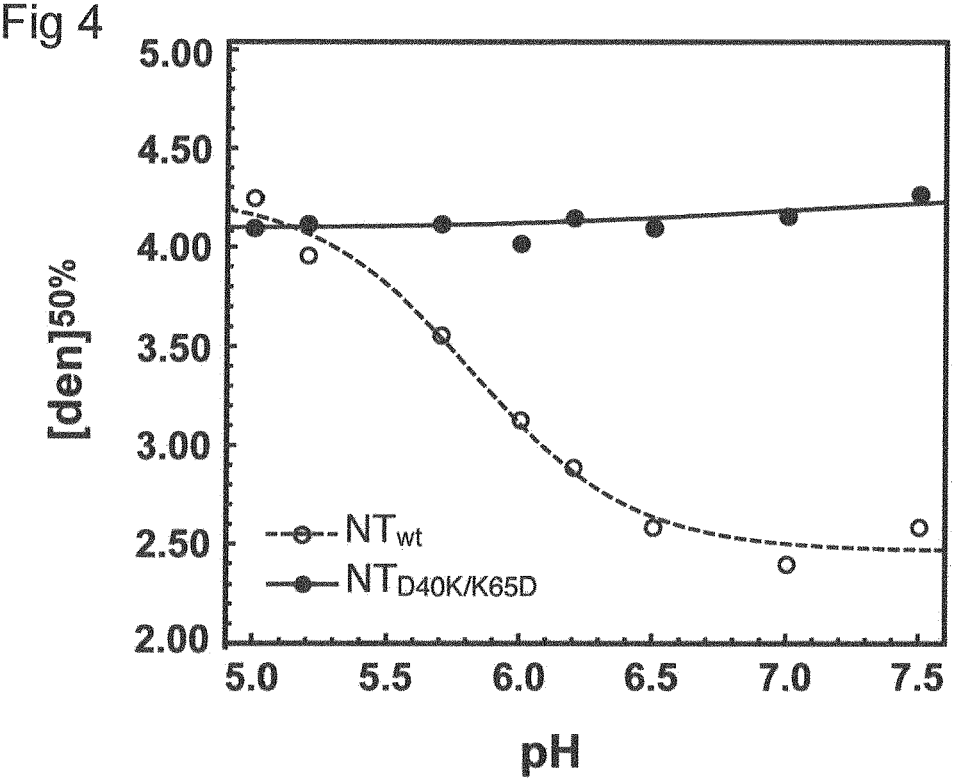
FIG. 4 shows the urea-induced denaturation of NT$_{wt}$ and NT$_{D40K/K65D}$ as a measure of stability.
Figure 5:
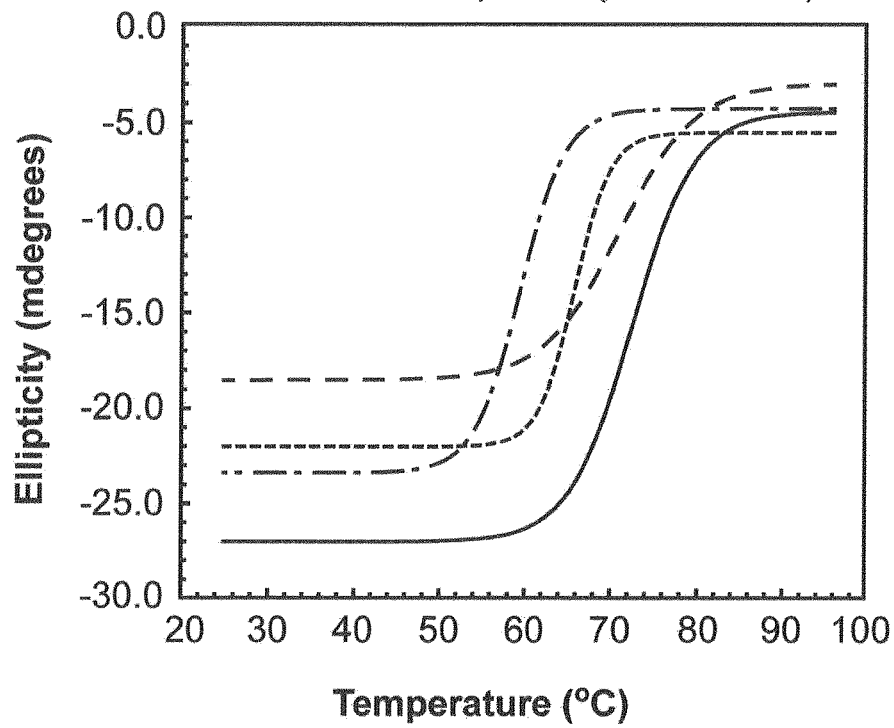
FIG. 5 shows thermal stability of NT$_{wt}$ and NT$_{D40K/K65D}$ measured with CD spectroscopy.
Figure 6:
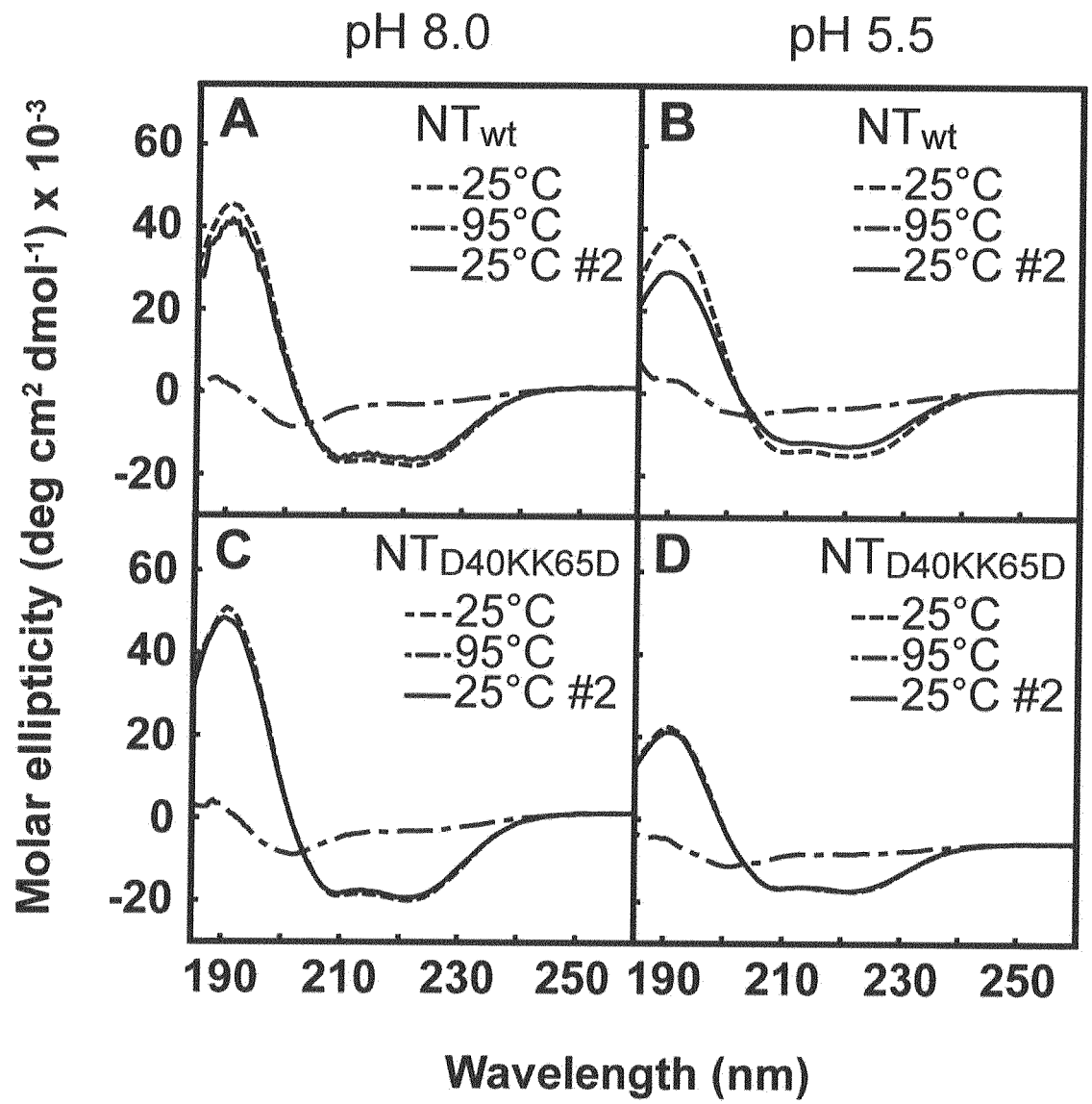
FIG. 6 shows refolding capacity of NT$_{wt}$ and NT$_{D40K/K65D}$ measured with CD spectroscopy.

The present invention is concerned with production and expression of proteins and polypeptides. Depending on the purpose with this production, the end product may vary. It may for instance be desirable to obtain the desired protein or polypeptide inserted in a lipid membrane, in solution or associated with other biomolecules. It shall also be realized that it may also be highly desirable to obtain the desired protein or polypeptide as part of a fusion protein, which may provide a suitable handle for purification and detection and/or provide desirable properties, e.g. stability and solubility. Maintaining the desired protein or polypeptide functionally integrated in a soluble fusion protein is useful to characterize and study the desired protein or polypeptide.

The present invention is generally based on the insight of the usefulness of a specific variant of the N-terminal (NT) fragment of a spider silk protein due to its surprising capacity to be present as a soluble monomer regardless of the pH of the surrounding aqueous medium, and its excellent properties as a fusion partner due to its extraordinary high solubility.

Spider silk consists mainly of large and aggregation-prone proteins (spidroins) that are produced in abdominal glands of spiders. They are built up from extensive and mainly hydrophobic stretches of repeated alanine- and glycine-rich segments flanked by globular and hydrophilic domains at the N-terminal (NT) and C-terminal (CT) end. During spinning, spidroins are passaged through a narrowing duct and convert from soluble protein into solid fibers in a process that involve precise control of the environmental conditions including level of hydration, shear forces, ion composition, pH and carbon dioxide pressure. Despite their aggregation-prone nature, spidroins are stored at a remarkably high concentration (30-50% w/w) in the spider silk gland.

The NT domain is the most conserved part of spidroins and folds into a soluble ~130 residue 5-helix bundle with a dipolar charge distribution. Furthermore, NT has an important role in fiber formation as it forms anti-parallel dimers at pH below 6.5, which is considered to be a critical step for interconnecting spidroin micelles in the spinning duct.

In known spider MaSp1 and MaSp2 silk protein species (see e.g. FIG. 1), D40 and K65 of the NT moiety (SEQ ID NO: 9) are conserved and mediate intersubunit electrostatic interactions by salt bridges between the side chains of the negatively charged D40 and the positively charged K65, which stabilizes the dimer configuration. Similarly, there are corresponding oppositely charged amino acid residues in known minor ampullate spider silk (MiSp) species. It has now been realized and demonstrated in the Examples that charge-reversing mutations of these residues to provide a positively charged (basic) amino acid residue in position 40 and a negatively charged (acidic) amino acid residue in position 65 surprisingly abolish the intersubunit salt bridges between these positions, which in turn has a critical impact on the pH-dependent dimerization capacity of the NT fragment. As a result of these charge-reversing mutations, the NT mutant surprisingly becomes a stable monomer over a broad pH interval and attains excellent properties as a fusion partner, including high expression, high stability and pH insensitivity of the resulting fusion protein together with the desired protein or polypeptide. The NT mutant is highly soluble in water. The high expression levels of the resulting fusion proteins using the charge-reversed NT mutant according to the present invention are particularly surprising considering that another known NT variant, $NT_{A72R}$, achieves lower expression levels than $NT_{wt}$ of the corresponding fusion proteins. Without desiring to be bound to any particular scientific theory, it is suggested that the improved stability and refolding capacity of the charge-reversed mutant NT according to the present invention can be explained by the less dipolar charge distribution that reduces destabilizing charge clusters.

The yields of soluble fusion proteins after expression in E. coli are typically at least 2 times higher compared to conventional tags like thioredoxin and PGB1, and the fusion proteins can be purified to homogeneity, e.g. by salt precipitation and/or precipitation in an organic solvent. The cleaved off desired proteins or peptides are active, e.g. in an animal model of disease. The charge reversed NT mutant is unable to dimerize, stabilized, hypersoluble, yields higher amounts of fusion proteins, and enables production of aggregation-prone proteins that have previously been refractory to recombinant production.

Without desiring to be limited to any specific theory, the experimental results disclosed herein support that recombinant production of desired peptides or proteins can be enhanced using the charge-reversed NT mutant according to the invention as a fusion tag that mediates solubility and shields hydrophobic regions of the desired protein from the aqueous surrounding within micelle-like particles. The mutant $NT_{D40K/K65D}$ is unable to dimerize at low pH due to a reduced dipolar charge distribution and is therefore able to mediate solubility in a wider pH range. Interestingly, size exclusion chromatography of $NT_{D40K/K65D}$-SP-C33Leu (FIG. 19) shows that that the purified amphipathic fusion protein arrange into 510 kDa assemblies and micelle-like particles around 10-15 nm in size are observed by TEM (FIG. 20).

It is therefore considered that the formation of micelles, or micelle-like particles, comprising or consisting of fusion proteins comprising the charge-reversed NT mutant according to the invention are a useful intermediate structure in the recombinant production of desirable proteins and polypeptides, in particular of hydrophobic proteins and polypeptides and proteins and polypeptides with hydrophobic regions, e.g. membrane proteins and polypeptides and membrane-associated proteins and polypeptides. The micelles typically have a size in the range of 5-100 nm, such as 5-30 nm, and preferably 5-20 or 10-15 nm.

Membrane-associated proteins and numerous other commercially relevant proteins are difficult to produce and purify in their native form due to their hydrophobic and aggregation-prone nature. The lack of sustainable and generic production regimes makes these proteins difficult to manufacture and evaluate, e.g. as pharmaceuticals. The charge-reversed NT mutant according to the invention without the ability to dimerize demonstrated an improved stability and refolding capacity and was used as a highly soluble fusion partner for production of surfactant peptide analogues SP-C33Leu, KL4, surfactant proteins SP-A and SP-D and truncated variants thereof, the amyloid-forming polypeptides β17, Aβ and IAPP, hCAP18, nicastrin, eGFP and the Bri2-BRICHOS protein domain. The obtained amounts of fusion proteins were up to 8-fold higher compared to PGB1 fusion proteins, and all peptides/proteins could be produced as soluble and functional protein after removal of the NT domain.

The use of fusion partners in large-scale heterologous protein production is uncommon, mainly due to the need of additional expensive chromatographic steps and/or difficulties in removing the fusion partner. However, NT and charge-reversed NT allow for efficient purification of hydrophobic target peptides using simple NaCl precipitation and an ethanol extraction step that circumvents the need for chromatography. The procedure described herein represents a cheap, efficient and, from a regulatory point of view, beneficial way of producing proteins, e.g. non-animal derived SP-C33Leu for clinical use in synthetic lung surfactants. It is shown herein that recombinant SP-C33Leu is identical to the synthetic peptide and a mixture of recombinant SP-C33Leu and synthetic phospholipids is similar to the porcine derived surfactant Curosurf® in terms of function in an animal model of respiratory distress.

The surfactant proteins SP-A and SP-D do not insert into membranes but rather play a role in the pulmonary immune response through their carbohydrate-binding domains. Although the proteins are hydrophilic, they are reluctant to recombinant production. Using charge-reversed NT as a fusion partner enables high expression and subsequent purification of soluble derivatives of SP-A and SP-D. This shows that charge-reversed NT works as a general solubility-enhancing fusion partner for biotechnical applications, enabling heterologous production of TM peptides as well as proteins that today are difficult to produce due to their hydrophobicity or aggregation propensity.

Thus, the present invention provides according to a first aspect a protein comprising a moiety of 100-160 amino acid residues having at least 70% identity with SEQ ID NO: 1 or SEQ ID NO: 96, wherein the amino acid residue corresponding to position 40 in SEQ ID NO: 1 is a basic amino residue, selected from the group consisting of Lys, Arg and His; and wherein the amino acid residue corresponding to position 65 in SEQ ID NO: 1 is an acidic amino acid residue, selected from the group consisting of Asp and Glu.

Wildtype NT is highly water-soluble and useful e.g. as a solubility-increasing moiety in a fusion protein for the expression of a desired protein or polypeptide, but it also form dimers at a pH interval of 5.5-7.2 which increases the risk of undesirable aggregation of the fusion proteins. This is a useful pH interval for the functionality and stability of certain desirable proteins and polypeptides. It is also a useful pH interval for certain purification protocols, e.g. when using ion exchange, such as cation or anion exchange, or immobilized metal ion affinity chromatography (IMAC) as a purification principle. It is also a useful pH interval for certain expression hosts, e.g. yeasts. It has now been realized that the charge-reversed double mutant NT according to the invention decreases the capacity of the protein to form dimers, without adversely affecting its solubility or its capacity to increase the solubility of a desired protein or polypeptide when they are linked in a fusion protein. The mutant NT protein according to the invention is therefore useful in itself to study the physiologically relevant NT monomer as such. The mutant NT protein according to the invention is also useful as a solubility-increasing moiety in a fusion protein, since it decreases the risk of undesirable aggregation of the fusion proteins, and thereby opens up a new pH window (5.5-7.2) in which charge-reversed double mutant NT from spider silk protein can be used in biochemical applications when solubility of protein/polypeptide monomers in aqueous solutions is desirable, e.g. in production or characterization of desirable proteins or polypeptides. It has surprisingly been determined from experimental data that although these changes in positions 40 and 65 do not alter the net charge of the resulting protein, its capacity to provide stability and solubility to any desirable protein/polypeptide moiety to which it is fused is improved.

In a preferred embodiment, the fusion protein according to the invention is present as micelles or micelle-like particles. The micelles typically have a size in the range of 5-100 nm, such as 5-30 nm, 5-20 nm, or 10-15 nm. This intermediate micellar structure is believed to support the high stability and solubility, and ultimately the high yield, of the fusion proteins, and in particular of fusion proteins comprising hydrophobic proteins and polypeptides as well as proteins and polypeptides with hydrophobic regions, thus protecting the water-insoluble peptide during expression and purification in aqueous solvents. The micelles typically have a size in the range of 5-100 nm, such as 5-30 nm, and preferably 5-20 nm or 10-15 nm.

In a preferred embodiment, the amino acid residue corresponding to position 40 in SEQ ID NO: 1 is Lys or Arg, and preferably Lys. In one preferred embodiment, the amino acid residue corresponding to position 65 in SEQ ID NO: 1 is Asp. The six possible and preferred variants regarding these two positions are presented as SEQ ID NO: 2-7. A particularly preferred variant is SEQ ID NO: 2, wherein the amino acid residue corresponding to position 40 in SEQ ID NO: 1 is Lys; and wherein the amino acid residue corresponding to position 65 in SEQ ID NO: 1 is Asp. For avoidance of doubt, the corresponding mutated positions in SEQ NO: 2-7 are positions 36 and 61 due to a shorter N-terminal end.

In preferred embodiments, the amino acid residue corresponding to position 72 in SEQ ID NO: 1 is not Arg. It is preferably a non-charged residue, i.e. not Lys, Arg, His, Glu or Asp. In certain preferred embodiments, the amino acid residue corresponding to position 72 in SEQ ID NO: 1 is selected from the group consisting of Ala, Val, Phe, Pro, Leu, Ile, Trp, Met, Cys and Gly; and preferably Ala, Val, Leu, Ile and Gly. In a preferred embodiment, the amino acid residue corresponding to position 72 in SEQ ID NO: 1 is Ala or Gly, preferably Ala.

As set out above, the inventive moiety is derived from the NT fragment of a spider silk protein, or spidroin. Although the examples by necessity relate to specific NT fragments, in this case proteins derived from major spidroin 1 (MaSp1) from *Euprosthenops australis*, it is considered that the method disclosed herein is applicable to any similar protein moiety. The terms "spidroins" and "spider silk proteins" are used interchangeably throughout the description and encompass all known spider silk proteins, including major ampullate spider silk proteins which typically are abbreviated "MaSp", or "ADF" in the case of *Araneus diadematus*, and minor ampullate spider silk proteins, typically abbreviated "MiSp". The major ampullate spider silk proteins are generally of two types, 1 and 2. These terms furthermore include the new NT protein fragments according to the invention, as defined in the appended claims and itemized embodiments, and other non-natural proteins with a high degree of identity and/or similarity to the known spider silk NT protein fragments.

The inventive moiety has a high degree of similarity to the N-terminal (NT) amino acid sequence of spider silk proteins. As shown in FIG. 1, these amino acid sequences are well conserved among various species and spider silk proteins, including MaSp1, MaSp2 and MiSp. The skilled person is therefore well aware how, and to what extent, the amino acid sequence may be varied without departing from the properties and functionality of the N-terminal spider silk protein fragment. Table 1 lists the spidroin NT fragments which are aligned in FIG. 1 and other inventive NT moieties, denoted with GenBank accession entries.

TABLE 1

Spidroin NT fragments

| Code | Species and spidroin protein | GenBank acc. no. | SEQ ID NO |
|---|---|---|---|
| Ea MaSp1 | *Euprosthenops australis* MaSp 1 | AM259067 | 13 |
| Lg MaSp1 | *Latrodectus geometricus* MaSp 1 | ABY67420 | 14 |
| Lh MaSp1 | *Latrodectus hesperus* MaSp 1 | ABY67414 | 15 |
| Nc MaSp1 | *Nephila clavipes* MaSp 1 | ACF19411 | 16 |
| At MaSp2 | *Argiope trifasciata* MaSp 2 | AAZ15371 | 17 |
| Lg MaSp2 | *Latrodectus geometricus* MaSp 2 | ABY67417 | 18 |
| Lh MaSp2 | *Latrodectus hesperus* MaSp 2 | ABR68855 | 19 |
| Nim MaSp2 | *Nephila inaurata madagascariensis* MaSp 2 | AAZ15322 | 20 |
| Nc MaSp2 | *Nephila clavipes* MaSp 2 | ACF19413 | 21 |
| Ab CySp1 | *Argiope bruennichi* cylindriform spidroin 1 | BAE86855 | 22 |
| Ncl CySp1 | *Nephila clavata* cylindriform spidroin 1 | BAE54451 | 23 |
| Lh TuSp1 | *Latrodectus hesperus* tubuliform spidroin | ABD24296 | 24 |
| Nc Flag | *Nephila clavipes* flagelliform silk protein | AF027972 | 25 |
| Nim Flag | *Nephila inaurata madagascariensis* flagelliform silk protein | AF218623 (translated) | 26 |
| Av MiSp | *Araneus ventricosus* MiSp | AFV31615 | 96 |
| Lh MiSp | *Latrodectus hesperus* MiSp | ADM14321 | 97 |
| Ud MiSp | *Uloborus diversus* MiSp | ADM14326 | 98 |
| Mg MiSp | *Metepeira grandiosa* MiSp | ADM14328 | 99 |

Only the part corresponding to the N-terminal domain is shown for each sequence, omitting the signal peptide. Nc flag and Nlm flag are translated and edited according to Rising A. et al. Biomacromolecules 7, 3120-3124 (2006)).

It is not critical which specific NT moiety is present in the proteins according to the invention, as long as the NT moiety is not entirely missing. Thus, the NT moiety according to the invention can be selected from any of the MaSp1 or MaSp2 amino acid sequences shown in FIG. 1 or sequences with a high degree of similarity or MiSp amino acid sequences, such as SEQ ID NO: 96-99. A wide variety of sequences can be used in the fusion protein according to the invention. Based on the homologous sequences of FIG. 1, the following sequence constitutes a consensus MaSp NT amino acid sequence:

(SEQ ID NO: 10)
QANTPWSSPNLADAFINSF(M/L)SA(A/I)SSSGAFSADQLDDMST

IG(D/N/Q)TLMSAMD(N/S/K)MGRSG(K/R)STKSKLQALNMAFA

SSMAEIAAAESGG(G/Q)SVGVKTNAISDALSSAFYQTTGSVNPQFV (N/S)EIRSLI(G/N)M(F/L)(A/S)QASANEV.

The sequence of the inventive moiety according to the invention has preferably at least 50% identity, preferably at least 60% identity, to the consensus amino acid sequence SEQ ID NO: 10, which is based on the wildtype NT amino acid sequences of FIG. 1. In a preferred embodiment, the sequence of the inventive moiety according to the invention has at least 65% identity, preferably at least 70% identity, to the consensus amino acid sequence SEQ ID NO: 10. In preferred embodiments, the solubility-enhancing moiety according to the invention has furthermore 70%, preferably 80%, similarity to the consensus amino acid sequence SEQ ID NO: 10.

A representative inventive moiety according to the invention is SEQ ID NO: 2 (encoded by SEQ ID NO: 8), which is derived from the *Euprosthenops australis* NT moiety (SEQ ID NO: 9) with replacement of aspartic acid in position 40 with lysine or any other basic residue, and with replacement of lysine in position 65 with aspartic acid or any other acidic residue, as set out hereinabove and in SEQ ID NO: 1. According to a preferred embodiment of the invention, the inventive moiety furthermore has at least 70% identity, such as at least 75% identity, preferably at least 80% identity to SEQ ID NO: 1 or any of SEQ ID NO: 96-99 or any individual amino acid sequence in FIG. 1. In preferred embodiments of the invention, the inventive moiety has at least 85%, such as at least 90% or even 95% identity, to SEQ ID NO: 1: or any of SEQ ID NO: 96-99 or any individual amino acid sequence in FIG. 1. In preferred embodiments of the invention, the solubility-enhancing moiety is identical to SEQ ID NO: 9 or any of SEQ ID NO: 96-99 or any individual amino acid sequence in FIG. 1, with the proviso that acidic residue in position 40 and the basic residue in position 65 (or the corresponding positions as it may be) are replaced as set out hereinabove.

The term "% identity", as used throughout the specification and the appended claims, is calculated as follows. The query sequence is aligned to the target sequence using the CLUSTAL W algorithm (Thompson, J. D., Higgins, D. G. and Gibson, T. J., Nucleic Acids Research, 22: 4673-4680 (1994)). A comparison is made over the window corresponding to the shortest of the aligned sequences. The amino acid residues at each position are compared, and the percentage of positions in the query sequence that have identical correspondences in the target sequence is reported as % identity.

The term "% similarity", as used throughout the specification and the appended claims, is calculated as described for "% identity", with the exception that the hydrophobic residues Ala, Val, Phe, Pro, Leu, Ile, Trp, Met and Cys are similar; the basic residues Lys, Arg and His are similar; the acidic residues Glu and Asp are similar; and the hydrophilic, uncharged residues Gln, Asn, Ser, Thr and Tyr are similar. The remaining natural amino acid Gly is not similar to any other amino acid in this context.

Throughout this description, alternative embodiments according to the invention fulfill, instead of the specified percentage of identity, the corresponding percentage of similarity. Other alternative embodiments fulfill the specified percentage of identity as well as another, higher percentage of similarity, selected from the group of preferred percentages of identity for each sequence. For example, a sequence may be 70% similar to another sequence; or it may be 70% identical to another sequence; or it may be 70% identical and 90% similar to another sequence.

The inventive moiety contains from 100 to 160 amino acid residues. It is preferred that the inventive moiety contains at least 100, or more than 110, preferably more than 120, amino acid residues. It is also preferred that the inventive moiety contains at most 160, or less than 140 amino acid residues. A typical inventive moiety contains approximately 130-140 amino acid residues.

As set out in detail in WO 2011/115538 which is incorporated in its entirety herein, the N-terminal (NT) fragment of a spider silk protein is particularly useful as a solubility-enhancing moiety in a fusion protein that is produced from recombinant DNA. According to a further aspect, the present invention is further based on the insight of the usefulness of the charge-reversed double mutant NT according to the invention in such a fusion protein due to its capacity to be present as a soluble monomer regardless of the pH of the surrounding aqueous medium. The resulting fusion protein is surprisingly stable and can be produced in high yield.

According to this aspect, the present invention provides a fusion protein comprising (i) at least one solubility-enhancing moiety of 100-160 amino acid residues having at least 70% identity with SEQ ID NO: 1 or SEQ ID NO: 96, wherein the amino acid residue corresponding to position 40 in SEQ ID NO: 1 is selected from the group consisting of Lys, Arg and His; and wherein the amino acid residue corresponding to position 65 in SEQ ID NO: 1 is selected from the group consisting of Asp and Glu; and (ii) at least one moiety which is a desired protein or polypeptide. Preferred features of the solubility-enhancing moiety are presented hereinabove. It has surprisingly been determined from experimental data that although these changes in positions 40 and 65 of the solubility-enhancing moiety do not alter the net charge of the resulting fusion protein, its capacity to provide stability and solubility to any desirable protein/polypeptide moiety to which it is fused is improved, and the solubility-enhancing moieties of the fusion protein are surprisingly prevented from dimerizing since electrostatic interactions involving the oppositely charged residues 40 and 65 are not formed.

In a preferred embodiment, the fusion proteins consists of (i) at least one solubility-enhancing moiety of 100-160 amino acid residues having at least 70% identity with SEQ ID NO: 1 or SEQ ID NO: 96, wherein the amino acid residue corresponding to position 40 in SEQ ID NO: 1 is selected from the group consisting of Lys, Arg and His; and wherein the amino acid residue corresponding to position 65 in SEQ ID NO: 1 is selected from the group consisting of Asp and Glu; and (ii) at least one moiety which is a desired protein or polypeptide, optionally including other preferred features disclosed herein, e.g. a linker peptide and/or a cleavage site between the solubility-enhancing moiety and the desired protein or polypeptide. In experiments, high yields of different fusion proteins have been achieved in *E. coli*. The fusion protein may be useful as such in isolated form, e.g. for studies of otherwise aggregated or poorly soluble proteins in soluble form, or in crystallization associated with X-ray crystallography. The fusion protein may also be cleaved to release the desired protein or polypeptide.

The term "fusion protein" implies here a protein that is made by expression from a recombinant nucleic acid, i.e. DNA or RNA that is created artificially by combining two or more nucleic acid sequences that would not normally occur together (genetic engineering). The fusion proteins according to the invention are recombinant proteins, and they are therefore not identical to naturally occurring proteins. The combined nucleic acid sequences encode different proteins, partial proteins or polypeptides with certain functional properties. The resulting fusion protein, or recombinant fusion protein, is a single protein with functional properties derived from each of the original proteins, partial proteins or polypeptides.

In certain embodiments, the fusion protein according to the invention and the corresponding genes are chimeric, i.e. the protein/gene fragments are derived from at least two different species. The solubility-enhancing moiety is derived from the N-terminal fragment of a spider silk protein.

According to this aspect, it is preferred that the desired protein or polypeptide is a non-spidroin protein. This implies that the desired protein or polypeptide is not derived from the C-terminal, repetitive or N-terminal fragment of a spider silk protein. According to another aspect, it is preferred that the desired protein or polypeptide is a spidroin protein. This implies that the desired protein or polypeptide is derived from the C-terminal, repetitive or N-terminal fragment of a spider silk protein. The desired protein or polypeptide may also in turn be a fusion between a spidroin protein moiety and a non-spidroin polypeptide or protein moiety. Typically, the spidroin protein moiety provides the capacity of forming an ordered polymer, while the non-spidroin polypeptide or protein moiety may provide desirable affinity properties, e.g. cell-binding peptides, immunoglobulins and functional fragments thereof.

The fusion protein according to the invention may also contain one or more linker peptides. The linker peptide(s) may be arranged between the solubility-enhancing moiety and the desired protein or polypeptide moiety, or may be arranged at either end of the solubility-enhancing moiety and the desired protein or polypeptide moiety. If the fusion protein contains two or more solubility-enhancing moieties, the linker peptide(s) may also be arranged in between two solubility-enhancing moieties. The linker(s) may provide a spacer between the functional units of the fusion protein, but may also constitute a handle for identification and purification of the fusion protein, e.g. a His and/or a Trx tag. If the fusion protein contains two or more linker peptides for identification and purification of the fusion protein, it is preferred that they are separated by a spacer sequence, e.g. $His_6$-spacer-$His_6$-. The linker may also constitute a signal peptide, such as a signal recognition particle substrate, which directs the fusion protein to the membrane and/or causes secretion of the fusion protein from the host cell into the surrounding medium. The fusion protein may also include a cleavage site in its amino acid sequence, which allows for cleavage and removal of the linker(s) and/or the solubility-enhancing moiety or moieties. Various cleavage sites are known to the person skilled in the art, e.g. cleavage sites for chemical agents, such as CNBr after Met residues and hydroxylamine between Asn-Gly residues, cleavage sites for proteases, such as thrombin or protease 3C, and self-splicing sequences, such as intein self-splicing sequences. A preferred cleavage site is after a Met residue.

Each solubility-enhancing moiety is linked, directly or indirectly, to the desired protein or polypeptide moiety. A direct linkage implies a direct covalent binding between the two moieties without intervening sequences, such as linkers. An indirect linkage also implies that the two moieties are linked by covalent bonds, but that there are intervening sequences, such as linkers and/or one or more further solubility-enhancing moieties.

The at least one solubility-enhancing moiety may be arranged at either end of the desired protein or polypeptide, i.e. C-terminally arranged or N-terminally arranged. It is preferred that the least one solubility-enhancing moiety is arranged at the N-terminal end of the desired protein or polypeptide. If the fusion protein contains one or more linker peptide(s) for identification and purification of the fusion protein, e.g. a His or Trx tag(s), it is preferred that it is arranged at the N-terminal end of the fusion protein. The at least one solubility-enhancing moiety may also be integrated within the desired protein or polypeptide, for instance between domains or parts of a desired protein. In a preferred embodiment, at least one solubility-enhancing moiety constitutes the N-terminal and/or the C-terminal end of the fusion protein, i.e. no linker peptide or other sequence is present terminal of the solubility-enhancing moiety. A typical fusion protein according to the invention may contain 1-6, such as 1-4, such as 1-2 solubility-enhancing moieties.

In a preferred embodiment, the fusion protein is comprising at least two solubility-enhancing moieties, each being derived from the N-terminal (NT) fragment of a spider silk protein as set out hereinabove. The solubility-enhancing moieties, preferably two solubility-enhancing moieties, may be consecutively arranged at either end of the desired protein or polypeptide, i.e. C-terminally arranged or N-terminally arranged. Consecutively arranged solubility-enhancing moieties may also be integrated within the desired protein or polypeptide, for instance between domains or parts of a desired protein. The solubility-enhancing moieties may also be non-consecutively arranged, either at each end of the desired protein or polypeptide, i.e. C-terminally and N-terminally arranged, or at one end of the desired protein or polypeptide and integrated within the desired protein or polypeptide. A typical preferred fusion protein according to the invention may contain 2-6, such as 2-4 solubility-enhancing moieties.

In a preferred embodiment, the fusion protein according to the invention has at least one cleavage site arranged between at least one desired protein or polypeptide moiety and at least one solubility-enhancing moiety. This allows for cleavage of the fusion protein and purification of the desired protein. It is however noted that it may be desirable to obtain the desired protein or polypeptide as part of a fusion protein, which may provide a suitable handle for purification and detection and/or provide desirable properties, e.g. stability and solubility. In this case, the cleavage site may be omitted, or the cleavage site may be included but the cleavage step omitted.

A preferred fusion protein has the form of an N-terminally arranged solubility-enhancing moiety, coupled by a linker peptide of 1-30 amino acid residues, such as 1-10 amino acid residues, to a C-terminally arranged desired protein or polypeptide. The linker peptide may contain a cleavage site. Optionally, the fusion protein has an N-terminal or C-terminal linker peptide, which may contain a purification tag, such as a His tag, and a cleavage site.

Another preferred fusion protein has the form of an N-terminally arranged solubility-enhancing moiety coupled directly to a C-terminally arranged desired protein or polypeptide. Optionally, the fusion protein has an N-terminal or C-terminal linker peptide, which may contain a purification tag, such as a His tag, and a cleavage site.

One preferred fusion protein has the form of a two consecutive N-terminally arranged solubility-enhancing moieties, coupled by a linker peptide of 1-30 amino acid residues, such as 1-10 amino acid residues, to a C-terminally arranged desired protein or polypeptide. The linker peptide may contain a cleavage site. Optionally, the fusion protein has an N-terminal or C-terminal linker peptide, which may contain a purification tag, such as a His tag, and a cleavage site.

Another preferred fusion protein has the form of two consecutive N-terminally arranged solubility-enhancing moieties coupled directly to a C-terminally arranged desired protein or polypeptide. Optionally, the fusion protein has an N-terminal or C-terminal linker peptide, which may contain a purification tag, such as a His tag, and a cleavage site.

In the context of the present invention, it is understood that by a desired polypeptide is meant a polypeptide of 5-50 amino acid residues, preferably 10-50, 20-50 or 40-50 amino acid residues. Further in the context of the present invention, it is understood that by a desired protein is meant a protein of more than 50 amino acid residues, such as more than 80 amino acid residues. It is preferred that the desired protein contains less than 500 amino acid residues, such as less than 300 or less than 200 amino acid residues. Preferred sizes of the desired polypeptide or protein are in the ranges of 4-50 kDa, such as 5-50 kDa, 4-45 kDa and 5-45 kDa, preferably 8-30 kDa, and more preferably 4-20, 5-20 or 8-30 kDa.

In preferred embodiments of the invention, the desired polypeptide or protein is hydrophobic, having an aliphatic index of 65 or higher, preferably 70 or higher, as determined by Protparam (web.expasy.org/protparam/; Gasteiger E. et al.; Protein Identification and Analysis Tools on the ExPASy Server; (in) John M. Walker (ed): The Proteomics Protocols Handbook, Humana Press (2005). pp. 571-607). Preferably, the ratio of hydrophobic residues within the polypeptide, as defined by the Grand Average of Hydropathy (GRAVY) index (Kyte, J. and Doolittle, R. F. (1982) A simple method for displaying the hydropathic character of a protein. J. Mol. Biol. 157, 105-132.) should be between −1 and 2, preferably between 1 and 2.

In one preferred embodiment, the desired protein or polypeptide is selected from the group consisting of amyloid-forming proteins and polypeptides, disulphide-containing proteins and polypeptides, apolipoproteins, membrane proteins and polypeptides, protein and polypeptide drugs and drug targets, aggregation-prone proteins and polypeptides, proteases, and immunoglobulins and fragments thereof. In a preferred embodiment, the desired protein or polypeptide is selected from the group consisting of amyloid-forming proteins and polypeptides, disulphide-containing proteins and polypeptides, apolipoproteins, membrane proteins and polypeptides, protein and polypeptide drugs and drug targets, aggregation-prone proteins and polypeptides, and proteases.

One preferred group of desired proteins or polypeptides is consisting of Aβ-peptide, IAPP, PrP, α-synuclein, calcitonin, prolactin, cystatin, ATF, actin and β17; SP-B, mini-BLeu, α-defensins and β-defensins; class A-H apolipoproteins; LL-37, hCAP18, SP-C, SP-C33, SP-C33Leu, KL4, Brichos, GFP, eGFP, nicastrin, neuroserpin; hormones, including EPO and GH, and growth factors, including IGF-I and IGF-II; SP-A, SP-D and analogues thereof; Bri2-BRICHOS and variants thereof, including Bri2$_{113-231}$, avidin and streptavidin; protease 3C; and immunoglobulins and fragments thereof. A preferred group of desired proteins or polypeptides is consisting of Aβ-peptide, IAPP, PrP, α-synuclein, calcitonin, prolactin, cystatin, ATF, actin and β17; SP-B, mini-BLeu, α-defensins and β-defensins; class A-H apolipoproteins; LL-37, hCAP18, SP-C, SP-C33, SP-C33Leu, KL4, Brichos, GFP, eGFP, nicastrin, neuroserpin; hormones, including EPO and GH, and growth factors, including IGF-I and IGF-II; SP-A, SP-D and analogues thereof; Bri2-BRICHOS and variants thereof, including Bri2$_{113-231}$, avidin and streptavidin; and protease 3C.

Amyloid-forming proteins and polypeptides according to the invention include proteins and polypeptides that are associated with disease and functional amyloid. Examples of amyloid-forming proteins and polypeptides include amyloid beta peptide (Aβ-peptide), islet amyloid polypeptide (amylin or IAPP), prion protein (PrP), α-synuclein, calcitonin, prolactin, cystatin, atrial natriuretic factor (ATF) and actin. A further example is the designed polypeptide β17. Examples of amyloid-forming proteins and polypeptides according to the invention are listed in Table 2.

TABLE 2

Amyloid-forming proteins and polypeptides

| Protein | Uniprot ID/other reference |
|---|---|
| Aβ1-42 | P05067 |
| Apolipoprotein SAA | P02735 |
| Cystatin C | P01034 |
| Transthyretin | P02766 |
| Lysozyme | P61626 |
| α-synuclein | P37840 |
| Prion protein | P04156 |
| ODAM | A1E959 |
| Lactadherin | Q08431 |
| Tau | P10636 |
| Gelsolin | P06396 |
| ABri, ADan | Q9Y287 |
| Insulin | P01308 |
| Apolipoprotein A-II | P02652 |
| Apolipoprotein A-IV | P06727 |
| Semenogelin I | P04279 |
| Keratoepithelin | Q15582 |
| Lactotransferrin | P02788 |
| Fibrinogen α-chain | P02671 |
| ANF | P01160 |
| IAPP | P10997 |
| β2-microglobulin | P61769 |
| Calcitonin | P01258 |
| Prolactin | P01236 |
| Apolipoprotein A-I | P02647 |
| CsgA | P28307 |
| Sup35 | C7GN25 |
| Pmel17 | P40967 |
| HET-s | A8HR89 |
| Ure2p | Q8NIE6 |
| β17 | SEQ ID NO: 27 |

Examples of disulphide-containing proteins and polypeptides include surfactant protein B (SP-B) and variants thereof, such as Mini-B, Mini-B27, Mini-BLeu, α-defensins and β-defensins. Without being limited to any specific theory, it is contemplated that the solubility-enhancing moiety promotes the desired formation of intrachain disulphide bonds over interchain disulphide bonds in defensins and other disulphide-containing proteins and polypeptides.

Examples of disulphide-containing proteins and polypeptides according to the invention are listed in Table 3.

TABLE 3

Disulphide-containing proteins and polypeptides

| Protein | Sequence/Uniprot ID |
|---|---|
| Human SP-B (SEQ ID NO 28) | FPIPLPYCWLCRALIKRIQAMIPKGALA VAVAQVCRVVPLVAGGICQCLAERYSVI LLDTLLGRMLPQLVCRLVLRCSM [a] |
| Mouse SP-B (SEQ ID NO 29) | LPIPLPFCWLCRTLIKRVQAVIPKGVLA VAVSQVCHVVPLVVGGICQCLAERYTVL LLDALLGRVVPQLVCGLVLRCST [a] |
| Pig SP-B (SEQ ID NO 30) | FPIPLPFCWLCRTLIKRIQAVVPKGVLL KAVAQVCHVVPLPVGGICQCLAERYIVI CLNMLLDRTLPQLVCGLVLRCSS [a] |
| Rabbit SP-B (SEQ ID NO 31) | FPIPLPLCWLCRTLLKRIQAMIPKGVLA MAVAQVCHVVPLVVGGICQCLAERYTVI LLEVLLGHVLPQLVCGLVLRCSS [a] |
| Rat SP-B (SEQ ID NO 32) | LPIPLPFCWLCRTLIKRVQAVIPKGVLA VAVSQVCHVVPLVVGGICQCLAERYTVL LLDALLGRVVPQLVCGLVLRCST [a] |
| Mini-B (SEQ ID NO 33) | CWLCRALIKRIQAMIPKGGRMLPQLVCR LVLRCS [b] |

TABLE 3-continued

Disulphide-containing proteins and polypeptides

| Protein | Sequence/Uniprot ID |
|---|---|
| Mini-BLeu (SEQ ID NO 34) | CWLCRALIKRIQALIPKGGRLLPQLVCR LVLRCS [b] |
| Mini-B27 (SEQ ID NO 35) | CLLCRALIKRFNRYLTPQLVCRLVLRC [c] |
| 1a AA (SEQ ID NO 36) | CWLARALIKRIQALIPKGGRLLPQLVAR LVLRCS [d] |
| 1b AA (SEQ ID NO 37) | AWLCRALIKRIQALIPKGGRLLPQLVCR LVLRAS [e] |
| 1a LL (SEQ ID NO 38) | CWLLRALIKRIQALIPKGGRLLPQLVLR LVLRCS [d] |
| 1b LL (SEQ ID NO 39) | LWLCRALIKRIQALIPKGGRLLPQLVCR LVLRLS [e] |
| Proinsulin | P01308 |
| CAR D1 [f] | P78310 |

[a] Cys8-Cys77, Cys11-Cys71, Cys35-Cys46 and intermolecular Cys48-Cys48 linkages
[b] Cys1-Cys33 and Cys4-Cys27 linkages
[c] Cys1-Cys27 and Cys4-Cys21 linkages
[d] Cys1-Cys33 linkage
[e] Cys4-Cys27 linkage
[f] Coxsackievirus and adenovirus receptor Examples of apolipoproteins include class A-H apolipoproteins. Examples of apolipoproteins according to the invention are listed in Table 4.

TABLE 4

Apolipoproteins

| Protein | Sequence/Uniprot ID |
|---|---|
| Apolipoprotein B-100 | P04114 |
| Apolipoprotein C-1 | P02654 |
| Apolipoprotein D | P05090 |
| Apolipoprotein E | P02649 |

Examples of membrane proteins and polypeptides include membrane-associated receptors, including cytokine receptors, KL4, LL-37, hCAP18, surfactant protein C (SP-C) and variants thereof, such as SP-C(Leu), SP-C33, SP-C30 and SP-C33Leu. Other specific examples include SP-C33Leu fused to Mini-B, Mini-BLeu, 1a AA, 1b AA, 0 AAAA, 1a LL, 1b LL, 0 LLLL or SP-B proteins, optionally via a linker, e.g. $Gly_n$, $Leu_n$, $Gly-Ala_n$ or the like. SP-C33Leu may be arranged N-terminal or, preferably, C-terminal to the Mini-B, Mini-BLeu, 1a AA, 1b AA, 0 AAAA, 1a LL, 1b LL, 0 LLLL or SP-B protein.

Examples of membrane proteins and polypeptides according to the invention are listed in Table 5.

TABLE 5

Membrane proteins and polypeptides

| Protein | SEQ ID NO | Sequence |
|---|---|---|
| SP-C | 40 | FGIPCCPVHLKRLLIVVV VVLIVVVIVGALLMGL * |
| SP-C(Leu) | 41 | FGIPSSPVHLKRLKLLLLL LLLILLLILGALLMGL |
| SP-C33 | 42 | IPSSPVHLKRLKLLLLLLL LILLLILGALLMGL |
| SP-C30 | 43 | IPSSPVHLKRLKLLLLLLL LILLLILGALL |
| SP-C33(Leu) | 44 | IPSSPVHLKRLKLLLLLLL LILLLILGALLLGL |
| LL-37 | 45 | LLGDFFRKSKEKIGKEFKR IVQRIKDFLRNLVPRTES |
| KL4 | 46 | KLLLLKLLLLKLLLLKLLL LK |

| Protein | Uniprot ID |
|---|---|
| Growth hormone receptor | P10912 |
| G-protein coupled receptor 35 | Q9HC97 |
| Insulin receptor, | P06213 |
| Gonadotropin releasing hormone receptor | P30968 |
| Very low density lipoprotein receptor | P98155 |
| TGF-beta receptor, type 1 | P36897 |
| Prostaglandin D2 receptor | Q13258 |
| Receptor tyrosine-protein kinase erbB-2 (HER2) | P04626 |
| Receptor tyrosine-protein kinase erbB-4 (HER4) | Q15303 |
| Receptor tyrosine-protein kinase erbB-3 (HER3) | P21860 |
| Aquaporin-1 | P29972 |
| Aquaporin-2 | P41181 |
| Chloride channel protein ClC-Ka | P51800 |
| Chloride channel protein ClC-Kb | P51801 |
| Integral membrane protein DGCR2/IDD | P98153 |
| Interleukin 9 receptor | Q01113 |

* Cys-5 and Cys-6 in native SP-C are palmitoylated

Examples of protein and polypeptide drugs and drug targets include hormones that are produced recombinantly, including peptide and protein hormones, such as erythropoietin (EPO) and growth hormone (GH), cytokines, growth factors, such as insulin-like growth factors (IGF-I and IGF-II), KL4, LL-37, hCAP18, surfactant protein C (SP-C) and variants thereof, such as SP-C(Leu), SP-C33, SP-C30, SP-C33Leu. Other specific examples include SP-C33Leu fused to Mini-B, Mini-BLeu, 1a AA, 1b AA, 0 AAAA, 1a LL, 1b LL, 0 LLLL or SP-B proteins, optionally via a linker, e.g. $Gly_n$, $Leu_n$, $Gly-Ala_n$ or the like. SP-C33Leu may be arranged N-terminal or, preferably, C-terminal to the Mini-B, Mini-BLeu, 1a AA, 1b AA, 0 AAAA, 1a LL, 1b LL, 0

LLLL or SP-B protein. Further preferred examples include surfactant proteins A (SP-A) and D (SP-D), and analogues thereof. A further preferred example is Bri2-BRICHOS and variants thereof, including Bri2$_{113-231}$, and nicastrin.

Examples of protein and polypeptide drugs and drug targets according to the invention are listed in Table 6.

TABLE 6

| Protein and polypeptide drugs and drug targets | |
|---|---|
| Protein | Sequence/ Uniprot ID/other reference |
| Insulin-like growth factor IA | P01243 |
| Insulin like growth factor IB | P05019 |
| Growth hormone 1, variant 1 | Q6IYF1 |
| Growth hormone 1, variant 2 | Q6IYF0 |
| Growth hormone 2, variant 2 | B1A4H7 |
| Insulin | P01308 |
| Erythropoietin | P01588 |
| Coagulation Factor VIII | P00451 |
| Coagulation Factor IX | P00740 |
| Prothrombin | P00734 |
| Serum albumin | P02768 |
| Antithrombin III | P01008 |
| Interferon alfa | P01563 |
| Somatotropin | P01241 |
| Major pollen allergen Bet v 1-A | P15494 |
| OspA (*Piscirickettsia salmonis*) | Q5BMB7 |
| 17 kDa antigen variant of OspA (*P. salmonis*) | Q9F9K8 |
| Transforming growth factor beta-1 | P01137 |
| Transforming growth factor beta-2 | P61812 |
| Transforming growth factor beta-3 | P10600 |
| Interleukin 1 beta | P01584 |
| Interleukin 1 alfa | P01583 |
| Interleukin 2 | P60568 |
| Interleukin 3 | P08700 |
| Interleukin 4 | P05112 |
| Interleukin 5 | P05113 |
| Interleukin 6 | P05231 |
| Interleukin 7 | P13232 |
| Interleukin 8 | P10145 |
| Interleukin 9 | P15248 |
| Interleukin 10 | P22301 |
| Interleukin 12 subunit alfa | P29459 |

TABLE 6-continued

| Protein and polypeptide drugs and drug targets | |
|---|---|
| Interleukin 12 subunit beta | P29460 |
| Interleukin 18 | Q14116 |
| Interleukin 21 | Q9HBE4 |
| Thymic stromal lymphopoietin | Q969D9 |
| hSP-A1 | Q8IWL2 |
| hSP-A1$_{81-228}$ | SEQ ID NO 47: |
| hSP-A2 | Q8IWL1 |
| hSP-A2$_{81-228}$ | SEQ ID NO 48: |
| hSP-D | P35247 |
| hSP-D$_{204-355}$ | SEQ ID NO 49 |
| Nicastrin | Q92542 |
| Bri2$_{113-231}$ (Bri2-Brichos) | SEQ ID NO 50 |
| Neuroserpin | SEQ ID NO 51 |

| Protein | SEQ ID NO | Sequence |
|---|---|---|
| SP-C | 40 | FGIPCCPVHLKRLLIVVVVVLIV VVIVGALLMGL [a] |
| SP-C(Leu) | 41 | FGIPSSPVHLKRLKLLLLLLLLIL LLILGALLMGL |
| SP-C33 | 42 | IPSSPVHLKRLKLLLLLLLLILLL ILGALLMGL |
| SP-C30 | 43 | IPSSPVHLKRLKLLLLLLLLILLL ILGALL |
| SP-C33(Leu) | 44 | IPSSPVHLKRLKLLLLLLLLILLL ILGALLLGL |
| LL-37 | 45 | LLGDFFRKSKEKIGKEFKRIVQRI KDFLRNLVPRTES |
| KL4 | 46 | KLLLLKLLLLKLLLLKLLLLK |
| 1a AA | 36 | CWLARALIKRIQALIPKGGRLLPQ LVARLVLRCS [b] |
| 1b AA | 37 | AWLCRALIKRIQALIPKGGRLLPQ LVCRLVLRAS [c] |
| 0 AAAA | 52 | AWLARALIKRIQALIPKGGRLLPQ LVARLVLRAS |
| 1a LL | 38 | CWLLRALIKRIQALIPKGGRLLPQ LVLRLVLRCS [b] |
| 1b LL | 39 | LWLCRALIKRIQALIPKGGRLLPQ LVCRLVLRLS [c] |
| 0 LLLL | 53 | LWLLRALIKRIQALIPKGGRLLPQ LVLRLVLRLS |

[a] Cys-5 and Cys-6 in native SP-C are palmitoylated
[b] Cys1-Cys33 linkage
[c] Cys4-Cys27 linkage Examples of aggregation-prone proteins and polypeptides include avidin, streptavidin and extracellular, ligand-binding parts of cytokine receptors.

Examples of aggregation-prone proteins and polypeptides according to the invention are listed in Table 7.

TABLE 7

Aggregation-prone proteins and polypeptides

| Protein | Uniprot ID/ other reference |
|---|---|
| Streptavidin, *Streptomyces avidinii* | P22629 |
| Streptavidin, *Streptomyces lavendulae* | B8YQ01 |
| Streptavidin V1, *Streptomyces venezuelae* | Q53532 |
| Streptavidin V2, *Streptomyces venezuelae* | Q53533 |
| Putative streptavidin, *Burkholderia mallei* (strain SAVP1) | A1V7Z0 |
| Putative streptavidin, *Burkholderia thailandensis* | Q2T1V4 |
| Putative streptavidin, *Burkholderia mallei* | Q62EP2 |
| Core streptavidin | GenBank: CAA77107.1 |
| M4 (quadruple mutein of streptavidin) | J Biol Chem 280(24): 23225-23231 (2005) |
| Avidin, *Gallus gallus* | P02701 GenBank: CAC34569.1 |
| Actin | P68133 |
| Interleukin 6 receptor subunit alfa | P08887 |
| Interleukin 6 receptor subunit beta | P40189 |
| Interleukin 2 receptor subunit alfa | P01589 |
| Interleukin 2 receptor subunit beta | P14784 |
| Cytokine receptor common subunit gamma | P31785 |
| Green Fluorescent Protein (GFP) | SEQ ID NO 54 |
| eGFP | SEQ ID NO 55 |

Examples of proteases include protease 3C from coxsackie virus or human rhinovirus. Further examples of proteases according to the invention are listed in Table 8.

TABLE 8

Proteases

| Protease | Class | Accession no. |
|---|---|---|
| Trypsin (bovine) | serine | P00760 |
| Chymotrypsin (bovine) | serine | P00766 |
| Elastase (porcine) | serine | P00772 |
| Endoproteinase Arg-C (mouse submaxillary gland) | serine | |
| Endoproteinase Glu-C (V8 protease) (*Staphylococcus aureus*) | serine | P04188 |
| Acylamino-acid-releasing enzyme (porcine) | serine | P19205 |
| Carboxypeptidase (*Penicillium janthinellum*) | serine | P43946 |
| Proteinase K (*Tritirachium album*) | serine | P06873 |
| Subtilisin (*Bacillus subtilis*) | serine | P04189 P29122 |
| Carboxypeptidase Y (yeast) | serine | P00729 |
| Endoproteinase Lys-C (*Lysobacter enzymogenes*) | serine | S77957 |
| Enteropeptidase (human) | serine | P98073 |
| Prothrombin | serine | P00734 |
| Factor X | serine | P00742 |
| Pepsin | aspartic | P00791 P00790 |
| Cathepsin D (human) | aspartic | P07339 |
| HIV-1 protease | aspartic | Q9YQ34 |
| Cathepsin C | cysteine | |
| Clostripain (endoproteinase-Arg-C) (*Clostridium histolyticum*) | cysteine | P09870 |
| Papain (*Carica papaya*) | cysteine | P00784 |
| Protease 3C | cysteine | Q04107 |
| Tobacco Etch virus (TEV) | cysteine | Q0GDU8 |
| Thermolysin (*Bacillus thermo-proteolyticus*) | metallo | P00800 |
| Endoproteinase Asp-N (*Pseudomonas fragi*) | metallo | Q9R4J4 |
| Carboxypeptidase A (bovine) | metallo | P00730 |
| Carboxypeptidase B (porcine) | metallo | P00732 |
| IgA protease | metallo | Q97QP7 |

In preferred embodiments of the invention, the desired protein or polypeptide is selected from surfactant protein B (SP-B) and variants thereof, such as Mini-B, Mini-B27, Mini-BLeu and KL4; Aβ, IAPP, β17; LL-37, hCAP18; surfactant protein C (SP-C) and variants thereof, such as SP-C(Leu), SP-C33, SP-C30 and SP-C33Leu; surfactant protein A (SP-A) and variants thereof; and surfactant protein D (SP-D) and variants thereof; and Bri2-BRICHOS and variants thereof, including $Bri2_{113-231}$. Other preferred proteins according to the invention are nicastrin, neuroserpin, GFP, eGFP, and the 1a AA, 1b AA, 0 AAAA, 1a LL, 1b LL and 0 LLLL proteins.

In certain preferred embodiments of the invention, the fusion protein is selected from the group consisting of SEQ ID NOS 56, 60, 64, 66, 70-75, 82, 84, 87, 90 and 93; and proteins having at least 80%, preferably at least 90%, more preferably at least 95% identity, to any of these proteins.

According to one aspect, the present invention provides a composition comprising an aqueous solution of a protein according to the invention. In a preferred embodiment, the composition is consisting of an aqueous solution of a protein according to the invention. It is preferred that the protein is a fusion protein according to the invention. It is preferred that the pH of the composition is 7.2 or lower, such as 5.5-7.2.

According to another aspect, the present invention provides an isolated nucleic acid, preferably a cDNA, encoding a protein according to the invention. In a preferred embodiment, the isolated nucleic acid is selected from the group consisting of SEQ ID NOS 58, 62, 65, 68, 76-81, 83, 85, 89, 91 and 95.

According to one aspect, the present invention provides a novel use of at least one moiety of 100-160 amino acid residues having at least 70% identity with SEQ ID NO: 1, wherein the amino acid residue corresponding to position 40 in SEQ ID NO: 1 is selected from the group consisting of Lys, Arg and His; and wherein the amino acid residue corresponding to position 65 in SEQ ID NO: 1 is selected from the group consisting of Asp and Glu, as a moiety in a fusion protein for enhancing the solubility of another moiety in the fusion protein, which is a desired protein or polypeptide as set out herein. Preferred features of the inventive solubility-enhancing moiety are presented hereinabove.

In one preferred embodiment, the solubility-enhancing moiety is used for production of the desired protein or polypeptide. In another preferred embodiment, the solubility-enhancing moiety is used for studying or characterizing the desired protein or polypeptide.

An advantageous use of the inventive moiety is as a solubility-enhancing moiety in a fusion protein which is subjected to a pH of 7.2 or lower, such as 5.5-7.2. This specific variant of the N-terminal (NT) fragment of a spider silk protein is present as a soluble monomer regardless of the pH of the surrounding aqueous medium. Wildtype NT forms dimers at a pH interval of 5.5-7.2 which increases the risk of undesirable aggregation of the fusion proteins. This is a useful pH interval for the functionality and stability of certain desirable proteins and polypeptide. It is also a useful pH interval for certain purification protocols, e.g. when using ion exchange, such as cation or anion exchange, or immobilized metal ion affinity chromatography (IMAC) as a purification principle. It is also a useful pH interval for certain expression hosts, e.g. yeasts.

According to another aspect, the present invention provides a method of producing a desired protein or polypeptide. The first step involves expressing in a suitable host a fusion protein according to the invention, comprising the desired protein or polypeptide. The solubility-enhancing moiety has at least 70% identity, such as 75%, 80%, 85%, 90%, 95% or even 100% identity with any one of the charge-reversed NT proteins as set out in SEQ ID NO: 1-7 or the charge-reversed variants of SEQ ID NO: 96, preferably SEQ ID NO: 1-2 or the charge-reversed variants of SEQ ID NO: 96. As set out herein, the amino acid residue corresponding to position 40 in SEQ ID NO: 1 is selected from the group consisting of Lys, Arg and His; and the amino acid residue corresponding to position 65 in SEQ ID NO: 1 is selected from the group consisting of Asp and Glu. In an alternative embodiment, the solubility-enhancing moiety has at least 70% identity, such as 75%, 80%, 85%, 90%, 95% or even 100% identity with the wildtype NT protein as set out in SEQ ID NO: 9 or 96. For avoidance of doubt, this implies that the method is also applicable for solubility-enhancing moieties which are not charge-reversed NT proteins, e.g. not as set out in SEQ ID NO: 1-7.

Suitable expression hosts are well known to a person skilled in the art and include e.g. bacteria and eukaryotic cells, such as yeast, insect cell lines and mammalian cell lines. Typically, this step involves expression of a nucleic acid molecule which encodes the fusion protein in *E. coli*.

The second method step involves obtaining a mixture containing the fusion protein, and optionally isolating the fusion protein. The mixture may for instance be obtained by lysing or mechanically disrupting the host cells. The mixture may also be obtained by collecting the cell culture medium, if the fusion protein is secreted by the host cell. The thus obtained protein can be isolated using standard procedures. If desired, this mixture can be subjected to centrifugation, and the appropriate fraction (precipitate or supernatant) be collected. The mixture containing the fusion protein can also be subjected to gel filtration, chromatography, e.g. ion exchange chromatography, such as cation or anion exchange chromatography, dialysis, phase separation or filtration to cause separation.

In a preferred embodiment, the obtained mixture comprises the fusion protein dissolved in a liquid medium, typically a salt buffer or cell culture medium. This specific variant of the N-terminal (NT) fragment of a spider silk protein is present as a soluble monomer regardless of the pH of the surrounding aqueous medium. Wildtype NT forms dimers at a pH interval of 5.5-7.2 which increases the risk of undesirable aggregation of the fusion proteins. This is a useful pH interval for the functionality and stability of certain desirable proteins and polypeptide, e.g. amyloid-forming or aggregation-prone proteins/polypeptides. It is also a useful pH interval for certain expression hosts, e.g. yeasts. It is also a useful pH interval for certain purification protocols, e.g. when using ion exchange, such as cation or anion exchange, or immobilized metal ion affinity chromatography (IMAC) as a purification principle. In a preferred embodiment, this step further involves purification of the fusion protein on an ion exchange medium, such as a cation or anion exchange medium. In one preferred embodiment, this step further involves purification of the fusion protein on an IMAC medium, preferably with elution using low pH (below the pKa of His, typically a pH of approximately 6).

Thus, the fusion protein is typically obtained as a solution in a liquid medium. By the terms "soluble" and "in solution" is meant that the fusion protein is not visibly aggregated and does not precipitate from the solvent at 60 000×g. The liquid medium can be any suitable medium, such as an aqueous medium, preferably a physiological medium, typically a buffered aqueous medium, such as a 10-50 mM Tris-HCl buffer or phosphate buffer.

It has been advantageously been found that the presence of the solubility-enhancing moiety according to the invention improves the stability of the desired protein/polypeptide and prevents moiety dimer formation under these conditions. This can be advantageous when immediate polymerisation may be undesirable, e.g. during protein purification or in preparation of large batches. In particular, this is advantageous for methods according to the invention which are comprising at least one step involves subjecting the fusion protein to a pH of 7.2 or lower, such as 5.5.-7.2. As set out above, this specific variant of the N-terminal (NT) fragment of a spider silk protein is present as a soluble monomer regardless of the pH of the surrounding aqueous medium. Wildtype NT forms dimers at a pH interval of 5.5-7.2 which increases the risk of undesirable aggregation of the fusion proteins. This is a useful pH interval for the functionality and stability of certain desirable proteins and polypeptide, e.g. amyloid-forming or aggregation-prone proteins/polypeptides. It is also a useful pH interval for certain expression hosts, e.g. yeasts.

In a preferred embodiment, the fusion protein is isolated from the mixture without any separation step involving gel filtration, chromatography or any other solid phase adsorption-based separation. In one preferred embodiment, the fusion protein is isolated from the mixture by precipitation of the fusion protein, followed by suspending the precipitated fusion protein in an aqueous solvent, wherein the fusion protein is soluble in the aqueous solvent.

The precipitation of the fusion protein may be performed by any suitable technique to decrease the solubility of the fusion protein in the solvent, including changes in ionic strength and addition of miscible organic solvents. It is preferred that the precipitation of the fusion protein is achieved by salting out at high salt concentration, i.e. subjecting the fusion protein to sufficiently high salt concentration to render the fusion protein insoluble. By way of example, a NaCl concentration of 0.5 M or higher, such as 1 M or higher, is typically sufficient to precipitate the fusion protein. The precipitate containing the fusion protein is collected e.g. by filtration or centrifugation, and the filtrate or supernatant is discarded. Optionally, lipopolysaccharides and other pyrogens are actively removed at this stage. If desired, the isolated precipitated fusion protein can be suspended and dissolved in a suitable solvent. Preferably, the precipitated fusion protein is suspended in an aqueous solvent, wherein the fusion protein is soluble.

In certain embodiments, the method is further comprising the step of cleaving the fusion protein to release the desired protein or polypeptide from the residual solubility-enhancing moiety or fragments thereof as cleavage products; and optionally isolating the desired protein or polypeptide. If desired, linker peptides may be removed by cleavage in this step. In these embodiments, the fusion protein is comprising at least one cleavage site arranged between at least one desired protein or polypeptide moiety and at least one solubility-enhancing moiety. In a typical fusion protein, this implies the presence of a single cleavage site between the solubility-enhancing moiety or moieties and the desired protein or polypeptide. Cleavage may be achieved using standard procedures, for instance cleavage by cyanogen bromide (CNBr) after Met residues, cleavage by hydroxylamine between Asn and Gly residues, cleavage by protease 3C between Gln and Gly residues at -XLETLFQGX- sites, and at various other protease sites that are well known to the person skilled in the art.

The thus obtained desired protein or polypeptide can be isolated using standard procedures. If desired, this mixture can also be subjected to centrifugation, and the appropriate fraction (precipitate or supernatant) be collected. The mixture containing the desired protein or polypeptide can also be subjected to gel filtration, chromatography, dialysis, phase separation or filtration to cause separation. Optionally, lipopolysaccharides and other pyrogens are actively removed at this stage. If desired, linker peptides may be removed by cleavage in this step.

In a preferred embodiment, the desired protein or polypeptide is isolated from the mixture without any separation step involving gel filtration, chromatography or any other solid phase adsorption-based separation. In one preferred embodiment, the desired protein or polypeptide is isolated from the mixture by extraction in an organic solvent, i.e. extracting the desired protein or polypeptide by suspending the cleavage products in an organic solvent wherein the desired protein or polypeptide is soluble and wherein the residual solubility-enhancing moiety according to the invention or fragments thereof is/are not soluble.

The organic solvents that are used according to the invention are carbon-containing solvents and may exhibit a varying degree of polarity. Although termed "solvents", it shall be understood that these organic solvents are utilized for balancing and shifting the solubility of the fusion protein and/or the desired protein or polypeptide and/or the residual solubility-enhancing moiety or fragments thereof during the manufacturing method. The proteins or polypeptides may very well be dissolved in an organic solvent at a certain organic solvent concentration interval, but falls out and forms a precipitate when the organic solvent concentration is increased or decreased. For instance, the residual solubility-enhancing moiety or fragments thereof can be dissolved in a 50/50 (vol/vol) mixture of an organic solvent, e.g. a lower alkyl alcohol, and water, but falls out and forms a precipitate in 90/10 or 10/90 (vol/vol) mixtures. When subjected to non-precipitating conditions, e.g. a 50/50 or a 0/100 mixture, the proteins or polypeptides return to the non-precipitated, dissolved state. The skilled person is well aware that other factors may have an impact on the limiting organic solvent(s) concentration for precipitation of the proteins or polypeptides, such as temperature, pH, ion strength and type of organic solvent(s). The limiting concentration for precipitation of the proteins or polypeptides under given conditions is well known or can easily be determined by a skilled person in the field.

Without being limited thereto, the organic solvents according to the invention can be selected from the group consisting of pentane, hexane, cyclohexane, 1,4-dioxane, N,N-dimethylformamide, N,N-dimethylacetamide, chloroform, ethyl acetate, acetamide, diethyl ether, tetrahydrofurane, acetonitrile, methyl ethyl ketone, acetone, lower alkyl alcohols, e.g. methanol, ethanol, propanol, isopropanol and butanol, or any mixture of the mentioned solvents. It is preferable that the organic solvents according to the invention are water-soluble. A preferred group of organic solvents is the lower alkyl alcohols. The term lower alkyl alcohol includes primary, secondary and tertiary alkyl alcohols having from one to six carbon atoms, i.e. $C_{1-6}$ alkyl alcohols. Specific examples of lower alkyl alcohols include methanol, ethanol, denatured spirit, n-propanol, isopropanol, n-butanol, isobutanol, and t-butanol. Preferred lower alkyl alcohols are methanol, ethanol, isopropanol and isobutanol, in particular ethanol, due to price, availability and easy handling.

In one preferred embodiment, the method is further comprising, prior to the extraction step, the step of precipitation of the cleavage products. The precipitation of the cleavage products may be performed by any suitable technique to decrease the solubility of the desired protein or polypeptide in the solvent, including changes in ionic strength and addition of miscible organic solvents. It is preferred that the precipitation of the cleavage products is achieved by salting out at high salt concentration, i.e. subjecting the cleavage products to sufficiently high salt concentration to render the desired protein or polypeptide insoluble. By way of example, a NaCl concentration of 0.5 M or higher, such as 1 M or higher, is typically sufficient to precipitate the desired protein or polypeptide. The precipitate containing the desired protein or polypeptide is collected e.g. by filtration or centrifugation, and the filtrate or supernatant is discarded. Optionally, lipopolysaccharides and other pyrogens are actively removed at this stage. If desired, the isolated precipitated desired protein or polypeptide can be suspended and dissolved in a suitable solvent.

A preferred method of producing a desired protein or polypeptide is thus comprising the following steps:

a) expressing in a suitable host a fusion protein according to the invention, comprising the desired protein or polypeptide; and b) obtaining a mixture containing the fusion protein, and
   b1) isolating the fusion protein, comprising the following steps:
      b1a) precipitation of the fusion protein, preferably by salting out at high salt concentration; and
      b1b) suspending the precipitated fusion protein in an aqueous solvent, wherein the fusion protein is soluble in the aqueous solvent;

c) cleaving the fusion protein to release the desired protein or polypeptide from the residual solubility-enhancing moiety or fragments thereof as cleavage products; and
   c1) isolating the desired protein or polypeptide, comprising the following steps:
      c1a) precipitation of the cleavage products; preferably by salting out at high salt concentration;
      c1b) extracting the desired protein or polypeptide by suspending the precipitated cleavage products in an organic solvent, preferably comprising a lower alkyl alcohol, such as methanol, ethanol or isopropanol; wherein the desired protein or polypeptide is soluble in the organic solvent; and wherein the residual solubility-enhancing moiety or fragments thereof is/are not soluble in the organic solvent.

The present invention will in the following be further illustrated by the following non-limiting examples.

EXAMPLES

Example 1—Expression of NT and Charge-Reversed NT Mutants

Constructs with $NT_{wt}$ (SEQ ID NO: 12, encoding SEQ ID NO: 11) and $NT_{D40K/K65D}$ (SEQ ID NO: 8, encoding SEQ ID NO: 2) were cloned into pT7 expression vectors and transformed into chemically competent *E. coli* BL21 (DE3) cells. Plasmid-containing cells were inoculated to 10 mL Luria-Bertani (LB) medium with 70 mg/L kanamycin and grown at 37° C. and 180 rpm over night. 5 mL over-night culture was inoculated to 500 mL LB medium (1/100) with kanamycin and cells were further grown at 30° C. to $OD_{600}$ of ~1. The cells were induced by addition of Isopropyl β-D-1-thiogalactopyranoside (IPTG) to a final concentration of 0.5 mM and expression was performed at 20° C. over night. The day after, cells were harvested by centrifugation, resuspended in 20 mM Tris-HCl, pH 8 to 30 mL and stored at −20° C. for at least 24 hours.

Example 2—Biophysical Properties of $NT_{D40K/K65D}$ Compared to $NT_{wt}$

The NT dimerization process is highly dependent on intermolecular electrostatic interactions between the residues D40 and K65, playing a key role in the initial association of monomers. In this study, we designed and evaluated a double mutant ($NT_{D40K/K65D}$; SEQ ID NO: 2) where these residues were swapped compared to the wildtype NT ($NT_{wt}$; SEQ ID NO: 11), while preserving the net charge of the domain. Important biophysical properties were evaluated to determine the applicability of the mutant as a solubility enhancing fusion partner.

(A) Tryptophan Fluorescence Measurement

Fluorescence emission spectra for $NT_{D40K/K65D}$ (SEQ ID NO: 2) and $NT_{wt}$ (SEQ ID NO: 11), respectively, were measured on a spectrofluorometer (Tecan Safire 2) using Costar® black polystyrene assay plates with 96 flat bottom wells. The proteins were diluted to a concentration of 5 μM in 20 mM HEPES/20 mM MES adjusted to pH 5.6-8.0 in steps of 0.4 pH units. After exciting the samples at 280 nm (5 nm bandwidth), emission spectra were recorded in 1 nm steps between 300-400 nm (10 nm bandwidth). The tryptophan fluorescence ratio was calculated from the intensities at 339 nm and 351 nm and plotted as a function of pH. The data obtained for $NT_{wt}$, was fitted to a two-state binding model due to the sigmoidal behavior of the monomer-dimer equilibrium.

The pH-dependent monomer-dimer equilibrium of NT can be monitored through the fluorescence shift of a single tryptophan (Trp) residue that becomes more exposed in the dimer. FIG. 2 is a graph illustrating the monomer-dimer equilibrium measured with Trp fluorescence. Trp fluorescence spectra between 300 and 400 nm were measured in 20 mM HEPES/20 mM MES buffer and the ratio at 339/351 nm (wavelengths corresponding to monomer and dimer conformations, respectively) was calculated and plotted as a function of pH for $NT_{wt}$ (dotted line) and $NT_{D40K/K65D}$ (filled line). The ratio of fluorescence at 339 and 351 nm as a function of pH gives a sigmoidal plot for $NT_{wt}$ with a pKa of dimerization at pH 6.5. This fluorescence shift was not observed for the mutant $NT_{D40K/K65D}$ and a ratio corresponding to a monomer was measured over the whole pH range (FIG. 2).

(8) [$^{15}$N, $^{1}$H]-HSQC NMR Measurements

Cells expressing the NT variants $NT_{D40K/K65D}$ (SEQ ID NO: 2) and $NT_{wt}$ (SEQ ID NO: 11) were cultured over-night and further inoculated 1/100 to 500 mL minimal medium M9 containing $^{15}$N-labelled ammonium chloride and 70 mg/L kanamycin. The cells were grown over night at 22° C. to an $OD_{600}$ of 1.4. Protein was expressed and purified as previously described.

[$^{15}$N, $^{1}$H]-HSQC HSQC NMR spectra were acquired at 25° C. on a Varian Unity Inova 600-MHz NMR spectrometer equipped with an HCN cold probe. NMR samples of $^{15}$N-labelled protein were prepared in either 20 mM sodium phosphate, 20 mM NaCl, pH 5.5 or 20 mM sodium phosphate, 300 mM NaCl, pH 7.2 buffers and 2D [$^{15}$N, $^{1}$H]-HSQC NMR spectra were recorded. The spectra were processed and analyzed using Bruker Topspin 3.1 software.

HSQC NMR was measured at pH 7.2 and 5.5 where $NT_{wt}$ is a monomer or dimer, respectively, showing large chemical shift differences. Overlays of $^{15}$N-$^{1}$H HSQC NMR spectra of $NT_{wt}$ and $NT_{D40K/K65D}$ were produced at pH 5.5 and at pH 7.2 (not shown). FIG. 3 shows averaged backbone amide 1H and 15N chemical shift differences $\Delta\delta_{av}=\sqrt{(0.1\Delta\delta_N)^2+(\Delta\delta_H)^2}$ between $NT_{wt}$ and $NT_{D40K/K65D}$ at pH 5.5 (lower panel) and pH 7.2 (upper panel). The spectra obtained from $NT_{D40K/K65D}$ were similar at both pH values and corresponding to the spectra for monomeric $NT_{wt}$ at pH 7.2.

(C) Urea-Induced Denaturation as a Measure of Stability $NT_{wt}$ (SEQ ID NO: 11) and $NT_{D40K/K65D}$ (SEQ ID NO: 2) proteins were diluted to 5 μM in 20 mM HEPES/20 mM MES supplemented with 0-7 M urea in 0.5 M steps. The stability of the proteins at each concentration of urea was monitored with Trp fluorescence at constant pH values ranging from 5.0 to 7.5 with 0.5 unit steps. For each measured pH, the fluorescence ratio was plotted against the urea concentration and fitted to a two-state unfolding model in order to determine the transition points. The data for $NT_{wt}$ (dotted line) and $NT_{D40K/K65D}$ (filled line) are presented as transition points between native and denatured states ($[den]^{50\%}$) as a function of pH in FIG. 4.

Referring to FIG. 4, $NT_{wt}$ is significantly more stable in the dimer conformation at low pH. In contrast, $NT_{D40K/K65D}$ exhibits an increased overall stability in the entire pH interval, similar to the $NT_{wt}$ dimer and independent of changes in pH.

(D) Temperature Scans as a Measure of Stability

Temperature scans were performed and analyzed with circular dichroism (CD). Experiments were performed on a 410-model circular CD spectrometer (Aviv biomedical Inc., Lakewood, N.J., USA) using 300 μL cuvettes with a 1 mm path length. For all measurements, the $NT_{wt}$ (SEQ ID NO: 11) and $NT_{D40K/K65D}$ (SEQ ID NO: 2) proteins were diluted to 10 μM in 5 mM phosphate buffer at pH 5.5 or pH 8.0. CD spectra were recorded from 260 to 185 nm at 25° C., after heating to 95° C. and again at 25° C. after the samples were allowed to cool down. For each temperature, the data is shown as an average of 4 scans. Temperature scans were measured at 222 nm by recording 1° C. steps in the temperature interval 25-95° C., and data were fitted to a two-state unfolding model.

FIG. 5 shows thermal stability of $NT_{wt}$ and $NT_{D40K/K65D}$ measured with CD spectroscopy. The CD signal in mdegrees was measured at 222 nm at pH 5.5 and pH 8.0, plotted as a function of temperature (° C.) and fitted to a two-state unfolding model to obtain the melting temperatures ($T_m$) at the equilibration points. The highest melting temperatures were determined for $NT_{D40K/K65D}$ at pH 8.0 and pH 5.5, respectively. Considerably lower melting temperatures were determined for $NT_{wt}$ monomer at pH 8.0 and the $NT_{wt}$ dimer at pH 5.5.

FIG. 6 shows refolding capacity of $NT_{wt}$ and $NT_{D40K/K65D}$ measured with CD spectroscopy. The molar ellipticity was scanned between 185 nm and 260 nm at 25° C., 95° C., and again at 25° C. after cooling for $NT_{wt}$ at (A) pH 8.0 and (B) pH 5.5 and for $NT_{D40K/K65D}$ at (C) pH 8.0 and (D) pH 5.5. The data is presented as a smoothed average of four measurements. CD spectra monitored before and after thermal denaturation shows that although $NT_{wt}$ refolds into an alpha-helical structure, there is a reduced ellipticity after refolding at pH 8 (FIG. 6A), which is even more evident at pH 5.5 (FIG. 6B). An increased refolding capacity was observed for $NT_{D40K/K65D}$, showing close to identical alpha-helical spectra before temperature induced unfolding and after refolding at pH 8 (FIG. 6C) and pH 5.5 (FIG. 6D).

Example 3—Expression of Fusion Proteins

The fusion protein constructs with the target peptides SP-C33Leu (SEQ ID NO: 58-59, encoding SEQ ID NO: 56-57) and KL4 (SEQ ID NO: 62-63, encoding SEQ ID NO: 60-61) in fusion with $NT_{D40K/K65D}$ and $NT_{wt}$, respectively, were cloned into pT7 expression vectors and transformed into chemically competent *E. coli* BL21 (DE3) cells. Fusion protein constructs with the same target peptides and proteins in fusion with PGB1 or Trx were subjected to the same procedure.

Plasmid-containing cells were inoculated to 10 mL LB medium with 70 mg/L kanamycin and grown at 37° C. and 180 rpm over night. 5 mL over-night culture was inoculated to 500 mL LB medium (1/100) with kanamycin and cells were further grown at 30° C. to $OD_{600}$ of ~1. The cells were induced by addition of IPTG to a final concentration of 0.5 mM and expression was performed at 20° C. over night. The day after, cells were harvested by centrifugation, resuspended in 20 mM Tris-HCl, pH 8 to 30 mL and stored at −20° C. for at least 24 hours.

Example 4—Purification of Fusion Proteins for Comparison of Yields

The ability of the NT variants $NT_{wt}$ and $NT_{D40K/K65D}$ to mediate solubility to aggregation-prone fusion partners in comparison to the highly soluble PGB1 domain was tested. Trx was also evaluated in fusion with SP-C33Leu but was later excluded due to its poor performance.

Fusion proteins obtained in Example 3 were solubilized by sonication in loading buffer (20 mM Tris-HCl, pH 8) at 80% amplitude, 1 s on and 1 s off for a total of 3 min. The soluble and insoluble fractions were separated by centrifugation at 27 000×g, 4° C. for 30 min. The clear lysate was loaded to an IMAC column, previously packed with Ni-Sepharose (GE Healthcare) and equilibrated with loading buffer. Bound protein was washed with 20 mM Tris-HCl, 5 mM imidazole, pH 8 and eluted with 20 mM Tris-HCl, 300 mM imidazole, pH 8 in 1 mL fractions. The absorbance at 280 nm was measured for each fraction, and protein-rich fractions were pooled. Imidazole was removed by overnight dialysis at 4° C. and in 5 L loading buffer, using a Spectra/Por® dialysis membrane with a 6-8 kDa molecular weight cut-off. The purity of the protein in each step was determined by SDS-PAGE using a 15 acrylamide gel stained with Coomassie Brilliant Blue.

(A) SP-C33Leu Fusion Proteins

Figure 7:
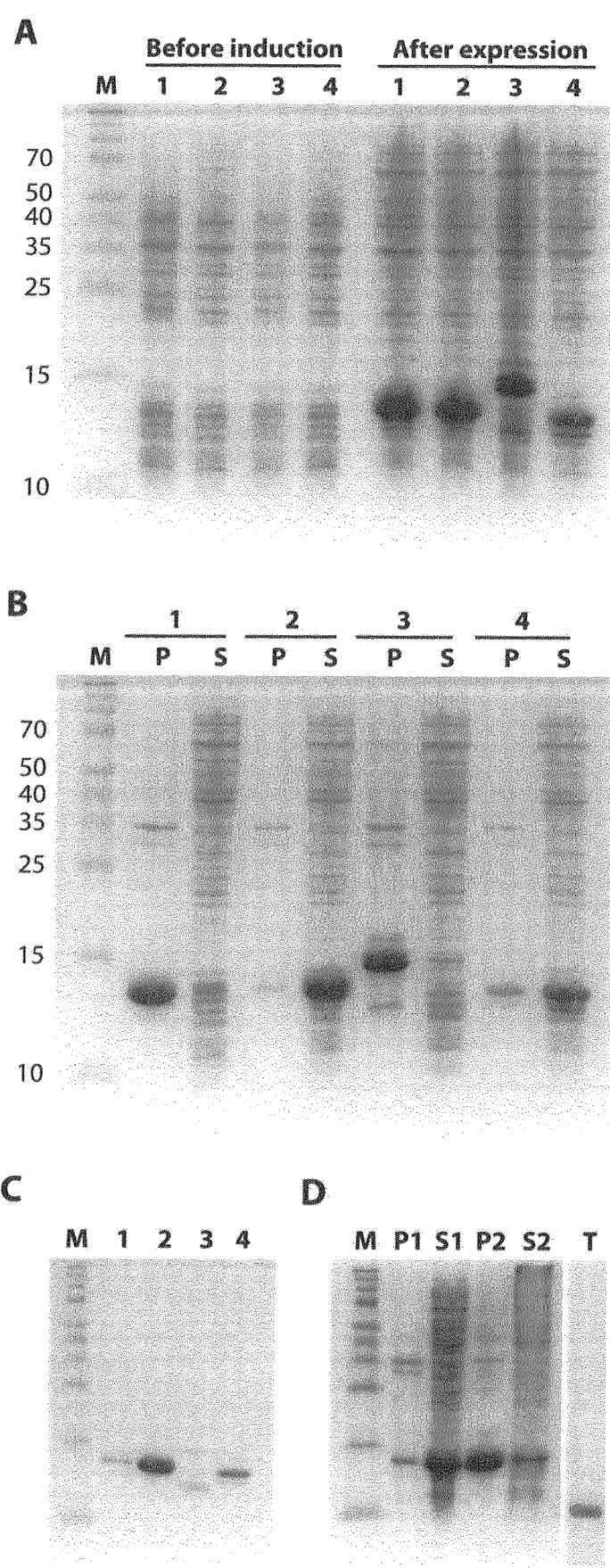

FIG. 7 shows an SDS-PAGE evaluation of SP-C33Leu fusion proteins. The peptide was fused C-terminally of $NT_{wt}$ (lane 1), $NT_{D40K/K65D}$ (lane 2), Trx (lane 3) or PGB1 (lane 4). Lane M denotes the size marker and the molecular weights are indicated to the left. Panel A shows an expression analysis before induction and after over-night expression at 20° C. in B121 E. coli cells. Panel B shows a solubility analysis after 3 min of sonication in 20 mM Tris-HCl, pH 8, followed by separation of soluble (S) and insoluble (P) fractions. Panel C shows fusion proteins after comparative Ni-Sepharose purification.

(B) KL4 Fusion Proteins

FIG. 8 shows an SDS-PAGE evaluation of KL4 fusion proteins. The peptide was fused C-terminally of $NT_{wt}$ (lane 1), $NT_{D40K/K65D}$ (lane 2) or PGB1 (lane 3). Lane M denotes the size marker and the molecular weights are indicated to the left. Panel A shows an expression analysis before induction and after over-night expression at 20° C. in B121 E. coli cells. Panel B shows a solubility analysis after 3 min of sonication in 20 mM Tris-HCl, pH 8, followed by separation of soluble (S) and insoluble (P) fractions. Panel C shows fusion proteins after comparative Ni-Sepharose purification.

In summary, the NT variants $NT_{wt}$ and $NT_{D40K/K65D}$ were abundantly expressed at similar levels in fusion with SP-C33Leu (FIG. 7A) and KL4 (FIG. 8A), and at higher levels compared to PGB1 and Trx. All proteins and peptides appeared stable in fusion with the NT variants $NT_{wt}$ and $NT_{D40K/K65D}$, but Trx-SP-C33Leu showed signs of degradation during expression.

Both $NT_{D40K/K65D}$ and PGB1 were able to mediate high solubility to their target proteins/peptides and with some minor differences, the most part was found in the soluble fractions (FIG. 7-8B). $NT_{wt}$ showed ~50% soluble protein in fusion with KL4 (FIG. 8B). The most remarkable difference between the NT variants was observed in fusion with SP-C33Leu, resulting in mainly insoluble protein for $NT_{wt}$ and fully soluble protein for $NT_{D40K/K65D}$ (FIG. 7B).

Purification of $NT_{D40K/K65D}$ fusion proteins on Ni-sepharose yielded 284 and 428 mg/L culture for SP-C33Leu and KL4, respectively (FIG. 7-8C). This corresponds to between 2 and 8-fold higher amounts compared to protein in fusion with PGB1, mainly due to the higher expression levels (Table 9). The yields for $NT_{wt}$ were intermediate, around 1.3 to 4-fold higher compared to PGB1 fusions proteins. Trx in fusion with SP-C33Leu gave the lowest yield and the fusion protein continued to degrade during purification (FIG. 7C).

TABLE 9

Calculated yields after Ni-Sepharose purification of fusion proteins

| Target protein/peptide | Purified fusion protein (mg/L culture) for solubility-enhancing moiety | | | |
|---|---|---|---|---|
| | $NT_{wt}$ | $NT_{D40K/K65D}$ | PGB1 | Trx |
| SP-C33Leu | 93 | 284 | 56 | 43 |
| KL4 | 212 | 428 | 56 | — |

Example 5—Purification of SP-C33Leu and KL4 Peptides

Cells expressing fusion proteins obtained in Example 3 were lysed by sonication at 80% amplitude for 1.5 min, 1 s on and 1 s off, 3 min total time. Only during full-scale purification by precipitation, the sonication procedure was repeated after standing on ice for 5 min and the sample was centrifuged at 50 000×g for 30 min. Sodium chloride was added to the supernatant to a final concentration of 1.2 M and the centrifugation was repeated. The pellet from the centrifugation was dissolved in 20 mM Tris-HCl, pH 8 and briefly sonicated at 60% amplitude for 1.5 min, 1 s on and 1 s off, 3 minutes in order to fully re-dissolve the fusion protein. CNBr cleavage was performed by adding 1.7 mL 2 M HCl to 30 mL dissolved solution, followed by 1.7 mL 1 M CNBr. The cleavage reaction was performed over night at room temperature. The next day, 800 mM sodium chloride was added to the cleavage reaction in a second precipitation step, followed by centrifugation at 20 000×g for 30 min. The supernatant was removed and the pellet was dried at 37° C. and suspended in 99.9% ethanol. Insoluble material was removed by centrifugation at 20 000×g for 30 min.

(A) SP-C33Leu Peptide (SEQ ID NO: 44)

SP-C33Leu was expressed as a $NT_{D40K/K65D}$ fusion protein and produced in a process independent of chromatographic steps. FIG. 7D shows an SDS-PAGE evaluation of purification of the SP-C33Leu peptide from $NT_{D40K/K65D}$-SP-C33Leu using a NaCl precipitation/ethanol extraction protocol and CNBr bromide cleavage for removal of the fusion tag. P1, S1, P2, S2 and T denote insoluble fraction, soluble fraction, pellet after first precipitation, supernatant after first precipitation, and purified target peptide, respectively.

First, the sonicated cell lysate was purified in one simple step using 1.2 M sodium chloride to precipitate the majority of the fusion protein and remove most contaminants (FIG. 7D). The fusion protein was designed with a methionine residue located just N-terminally of the peptide, allowing for cleavage with cyanogen bromide (CNBr).

Subsequent to CNBr cleavage under acidic conditions, a second precipitation was performed using 0.8 M sodium chloride. SP-C33Leu and KL4 are both soluble in organic solvents, e.g. ethanol, methanol or isopropanol, and surprisingly all the NT-fragments generated by CNBr remain insoluble in these solvents. Accordingly, the precipitated pellet was further purified by suspension in 99.9% ethanol followed by centrifugation to isolate 20-30 mg/L culture of highly pure SP-C33Leu peptide in the soluble ethanol fraction (FIG. 7D).

(B) KL4 Peptide (SEQ ID NO: 46)

The procedure set out above for purification of the SP-C33Leu peptide from $NT_{D40K/K65D}$-SP-C33Leu was reproducible also for purification of the KL4 peptide from $NT_{D40K/K65D}$-KL4. FIG. 8D shows an SDS-PAGE evaluation of purification of the KL4 peptide from $NT_{D40K/K65D}$-KL4 using a NaCl precipitation/ethanol extraction protocol and CNBr bromide cleavage for removal of the fusion tag. P1, S1, P2, S2 and T denote insoluble fraction, soluble fraction, pellet after first precipitation, supernatant after first precipitation, and purified target peptide, respectively.

Ethanol extraction yielded 10-15 mg/L culture of pure KL4 peptide (FIG. 8D).

Example 6—ESI-MS Characterization of SP-C33Leu

Further characterization of the purified SP-C33Leu (SEQ ID NO: 44) obtained in Example 5 with ESI-MS showed that the recombinantly produced peptide dissolved in ethanol has the correct covalent structure.

ESI-MS spectra of SP-C33Leu obtained in Example 5 are shown in FIG. 9. The spectrum shown in panel A shows mainly monomeric SP-C33Leu with 3 or 4 charges and one or two sodium adducts, and a minor fraction of dimers with 7 charges. A small amount of a contaminant (approximately 4314.8 Da corresponding to the peak at 1079 m/z) could also be observed. Panel B shows a MS/MS spectrum of the m/z 1199.2 peak in panel A.

Example 7—Effect of rSP-C33Leu on Tidal Volumes and Lung Gas Volumes

The effect of SP-C and derivatives thereof on tidal volumes and lung gas volumes can be evaluated using an animal model with positive end-expiratory pressure (PEEP) (Almlen, A et al., Neonatology 92, 194-200 (2007)).

Immature newborn rabbits (gestational age 27 days) were treated at birth with 200 mg/kg of 2% rSP-C33Leu (SEQ ID NO: 44) in dipalmitoylphosphatidylcholine (DPPC)/palmitoyloleoyl-phosphatidylglycerol (POPG) 68:31 (w/w) at a concentration of 80 mg/ml. Animals receiving the same dose of Curosurf® served as positive and non-treated littermates as negative controls. Animals were ventilated with a standard pressure sequence for 35/0 (peak-insufflation pressure [cm $H_2O$]/positive end-expiration pressure (PEEP) [cm $H_2O$]) for 1 min, 23/3 for 15 min, 18/3 for 5 min, 13/3 for 5 min and 23/3 for 5 min. Finally, the lungs were ventilated for additional 5 min with nitrogen at 23/3 cm $H_2O$ and then excised for gas volume measurements. Both tidal volumes and lung gas volumes are given as median values.

FIG. 10 illustrates the effects of rSP-C33Leu on tidal volumes. Tidal volumes during 30 min of ventilation are shown for immature newborn rabbits treated at birth with 200 mg/kg of 2% rSP-C33Leu in DPPC:POPG (68:31 w/w) at a concentration of 80 mg/mL and compared to animals receiving the same dose of Curosurf, DPPC:POPG only (negative control) and non-treated animals. The tidal volumes are markedly increased for animals treated with 2% rSP-C33Leu in DPPC:POPG (68:31), compared to untreated negative controls and controls treated with DPPC:POPG (68:31), and approach those obtained after treatment with Curosurf®.

FIG. 11 illustrates the effects of rSP-C33Leu on lung gas volumes. Lung gas volumes are shown for immature newborn rabbits treated at birth with 200 mg/kg of 2% rSP-C33Leu in DPPC:POPG (68:31 w/w) at a concentration of 80 mg/mL and compared to animals receiving the same dose of Curosurf®, DPPC:POPG only (negative control) and non-treated animals. The lung gas volumes of animals treated with 2% rSP-C33Leu in DPPC:POPG (68:31) and Curosurf are equal, and significantly higher than those for animals treated with DPPC:POPG (68:31). Similar results were obtained using a synthetic SP-C33Leu peptide in the same animal model (data not shown).

Example 8—Expression of β17 Polypeptide Using a $NT_{D40K/K65D}$ Fusion Protein

In order to investigate amyloid aggregation mechanisms broadly, researchers have designed 617 (SEQ ID NO: 27), a polypeptide that is very aggregation-prone and able to form amyloid-like fibrils in vitro. 617 is composed of 6 β-strands containing 7 amino acids each, separated by 5 short turns. The residues are disposed in a polar non-polar pattern. 617 has previously been expressed together with a myc-tag for immunodetection, and consequently, the peptide was not soluble and had to be purified from inclusion bodies. Such a purification process requires the use of denaturing conditions (8 M urea), is time consuming and yields an unstable protein. Moreover, studies of β17 fibril formation using Thioflavin T (ThT) as a reporter has been troubled with precocious aggregation.

Constructs with β17 polypeptide in fusion with $NT_{D40K/K65D}$ (SEQ ID NO: 65, encoding SEQ ID NO: 64) and PGB1 (control) were cloned and expressed in accordance with Example 3. FIG. 12 is an SDS-PAGE evaluation of β17 fusion proteins and resulting purified polypeptide. The 617 polypeptide was fused C-terminally of $NT_{D40K/K65D}$ (lane 1) or PGB1 (lane 2). Lane M denotes the size marker and the molecular weights are indicated to the left. Panel A shows an expression analysis before induction and after over-night expression at 20° C. in B121 E. coli cells. The $NT_{D40K/K65D}$-β17 fusion protein was expressed in E. coli at abundant levels exceeding those observed for 617 in fusion with PGB1. Panel B shows a solubility analysis after 2 min of sonication in 20 mM Tris-HCl, pH 8, followed by separation of soluble (S) and insoluble (P) fractions. After sonication of harvested cells for 2 min followed by centrifugation, both fusion proteins were predominantly found in the soluble fraction.

Panel C shows fusion proteins after comparative Ni-Sepharose purification. Purification on Ni-Sepharose yielded 228 and 92 mg/L culture for 617 in fusion with $NT_{D40K/K65D}$ and PGB1, respectively, and the amounts correlated to the intensities of the bands when analyzed with SDS-PAGE. The $NT_{D40K/K65D}$ solubility tag was removed by proteolysis of a thrombin recognition sequence situated N-terminally of 617 followed by a second Ni-Sepharose purification step to separate the tag from the target protein. Panel D shows purification of β17 (SEQ ID NO: 27) from $NT_{D40K/K65D}$-β17 using Ni-sepharose chromatography and thrombin for cleavage and removal of the fusion tag. The lanes represent the supernatant after sonication (S), flow-through (FT), purified fusion protein (F), cleavage with thrombin (CL) and purified β17 target protein (T). The yield of soluble protein was 7.8 mg/L culture when measured immediately after purification.

In conclusion, $NT_{D40K/K65D}$ as a solubility enhancing fusion tag for β17 enables an efficient purification process under non-denaturing conditions.

Example 9—Characterization of β17 Polypeptide (A) Gel Filtration

The hydrodynamic size of the β17 polypeptide (SEQ ID NO: 27) obtained in Example 8 was characterized using gel filtration. Gel filtration was performed on a 24 mL Superdex-200 column run at 0.3 mL/min. Samples were injected using a 200 uL loop and TBS, 5 mM EDTA, pH 8 with or without 150 mM NaCl as running buffer. The column was calibrated with apoferritin (443 kDa), alcohol dehydrogenase (150 kDa), BSA (66 kDa) and carbonic anhydrase (29 kDa), that eluted at 10.25, 12.54, 13.65 and 16.18 mL, respectively.

FIG. 13 shows gel filtration of soluble $NT_{D40K/K65D}$-β17 fusion protein in running buffer without salt (FIG. 13A) and in running buffer supplemented with 150 mM NaCl (FIG. 13B). Analysis was performed after storage of the protein at −20° C. for one week (filled line) or at 4° C. for several days (dotted line).

The $NT_{D40K/K65D}$ fusion protein remained highly soluble and migrated as a stable octamer after storage at −20° C. for one week or at 4° C. for several days when analyzed with gel filtration in the absence of salt (FIG. 13A). Similar results were obtained in the presence of 154 mM NaCl and 1 mM EDTA, but under these conditions the protein migrated as a stable dimer (FIG. 13B).

(B) ThT Assay

Aggregation kinetics were monitored using ThT fluorescence based on the enhanced quantum yield for ThT fluorescence as it binds to amyloid fibrils. Experiments were performed with 80 μM $NT_{D40K/K65D}$-β17 in 20 mM sodium phosphate buffer pH 8.0, 0.2 mM EDTA, with 10 μM ThT in microplate wells (Microplate Corning 3881, 96-well, low binding, half area, Corning Incorporated Life Sciences, Acton, Mass.). ThT fluorescence was recorded under quiescent conditions at 37° C., using a Fluostar Omega or Optima plate reader (BMG Labtech, Offenburg, Germany) with a 440 nm excitation filter and a 480 nm emission filter.

Figure 14:
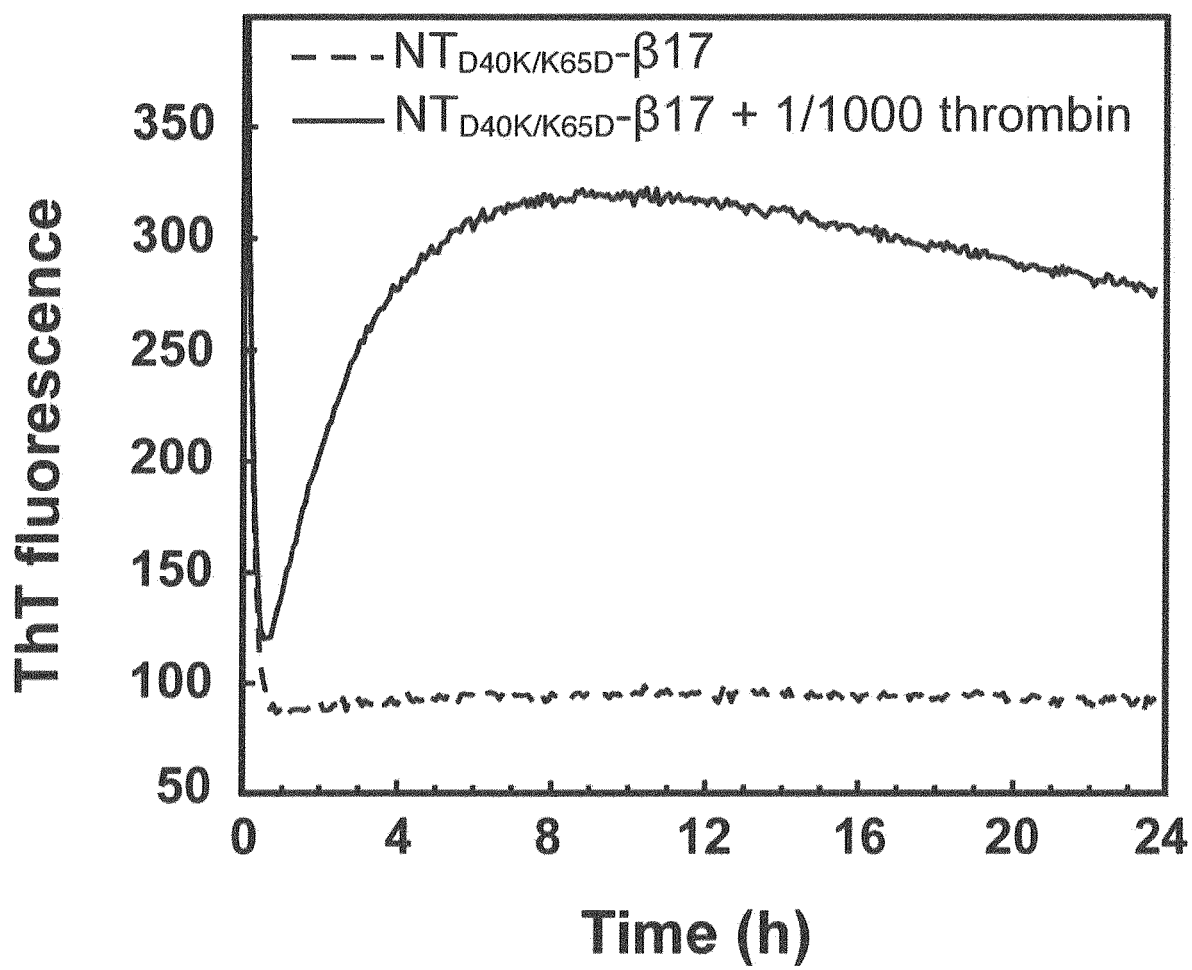
FIG. 14 is a graph of ThT fluorescence illustrating fibrillation of β17 after proteolysis of the fusion protein with thrombin.

FIG. 14 shows β17 fibrillation after proteolysis of the fusion protein with thrombin. ThT fluorescence of the fusion protein in the presence of thrombin (1000:1) shows fibrillation of β17 as indicated by the increased ThT fluorescence over time (solid line). No fibrillation was observed for the fusion protein in absence of thrombin (dotted line). When purified in the absence of a fusion tag, β17 does not remain in solution long enough to study the fibrillation with ThT assay (data not shown). Here, we showed that this is feasible by keeping the protein in solution when fused to $NT_{D40K/K65D}$, followed by proteolysis to release β17 at the start of the experiment.

Example 10—Expression of a Bri2 BRICHOS Domain Using a $NT_{D40K/K65D}$ Fusion Protein Bri2 is a TM glycoprotein composed of an N-terminal region followed by a TM domain, a linker region, a BRICHOS domain and a C-terminal region. The function is relatively unknown but the protein has been linked to Alzheimer's disease, Aβ precursor protein processing, Aβ homeostasis, apoptosis, tumor suppression and male reproduction. Mutations in Bri2 genes are associated with familial British dementia and familial Danish dementia, caused by the accumulation of amyloid fibrils in the brain. The situation is similar in Alzheimer's disease (AD) that is characterized by an accumulation of the amyloid beta peptide (Aβ), eventually forming brain plaques. The Bri2 BRICHOS domain is believed to act as an anti-amyloid chaperone, preventing amyloid formation and therefore is of interest as a promising therapeutic target.

The truncated BRICHOS domain $Bri2_{113-231}$ was expressed in fusion with $NT_{D40K/K65D}$ or $NT_{wt}$ (SEQ ID NO: 68-69, encoding SEQ ID NO. 66-67). The proteins were cloned and expressed essentially in accordance with Example 3, in B121 or Origami E. coli cells, at 20° C. over night or at 30° C. for 4 hours.

FIG. 15 is an SDS-PAGE evaluation of expression and solubility of Bri2 BRICHOS fusion proteins. The $Bri2_{113-231}$ domain was fused C-terminally of $NT_{wt}$ (lane 1) or $NT_{D40K/K65D}$ (lane 2). Lane M denotes the size marker and the molecular weights are indicated to the left. Panel A shows an expression analysis before induction (lane B) and after expression (lane A) at 20° C. over night (left gel) or at 30° C. for 4 hours (right gel) in Origami E. coli cells. Both fusion protein variants showed a high expression level in both strains of bacteria although $NT_{wt}$ was slightly more efficient in Origami cells. Panel B shows a solubility analysis after lysozyme treatment followed by separation of soluble (lane S) and insoluble (lane P) fractions. Lysozyme treatment of harvested cells was inefficient although the $NT_{D40K/K65D}$ fusion protein was slightly more soluble. Panel C shows solubility analysis after 2 min of sonication in 20 mM Tris-HCl, pH 8, followed by separation of soluble (lane S) and insoluble (lane P) fractions. After sonication, both fusion proteins were predominantly found in the soluble fraction. The analysis was performed on cells previously expressed at 20° C. over night (left gel) or at 30° C. for 4 hours (right gel).

The fusion proteins were purified on Ni-sepharose followed by thrombin cleavage and a second purification step to remove the tag. The final yield of $Bri2_{113-231}$ protein (SEQ ID NO: 50) was 55 mg/L culture in Origami and 12 mg/L culture in B121 using any NT variant.

Example 11—Characterization of Bri2-BRICHOS (A) SDS-PAGE Analysis of Purified Bri2-BRICHOS FIG. 16 is an SDS-PAGE analysis of purification of Bri2-BRICHOS protein (SEQ ID NO: 50) obtained in Example 10. Samples from the purification steps were analyzed under reducing (panel A) and non-reducing (panel B) conditions for $Bri2_{113-231}$ in fusion with $NT_{wt}$ (lane 1) or $NT_{D40K/K65D}$ (lane 2). The molecular weights are indicated to the left. Supernatants were loaded on Ni-Sepharose and flow-through was collected (FT) followed by 4 washing steps with 10 mL running buffer (W1-W4). Pure fusion proteins were eluted with imidazole (F) and cleaved with thrombin (CL).

SDS-PAGE under reducing conditions (FIG. 16A) showed three bands (15, 12 and 10 kDa) for both fusion protein variants and they correlated well to the expected sizes of Bri2-BRICHOS (14 kDa) and NT (12 kDa and migrates as a smaller protein). The 12 kDa band is most probably truncated Bri2-BRICHOS unspecifically cleaved by thrombin. The same samples ran under non-reducing condition (FIG. 16B) showed that the 15 kDa and 12 kDa bands were able to form oligomers as expected from Bri2-BRICHOS.

(B) Gel Filtration

Figure 17:
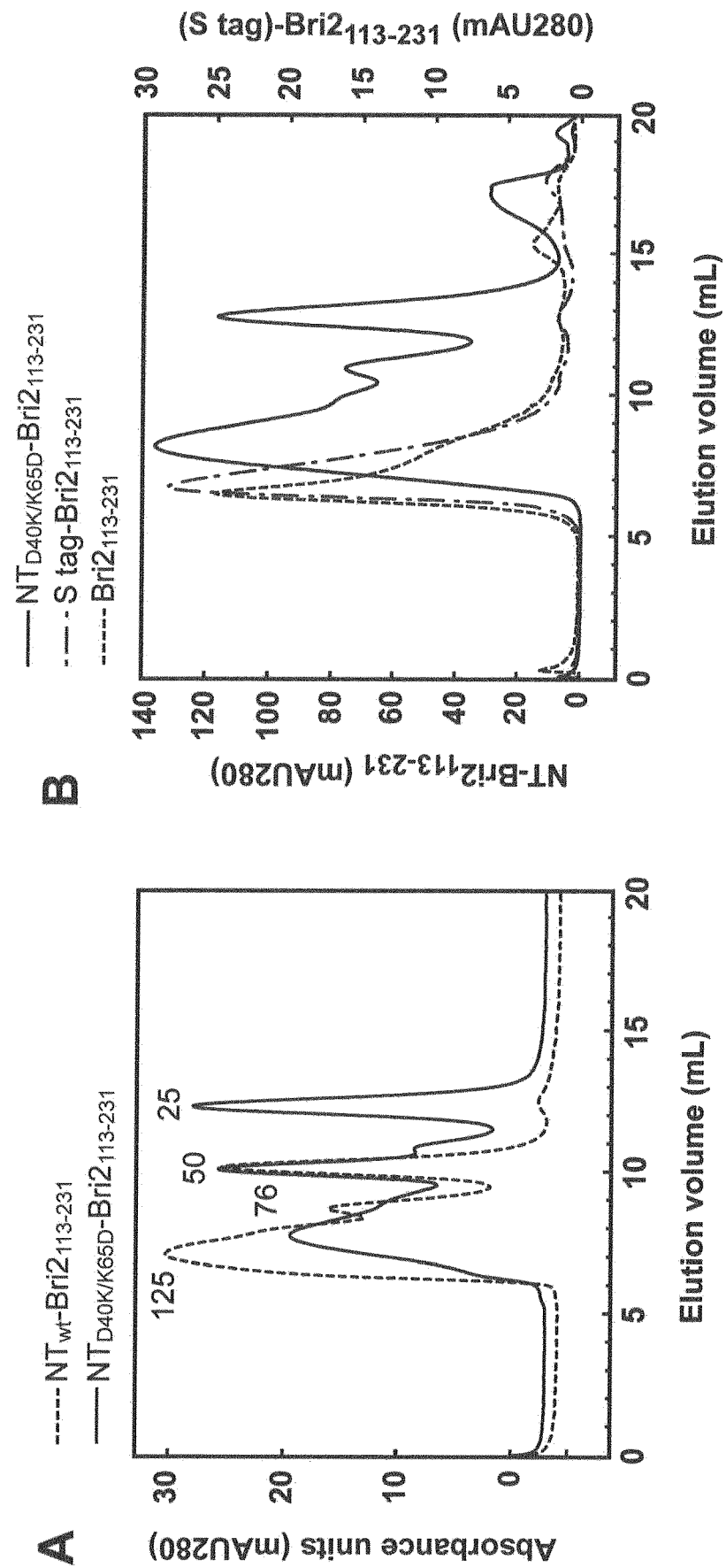
FIG. 17 shows gel filtration to determine the oligomeric state of Bri2$_{113-231}$ fusion proteins.

The conformation of the Bri2-BRICHOS protein (SEQ ID NO: 50) obtained in Example 10 was characterized using gel filtration essentially as set out in Example 9. Gel filtration was performed to estimate the proportion of fusion protein in their monomeric conformation. FIG. 17 shows gel filtration to determine the oligomeric state of $Bri2_{113-231}$ fusion proteins.

FIG. 17A shows a gel filtration analysis performed in 20 mM Tris, pH 8 for $Bri2_{113-231}$ in fusion with $NT_{wt}$ (dotted line) or $NT_{D40K/K65D}$ (filled line). When analyzing $NT_{wt}$-Bri2-BRICHOS, four peaks were distinguished. The peak at 25 kDa was close to the expected size of the monomeric fusion protein (29.7 kDa) but was small compared to other peaks. Dimer (50 kDa peak) and trimer (76 kDa peak) states were observed for both fusion proteins, and the $NT_{wt}$ fusion protein also formed very large oligomers/aggregates (125 kDa peak). Interestingly, the amount of protein with a monomer conformation (25 kDa peak) was significantly higher with the $NT_{D40K/K65D}$ fusion protein compared to the $NT_{wt}$ fusion protein. The results indicate that the NT mutant increases proper folding of Bri2-BRICHOS, leading to larger fraction of soluble monomeric Bri2-BRICHOS.

FIG. 17B shows that purification of $Bri2_{113-231}$ without NT yields predominantly large oligomeric forms. Gel filtration analysis was performed to determine the oligomeric state of $NT_{D40K/K65D}$-Bri2-BRICHOS fusion protein compared to Bri2-BRICHOS produced in fusion with an S-tag, or Bri2-BRICHOS produced alone. Without fusion to the NT mutant, the proteins migrated close to the void volume and were either aggregated or in a state of very large oligomers.

The above data indicate that $NT_{D40K/K65D}$ is able to mediate solubility and correct folding to Bri2-BRICHOS and also to prevent undesirable protein oligomerization.

Example 12—Expression of SP-A and SP-D Using a $NT_{D40K/K65D}$ Fusion Protein

SP-A and SP-D are essential soluble innate immune proteins of the lung, which act to survey the lung and bind to pathogens leading to their neutralization, agglutination and clearance. They are also important modulators of the function of various immune cells and of the inflammatory immune response. Mice deficient in either SP-A or SP-D show increased susceptibility to pathogenic infections including RSV as well as exaggerated inflammatory responses after infectious bacterial challenge. Significant effort has been made to develop recombinant forms of SP-A and SP-D to understand their molecular action within the lung in models of human respiratory disease. Recombinant SP-A and SP-D may also have therapeutic potential for the treatment of various human lung diseases (Salgado, D. et al. Front Immunol 5, 623 (2014)).

The oligomerization of trimers increases the affinity of SP-A and SP-D for carbohydrates on the surface of pathogens. Smaller fragments with the ability to form trimers also show activity, but are less efficient compared the native form. Heterologous expression of full-length SP-A and SP-D has so far only been successful in mammalian systems while truncated forms have been expressed in bacterial and yeast systems.

Full-length hSP-A1 (UniProt ID: Q8IWL2), hSP-A2 (UniProt ID: Q8IWL1) and hSP-D (UniProt ID: P35247) as well as truncated fragments thereof: $hSP-A1_{81-228}$ and $hSP-A2_{81-228}$ (Silveyra, P. & Floros, J., Gene 531: 126-132 (2013); SEQ ID NO: 47-48), and $hSP-D_{204-355}$ (Hakansson, K. et al. Structure 7: 255-264 (1999); SEQ ID NO: 49) are expressed in fusion with $NT_{D40K/K65D}$ (SEQ ID NO: 70-75, encoded by SEQ ID NO: 76-81). The fusion proteins are cloned and expressed essentially in accordance with Example 3, in B121 or Origami *E. coli* cells, at 20° C. over night or at 30° C. for 4 hours.

Example 13—Expression of Amyloid Beta (Aβ) Peptide Using a $NT_{D40K/K65D}$ Fusion Protein Aβ peptide is responsible for forming the amyloid plaques associated with Alzheimer's disease. The peptides are released from the amyloid precursor protein (APP) by proteolytic cleavage with beta and gamma secretase and can aggregate to form oligomers or larger fibrils that constitute amyloid plaques. The mechanisms of Aβ misfolding and fibrillation as well as the in vitro and in vivo toxicity of fibrils and intermediate oligomeric states have been extensively studied using synthetic peptides. Successful recombinant production of $Aβ_{1-40}$ and $Aβ_{1-42}$ peptides using a bacterial expression system has been demonstrated by extraction from inclusion bodies under denaturing conditions. This method does, however, not permit control over the oligomeric state of the peptides and require subsequent size-exclusion chromatography to obtain monomeric fractions prior to analysis.

To overcome this limitation Aβ1-42 (Uniprot ID P05067) is expressed in fusion with $NT_{D40K/K65D}$ (SEQ ID NO: 82, encoded by SEQ ID NO: 83). The fusion protein is cloned and expressed essentially in accordance with Example 3, in B121 or Origami *E. coli* cells, at 20° C. over night or at 30° C. for 4 hours.

Example 14—Expression of Islet Amyloid Polypeptide (IAPP) Using a $NT_{D40K/K65D}$ Fusion Protein The islet amyloid polypeptide (amylin or IAPP; Uniprot ID P10997) is a peptide hormone that is co-secreted with insulin from pancreatic β-cells and has an important role in the regulation of blood glucose levels. Studies suggest that pancreatic amyloid formed by IAPP is associated with the development of type II diabetes. IAPP is expressed as a pro-peptide called ProIAPP, which is processed to IAPP upon stimulation. Human proIAPP has previously been expressed recombinantly in fusion with the Trx solubility tag and purified by extraction from inclusion bodies under denaturing conditions. Recombinant human IAPP (hIAPP) peptide is available from a number of commercial sources and is delivered in fusion with a solubility tag such as GST or in conjugation to BSA or OVA in order to keep the peptide soluble.

Human IAPP is expressed in fusion with $NT_{D40K/K65D}$ (SEQ ID NO: 84, encoded by SEQ ID NO: 85). The fusion protein is cloned and expressed essentially in accordance with Example 3, in B121 or Origami *E. coli* cells, at 20° C. over night or at 30° C. for 4 hours.

Example 15—Expression of hCAP18 Using a $NT_{D40K/K65D}$ Fusion Protein

Cathelicidins are a family of antimicrobial and endotoxin-binding proteins found in granules of vertebrate neutrophils.

Figure 18:
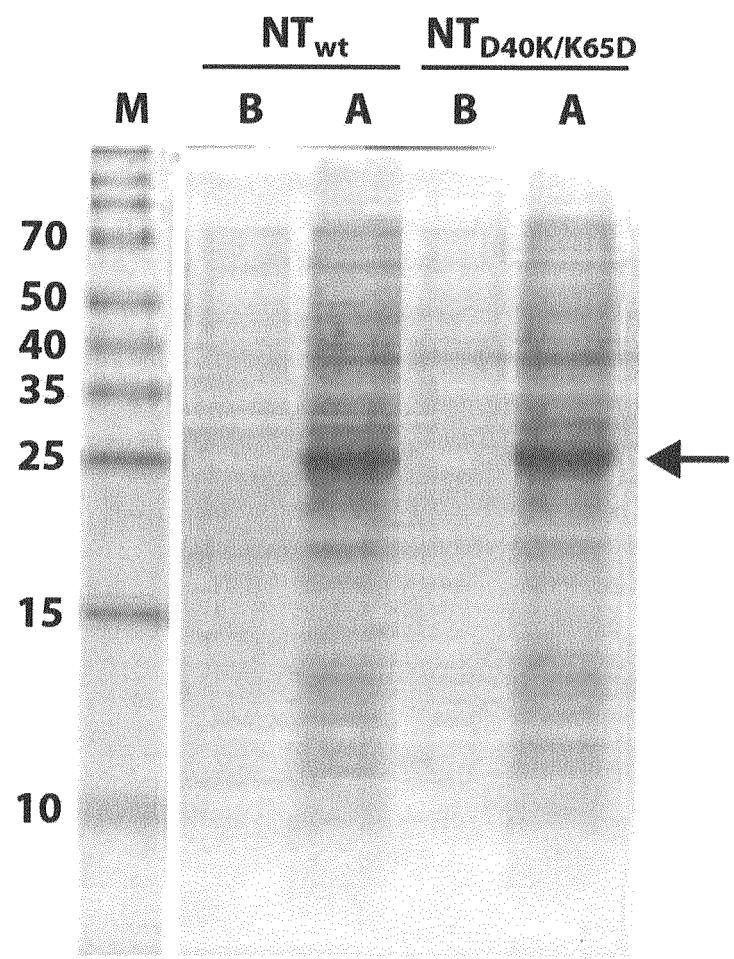
FIG. 18 shows a SDS-PAGE analysis of expressed hCAP18 in fusion with NT$_{wt}$ or NT$_{D40K/K65D}$.

Members of this family share a highly conserved 12 kDa N-terminus known as the cathelin-like domain. The biologically functional domain resides in the C-terminus and becomes activated when cleaved from the proprotein by serine proteases. The only human version of cathelicidin, hCAP18 is a proprotein to the antimicrobial peptide LL-37 that is released by extracellular cleavage with proteinase 3. hCAP18 inhibits growth of Gram-negative bacteria with efficiencies comparable to the mature peptide LL-37. However, recombinant production of hCAP18 is associated with low yields and an undetermined solubility, and new strategies are therefore needed for recombinant production.

hCAP18 without the signal peptide was cloned in fusion with $NT_{wt}$ or $NT_{D40K/K65D}$, respectively (SEQ ID NO: 86-87, encoded by SEQ ID NO: 88-89). Both fusion proteins were expressed in Origami E. coli cells at 20° C. overnight. FIG. 18 shows a SDS-PAGE analysis of expressed hCAP18 in fusion with $NT_{wt}$ or $NT_{D40K/K65D}$ before induction (B) and after over-night expression (A) at 20° C. The arrow indicates the expected band corresponding to the protein of interest.

After sonication at 80% amplitude, 1 s pulses on/off, for 2 minutes in total, using non-denaturing amounts of urea (2 M), 0.7% Tween or 10% glycerol as buffer additives, the fusion proteins were predominantly found in the soluble fraction after centrifugation, independent of buffer additive. The fusion proteins were purified on Ni-sepharose with a final yield around 50 mg/L culture.

Example 16—Expression of Nicastrin Using a $NT_{D40K/K65D}$ Fusion Protein

The γ-secretase protein complex is a four-component protease responsible for processing amyloid precursor protein (APP) and generating the Alzheimer's disease-associated peptide amyloid beta (An). Modulation of the activity and specificity of γ-secretase represents a potential therapeutic strategy for the treatment of Alzheimer's disease. One of the components, nicastrin or NCT, is a type I transmembrane glycoprotein with a large extracellular domain (ECD), which is thought to play a critical role in the recruitment of γ-secretase substrates. Heterologous E. coli production of full-length nicastrin ECD has so far not been reported.

The ECD of human nicastrin (UniProt ID: Q92542) is expressed in fusion with $NT_{D40K/K65D}$ (SEQ ID NO: 90, encoded by SEQ ID NO: 91). The fusion protein is cloned and expressed essentially in accordance with Example 3, in B121 or Origami E. coli cells, at 20° C. over night or at 30° C. for 4 hours.

Example 17—Expression of Green Fluorescent Protein (GFP) Using a $NT_{D40K/K65D}$ Fusion Protein GFP exhibits bright green fluorescence when exposed to light in the blue to ultraviolet range. GFP is frequently used as a reporter of expression due to the relatively small size that allows diffusion throughout cells without interfering with any biological processes. Many different mutants of GFP have been engineered and most importantly a S65T mutation dramatically increased the fluorescence and photostability. Enhanced GFP (eGFP) is the result of a F64L point mutation in addition to the S65T mutation, that showed increased folding efficiency at 37° C. and allowed practical use of GFP in mammalian cells eGFP was cloned in fusion with $NT_{wt}$ and $NT_{D40K/K65D}$ (SEQ ID NO: 92-93, encoded by SEQ ID NO: 94-95) and expressed in B121 E. coli cells at 20° C. over night. The cells were disrupted by lysozyme treatment instead of sonication. This method is less effective to solubilize protein but was required to maintain GFP fluorescence, which is otherwise partly lost during sonication treatment. Still, around 30-40% of the fusion protein was found in the soluble fraction after centrifugation and most protein was recovered during Ni-sepharose purification.

Example 18—$NT_{D40K/K65D}$ in Fusion with rSP-C33Leu Arranges into Micelle-Like Particles A purified and soluble $NT_{D40K/K65D}$-SP-C33Leu fusion protein (SEQ ID NO 56) was obtained as set out in Examples 3-4 and subjected to size exclusion chromatography (SEC) and transmission electron microscopy (TEM). For TEM, a purified and soluble $NT_{D40K/K65D}$ protein (SEQ ID NO: 2) was used as control.

Size-Exclusion Chromatography

Purified fusion protein was diluted to 2 mg/mL in running buffer (20 mM Tris, 150 mM NaCl, 1 mM EDTA, pH 8.0). A Superdex 200 column was equilibrated in running buffer and 200 uL of the sample was run through the column at a rate of 0.5 mL/min. Elution of protein was detected by measuring optical absorbance at 280 nm. Molecular weight standards ferritin (440 kDa), aldolase (158 kDa), conalbumin (75 kDa), ovalbumin (43 kDa), carbonic anhydrase (29 kDa) and ribonuclease A (13.7 kDa) (GE Healthcare) were run and eluted at 8.56 mL, 10.65 mL, 12.06 mL, 12.96 mL, 14.26 mL and 15.64 mL, respectively.

Transmission Electron Microscopy

The samples were diluted in 20 mM Tris, pH 8. For negative staining, 3 µl samples were applied to glow-discharged carbon-coated copper grids, stained with 2% (w/v) uranyl acetate and air-dried. The grids were checked using JEOL JEM-2100f transmission electron microscope operated at 200 kV. Images were collected with TVIPS TemCam-F415 4 k×4 k CCD-camera (Tietz Video and Image Processing Systems GmbH, Gauting, Germany) using a nominal magnification of 60000.

Figure 19:
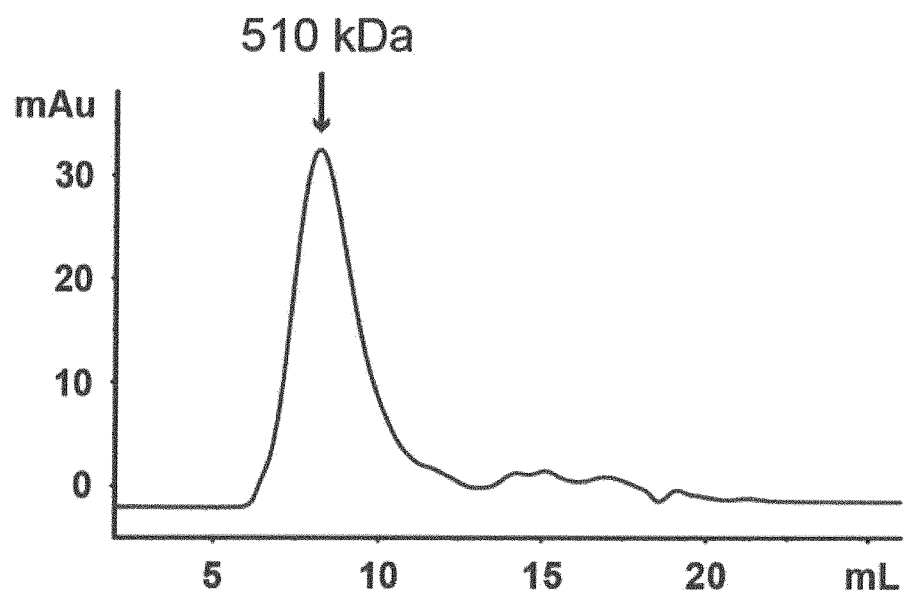
FIG. 19 shows SEC chromatograms of NT$_{D40K/K65D}$-SP-C33Leu fusion proteins.
Figure 20:
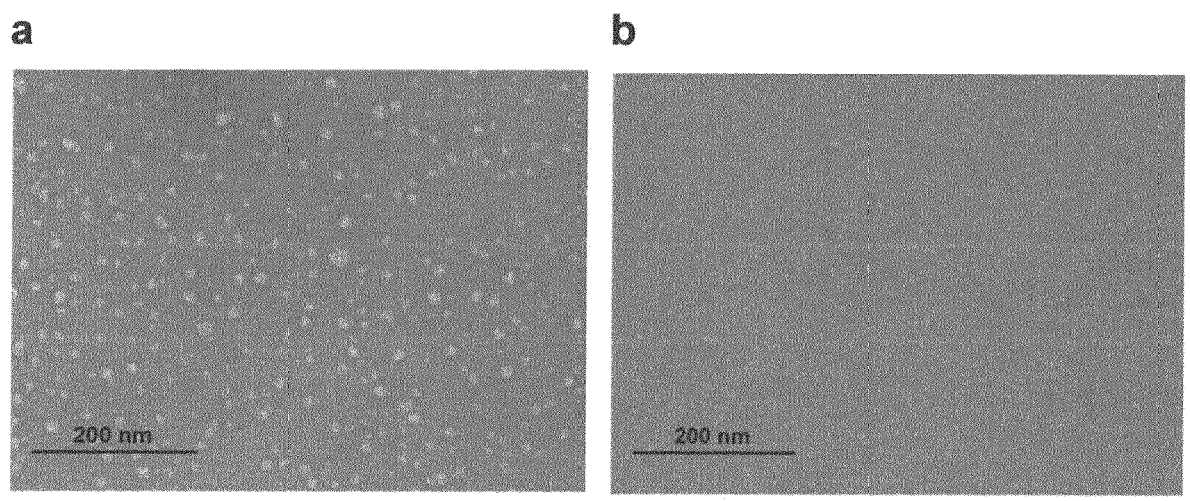
FIG. 20 shows TEM micrographs of negatively stained proteins containing NT$_{D40K/K65D}$.

While the $NT_{D40K/K65D}$-SP-C33Leu monomer has a calculated molecular mass of of 19 kDa, the SEC analysis presented in FIG. 19 showed a well-defined oligomer population with an estimated size of 510 kDa, corresponding to particles with a hydrodynamic radius around 10 nm. The presence of such micelle-like particles with a size of 10-15 nm was confirmed using negative staining transmission electron microscopy (TEM). In FIG. 20, panel (a) TEM of negatively stained $NT_{D40K/K65D}$-SP-C33Leu fusion protein shows 10-15 nm sized particles. In panel (b), TEM of negatively stained $NT_{D40K/K65D}$ protein at the same concentration served as negative control. No particles were observed for the $NT_{D40K/K65D}$ protein alone.

Example 19 (Comparative)—Protein Expression of Fusion Proteins Comprising $NT_{wt}$ and $NT_{A72R}$ EP 2 644 619 A1 discloses the solubility-enhancing moiety $NT_{A72R}$ and fusion proteins comprising the same. $NT_{A72R}$ is a constitutive monomer also below a pH of 6.4. The fusion proteins $NT_{A72R}$-SP-C33Leu (SEQ ID NO: 100) and $NT_{wt}$-SP-C33Leu (SEQ ID NO: 57) were expressed in E. coli BL21 (DE3) cells and purified in accordance with Examples 3-4.

The obtained proteins were separated by SDS-PAGE and stained with Coomassie. The different fusion proteins were investigated and the expression (production) levels per bacterium were found to be in the order $NT_{wt}$-SP-C33Leu>$NT_{A72R}$-SP-C33Leu.

In conclusion, $NT_{A72R}$ does not improve the fusion protein expression levels compared to $NT_{wt}$.

Example 20—Expression and Purification of Modified Spidroin Proteins

A spidroin protein with a modified fibronectin-derived RGD loop, $FN_{cc}$, a repetitive moiety and a CT moiety from a minor ampullate spidroin (MiSp) was cloned in fusion with $NT_{D40K/K65D}$ and Z, respectively (SEQ ID NO: 101-102). Identical fusion proteins but with a CT moiety from a major ampullate spidroin (MaSp) were also cloned (SEQ ID NO: 103-104).

To test expression levels of the modified spidroin proteins, the fusion proteins were cloned into pT7 expression vectors and transformed into chemically competent E. coli BL21 (DE3) cells.

Plasmid-containing cells were inoculated to 150 mL LB medium with 50 mg/L kanamycin and grown at 30° C. and 220 rpm over night. 5 mL over-night culture was inoculated to 500 mL LB medium (1/100) with kanamycin and cells were further grown at 30° C. to OD ~1. The cells were induced by addition of IPTG to a final concentration of 0.3 mM and expression was performed at 15° C. over night. After 19 hours of expression the cells were harvested by centrifugation, resuspended in 20 mM Tris-HCl, pH 8 to 40 mL and stored at −20° C. for at least 24 hours. Cells were solubilized by the addition of lysozyme. The soluble and insoluble fractions were separated by centrifugation at 21612×g, 4° C. for 30 min.

Duplicate culture samples equal to $OD_{600}=1$ were taken after 4 and 19 hours of induction during expression. Samples were pelleted through centrifugation at 13000×g, 4° C. for 10 min, the supernatant was discarded and the pellets were stored at −20° C. for at least 24 h. Pelleted material were lysed using CelLytic B™ with the addition of lysozyme. One sample per time point was used for the analysis of the soluble and insoluble fraction which were separated through centrifugation at 13000×g, RT for 10 min. The other samples were used for whole cell analysis without separating the soluble and insoluble fractions.

To the samples equal amounts of reducing SDS-PAGE loading buffer was added, boiled for 5 min at 95° C. and subsequently loaded in equal amounts on a 12% acrylamide gel. The proteins were transferred to a membrane using iBlot 2® Dry Blotting System. iBind™ Western Device is used for blotting using an IRDYE800CW® fluorophore labeled chicken anti-his antibody. Detection is performed using a Liquor Odyssey fc® imaging system.

To the clear lysate from the cultures, NaCl and imidazole was added to a final concentration of 500 mM and 20 mM respectively and loaded to an IMAC column, previously packed with Zn-Sepharose (GE Healthcare) and equilibrated with loading buffer (20 mM Tris, 20 mM Imidazole and 500 mM NaCl, pH 8). Bound protein was washed with 20 mM Tris-HCl, 49 mM imidazole, 500 mM NaCl, pH 8 and eluted with 20 mM Tris-HCl, 220 mM imidazole, 500 mM NaCl, pH 8 in 1 mL fractions. The absorbance at 280 nm was measured for each fraction, and protein-rich fractions were pooled. Imidazole was removed by over-night dialysis at 4° C. and in 5 L loading buffer, using a Spectra/Por® dialysis membrane with a 6-8 kDa molecular weight cut-off. The purity of the protein in each step was determined by SDS-PAGE using a 12% acrylamide gel stained with Coomassie Brilliant Blue.

After storage at −20° C., the fusion proteins were thawed at 4° C., centrifuged for 10 min at 4570×g and concentrated. Samples were stored at 4° C. The stability was evaluated numerically by measuring concentration over the span of 3 days using Nano Drop™ and visually by SDS-PAGE, using a 12 4° C. acrylamide gel stained with InstantBlue™ protein stain. It is concluded that $NT_{D40/K65D}$ is more effective than the Z-tag in keeping highly aggregation-prone purified spidroin proteins in solution.

Example 21—Expression of Spidroin Fusion Proteins

To test expression levels of spidroin fusion proteins, the IgG fragment sCD40 covalently linked to 4RepCT was cloned in fusion with $NT_{D40K/K65D}$ and Z, respectively (SEQ ID NO: 105-106), into pT7 expression vectors and transformed into chemically competent E. coli BL21 (DE3) cells.

Plasmid-containing cells were inoculated to 150 mL LB medium with 50 mg/L kanamycin and grown at 30° C. and 220 rpm over night. 5 mL over-night culture was inoculated to 500 mL LB medium (1/100) with kanamycin and cells were further grown at 30° C. to OD ~1. The cells were induced by addition of IPTG to a final concentration of 0.3 mM and expression was performed at 15° C. over night. After 19 hours of expression the cells were harvested by centrifugation, resuspended in 20 mM Tris-HCl, pH 8 to 40 mL and stored at −20° C. for at least 24 hours.

In order to analyse the amount of protein expressed in the soluble and insoluble fraction, respectively, culture samples are taken and analyzed using western blot, as described in Example 20.

Example 22—Expression of IgG Fragments

The IgG fragment sCD40 covalently linked to a sortase recognition sequence in fusion with $NT_{D40K/K65D}$ and Z, respectively (SEQ ID NO: 107-108), were cloned into pT7 expression vectors and transformed into chemically competent E. coli BL21 (DE3) cells.

Plasmid-containing cells were inoculated to 20 mL LB medium with 50 mg/L kanamycin and grown at 30° C. and 220 rpm over night. 5 mL over-night culture was inoculated to 500 mL LB medium (1/100) with kanamycin and cells were further grown at 30° C. to OD ~1. The cells were induced by addition of IPTG to a final concentration of 0.3 mM, and expression was performed at 15° C. over night. After 19 hours of expression the cells were harvested by centrifugation, resuspended in 20 mM Tris-HCl, pH 8 to 40 mL and stored at −20° C. for at least 24 hours.

In order to analyse the amount of protein expressed in the soluble and insoluble fraction, respectively, culture samples are taken and analyzed using western blot, as described in Example 20.

The invention claimed is:

1. A protein comprising a moiety of 100-160 amino acid residues having at least 70% identity with any one of SEQ ID NO: 1, 13-23, 25-26 and 96-99, wherein the amino acid residue corresponding to position 40 in SEQ ID NO: 1 is selected from the group consisting of Lys, Arg and His; and wherein the basic amino acid residue of the protein corresponding to position 65 in SEQ ID NO: 1 is selected from the group consisting of Asp and Glu.

2. The protein according to claim 1, wherein the amino acid residue corresponding to position 40 in SEQ ID NO: 1 is Lys or Arg.

3. The protein according to claim 1, wherein the amino acid residue corresponding to position 65 in SEQ ID NO: 1 is Asp.

4. The protein according to claim 1, which is a fusion protein further comprising a second moiety that is a desired protein or polypeptide,
   wherein the first moiety as defined in claim 1 enhances the solubility of the second moiety.

5. The protein according to claim 4, further comprising
   (iii) at least one cleavage site arranged between at least one desired protein or polypeptide moiety and at least one solubility-enhancing moiety.

6. A micelle comprising the protein according to claim 1.

7. The protein according to claim 1, wherein the amino acid residue corresponding to position 40 in SEQ ID NO: 1 is Lys.

8. A protein according to claim 1, wherein the moiety has at least 70% identity with SEQ ID NO: 1.

9. A protein comprising a moiety of 100-160 amino acid residues having at least 70% identity with SEQ ID NO: 1, wherein the amino acid residue of the moiety corresponding to the residue at position 40 in SEQ ID NO: 1 is Lys, Arg or His; and wherein the amino acid residue of the moiety corresponding to the residue at position 65 in SEQ ID NO: 1 is Asp or Glu.

10. A protein comprising a moiety of 100-160 amino acid residues having at least 70% identity with any one of SEQ ID NO: 1 and 13-21, wherein the amino acid residue of the moiety corresponding to the residue at position 40 in SEQ ID NO: 1 is Lys, Arg or His; and wherein the basic amino acid residue of the moiety corresponding to the residue at position 65 in SEQ ID NO: 1 is Asp or Glu.

* * * * *